(12) United States Patent
Brooks et al.

(10) Patent No.: US 7,345,070 B2
(45) Date of Patent: *Mar. 18, 2008

(54) PEROXISOME PROLIFERATOR ACTIVATED RECEPTOR AGONISTS

(75) Inventors: Dawn Alisa Brooks, Indianapolis, IN (US); Alexander Glenn Godfrey, Mooresville, IN (US); Sarah Beth Jones, Greenwood, IN (US); James Ray McCarthy, Zionsville, IN (US); Christopher John Rito, Martinsville, IN (US); Leonard Larry Winneroski, Greenwood, IN (US); Yanping Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 247 days.

This patent is subject to a terminal disclaimer.

(21) Appl. No.: 11/054,226

(22) Filed: Feb. 9, 2005

(65) Prior Publication Data

US 2005/0245584 A1   Nov. 3, 2005

Related U.S. Application Data

(62) Division of application No. 10/343,476, filed on Jan. 29, 2003, now Pat. No. 6,930,120.

(60) Provisional application No. 60/227,234, filed on Aug. 23, 2000.

(51) Int. Cl.
*A31K 31/421* (2006.01)
*C07D 263/32* (2006.01)

(52) U.S. Cl. ................................ 514/374; 548/236

(58) Field of Classification Search ............... 548/236; 514/374
See application file for complete search history.

(56) References Cited

U.S. PATENT DOCUMENTS

| | | | |
|---|---|---|---|
| 5,089,514 A | 2/1992 | Hulin | |
| 5,232,945 A | 8/1993 | Hulin | |
| 5,306,726 A | 4/1994 | Hulin | |
| 5,902,726 A | 5/1999 | Kliewer et al. | |
| 5,994,554 A | 11/1999 | Kliewer et al. | |
| 7,176,224 B2 * | 2/2007 | Ardecky et al. | ............ 514/374 |

FOREIGN PATENT DOCUMENTS

| | | |
|---|---|---|
| EP | 0 930 229 | 7/1999 |
| GB | 2 359 082 | 8/2001 |
| WO | WO 97/28115 | 8/1997 |
| WO | WO 97/31907 | 9/1997 |
| WO | WO 99/46232 | 9/1999 |
| WO | WO 01/16120 | 3/2001 |
| WO | WO 02/16332 | 2/2002 |
| WO | WO 02/18355 | 3/2002 |

OTHER PUBLICATIONS

Collins et al., N-(2-Benzoylphenyl), etc., J. Med. Chem. 1988, 41, 5037-5054.*

Sarges, R., et al.: "*Glucose Transport-Enhancing and Hypoglycemic Activity of 2-Methyl-2-Phenoxy-3-Phenylpropanoic Acids*"; Journal of Medicinal Chemistry, vol. 39, No. 24, Nov. 22, 1996, pp. 4783-4803.

Cobb, J. E., et al.: "*N-(2-Benzoylphenyl)-L-Tyrosine PPARGamma Agonists. 3. Structure-Activity Relationship and Optimization of the N-Aryl Substituent*"; Journal of Medicinal Chemistry, vol. 41, No. 25, Dec. 3, 1998, pp. 5055-5069.

Bright, S.W., et. al.: "*Competitive Particle Concentration Fluorescence Immunoassays for Measuring Anti-Diabetic Drug Levels in Mouse Plasma*"; Journal of Immunological Methods, vol. 207, No. 1, Aug. 22, 1997, pp. 23-31.

Brooks, D., et al.: "*Design and Synthesis of 2-methyl-2-{4-'2-'5-methyl-2-aryloxazol-4-yl)oxylphenoxy}propionic acids: A New Class of Dual PPARAlpha/Gamma Agonists*"; Journal of Medicinal Chemistry, vol. 44, No. 13, June 21, 2001, pp. 2061-2064.

(Continued)

*Primary Examiner*—Patricia L. Morris
(74) *Attorney, Agent, or Firm*—MaCharri Vorndran-Jones; Soonhee Jang

(57) ABSTRACT

Compounds represented by the following structural formula (I), and pharmaceutically acceptable salts, solvates and hydrates thereof, wherein: n is 2, 3, or 4 and W is $CH_2$, CH(OH), C(O) or O; R1 is an unsubstituted or substituted aryl, heteroaryl, cycloalkyl, heterocycloalkyl, aryl-alkyl, heteroaryl-alkyl, cycloalkyl-alkyl, or t-butyl; R2 is H, alkyl, haloalkyl or phenyl; Y is an unsubstituted or substituted thiophen-2,5-diyl or phenylene; R3 is alkyl or haloalkyl; R4 is a substituted or unsubstituted phenyl, naphthyl, 1,2,3,4-tetrahydronaphthyl, quinolyl, pyridyl or benzo[1,3]dioxol-5-yl group; and R5 is H, alkyl, or aminoalkyl; are useful for modulating a peroxisome proliferator activated receptor, particularly in the treatment of diabetes mellitus.

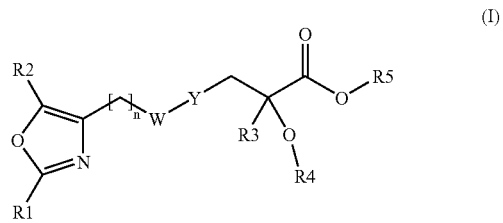

(I)

6 Claims, No Drawings

OTHER PUBLICATIONS

Shinkai, H. et al.: "*Isoxazolidine-3,5-dione and Noncyclic 1,3-dicarbonyl Compounds as Hypoglycemic Agents*"; Journal of Medicinal Chemistry vol. 41, No. 11, May 21, 1998, pp. 1927-1933.

Murugesan, N., et al.: "*Biphenylsulfonamide Endothelin Receptor Antogonists 2. Discovery of 4'-oxazoly-lbiphenylsulfonamides as a New Class of Poent, Highly Selective ET(A)Antagonists*"; Journal of Medicinal Chemistry, vol. 43, No. 16, Aug. 10, 2000, pp. 3111-3117.

Malamas, M.S., et al.: "*Azole Phenoxy Hydroxyureas as Selective and Orally Active Inhibitors fo 5-Lipoxygenase*"; Journal of Medicinal Chemistry, vol. 39, No. 1, Jan. 5, 1996, pp. 237-245.

Merguro, K., et al.: "*Studies on Antidiabetic Agents. VII. Synthesis and Hypoglycemic Activity fo 4-Oxazoleacetic Acid Derivatives*"; Chemical & Pharmaceutical Bulletin, vol. 34, No. 7, 1986, pp. 2840-2851.

\* cited by examiner

PEROXISOME PROLIFERATOR ACTIVATED RECEPTOR AGONISTS

This application is a divisional application of U.S. patent application Ser. No. 10/343,476, filed Jan. 29, 2003 now U.S. Pat. No. 6,930,120, which claims the benefit of U.S. Provisional Application No. 60/227,234, filed Aug. 23, 2000, the entire teachings of which are incorporated herein by reference.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include PPARα, PPARβ or NUC1, PPARγ and PPARδ.

The PPARα receptor subtypes are reported to be activated by medium and long-chain fatty acids. They are involved in stimulating beta-oxidation of fatty acids and with the activity of fibrates which reportedly produce a substantial reduction in plasma triglycerides and moderate reduction in low density lipoprotein (LDL) cholesterol. The PPARγ receptor subtypes are reportedly involved in activating the program of adipocyte differentiation and are not involved in stimulating peroxisome proliferation in the liver.

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL which are risk factors in cardiovascular diseases. The constellation of symptoms which includes hyperinsulemia combined with hypertension, elevated body weight, elevated triglycerides and elevated LDL is known as Syndrome X.

Current treatment for diabetes mellitus generally first involves treatment with diet and exercise. However, compliance can be poor and as the disease progresses treatment with hypoglycemics, typically sulfonylureas, is often necessary. Sulfonylureas stimulate the β cells of the liver to secrete more insulin. However, the response of the β cells eventually fails and treatment with insulin injection is necessary. In addition, both sulfonylurea treatment and insulin injection have the life threatening side effect of hypoglycemic coma. Therefore, patients using these treatments must carefully control dosage.

Thiazolidinediones are a class of compounds which have been shown to increase the sensitivity of insulin sensitive cells. Increasing insulin sensitivity rather than the amount of insulin in the blood reduces the likelihood of hypoglycemic coma. Thiazolidinediones have been shown to increase insulin sensitivity by binding to PPARγ receptors. However, side effects associated with treatment with thiazolidinediones include weight gain, and, for troglitazone, liver toxicity.

PPARα and PPARγ receptors have been implicated in diabetes mellitus, cardiovascular disease, obesity, and gastrointestinal disease, such as, inflammatory bowel disease. There exists a need for new pharmaceutical agents which modulate these receptors to prevent, treat and/or alleviate these diseases or conditions while ameliorating side effects of current treatments.

SUMMARY OF THE INVENTION

The present invention is directed to compounds represented by Structural Formula I and pharmaceutically acceptable salts, solvates and hydrates thereof:

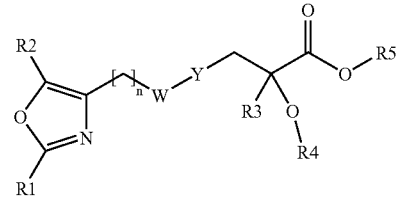

Structural Formula I

In Structural Formula I, n is 2, 3, or 4 and W is $CH_2$, CH(OH), C(O) or O. R1 is an unsubstituted or substituted group selected from aryl, heteroaryl, cycloalkyl, heterocycloalkyl, aryl-C1-C4 alkyl, heteroaryl-C1-C4 alkyl, cycloalkyl-C1-C4 alkyl, or t-butyl. R2 is H, C1-C4 alkyl, C1-C4 haloalkyl or phenyl. Y is an unsubstituted or substituted group consisting of thiophen-2,5-diyl or phenylene. R3 is C1-C4 alkyl or C1-C4 haloalkyl. R4 is a substituted or unsubstituted phenyl, naphthyl, 1,2,3,4-tetrahydronaphthyl, quinolyl, pyridyl or benzo[1,3]dioxol-5-yl group. R5 is H, C1-C4 alkyl, or aminoalkyl.

In one embodiment, the present invention also relates to pharmaceutical compositions which comprising at least one compound of the present invention, or a pharmaceutically acceptable salt, solvate, hydrate or prodrug thereof, and a pharmaceutically acceptable carrier.

In another embodiment, the present invention relates to a method of modulating a peroxisome proliferator activated receptor by contacting the receptor with at least one compound represented by Structural Formula I, and pharmaceutically acceptable salts, solvates and hydrates thereof In a further embodiment, the present invention relates to a method of making a compound represented by Structural Formula I.

The compounds of the present invention and pharmaceutically acceptable salts, solvates and hydrates thereof are believed to be effective in treating Syndrome X, Type II diabetes, hyperglycemia, hyperlipidemia, obesity, coagaulopathy, hypertension, atherosclerosis, and other disorders related to Syndrome X and cardiovascular diseases because they lower one or more of the following in mammals: glucose, insulin, triglycerides, fatty acids and/or cholesterol. In addition, the compounds exhibit fewer side effects than compounds currently used to treat these conditions.

DETAILED DESCRIPTION OF THE INVENTION

The terms used to describe the instant invention have the following meanings herein.

As used herein, alkyl groups include straight chained or branched C1-C4 hydrocarbons, which are completely saturated.

Cycloalkyl groups, as used herein, include C3-C8 hydrocarbons, which are partially or completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl). Heteroaryl groups, as used herein, is an aromatic ring system having at least one heteroatom such as nitrogen, sulfur or oxygen. Heteroaryl groups include thienyl (also referred to herein as "thiophenyl"), pyridyl, pyrrolyl, benzofuranyl, isoxazolyl, and pyrimidinyl.

An aryl-C1-C4-alkyl group, as used herein, is an aryl substituent that is linked to a compound by an alkyl group having from one to four carbon atoms.

A heteroaryl-C1-C4-alkyl group, as used herein, is a heteroaryl substituent that is linked to a compound by an alkyl group having from one to four carbon atoms.

A cycloalkyl-C1-C4-alkyl group, as used herein, is a cycloalkyl substituent that is linked to a compound by an alkyl group having from one to four carbon atoms.

An aminoalkyl group is an alkyl group having from one to six carbon atoms which is substituted with at least one amine represented by —NR12R12 in which each R12 are, independently, a C1-C6 alkyl or both R12 taken together with the nitrogen to which they are attached form a five or six membered heterocycloalkyl.

A heterocycloalkyl is a non-aromatic ring which contains one or more oxygen, nitrogen or sulfer (e.g., morpholine, piperidine, piperazine, pyrrolidine, and thiomorpholine). Preferred heterocycloalkyl group is morpholine.

Substituents for aryl, heteroaryl and cycloalkyl groups include halo, carboxyl, C1-C4 alkyl, C1-C4 alkoxy, C1-C4 haloalkyl, C1-C4 haloalkoxy, nitro, cyano, CHO, hydroxyl, C1-C4 alkanoic acid and —C(O)NR13R13 in which each R13, independently, H or a C1-C4 alkyl. Substituents for thiophen-2,5-diyl and phenylene include H, C1-C4 alkyl, C1-C4 alkoxy, C1-C4 haloalkyl and C1-C4 haloalkoxy.

Preferably, the compounds of the present invention, and with their respective pharmaceutical compositions, have a structure represented by Structural Formula II:

Structural Formula II

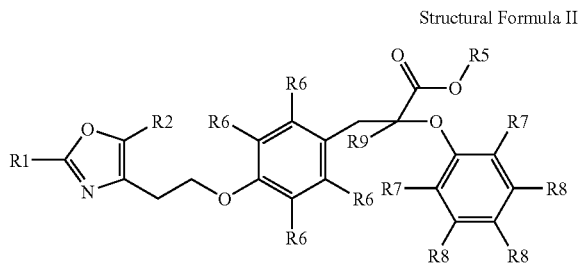

In Structural Formula II, R1, R2 and R5 are as defined for Structural Formula I while R6 are each, independently, H, C1-C4 alkyl or C1-C4 alkoxy. In addition, R7 are each, independently, H, halo, C1-C4 alkyl, C1-C4 alkoxy, C1-C4 haloalkyl, C1-C4 haloalkoxy, nitro, methanesulfonyl, C3-C8 cycloalkyl, thienyl or phenyl. R8 are each, independently, H, halo, C1-C4 alkyl, C1-C4 alkoxy, C1-C4 haloalkyl, C1-C4 haloalkoxy, nitro, methanesulfonyl, C3-C8 cycloalkyl, thienyl, phenyl or together with the phenyl to which they are bound form naphthyl, 1,2,3,4-tetrahydronaphthyl, quinolyl or benzo[1,3]dioxol-5-yl. Further, R9 is C1-C4 alkyl or C1-C4 haloalkyl.

Examples of compounds having Structural Formula II include, for instance, the compounds described in Examples 1-89 and 92-140.

More preferably, the compounds of the present invention, and with their respective pharmaceutical compositions, have a structure represented by Structural Formula III:

Structural Formula III

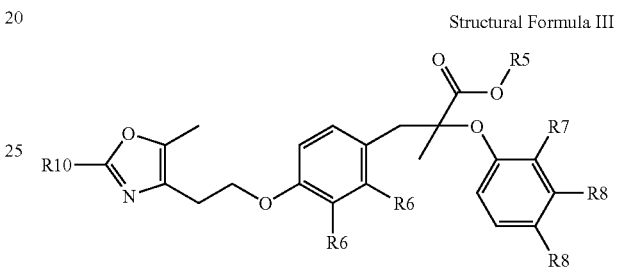

In Structural Formula III, R5, R6, R7 and R8 are as defined for Structural Formulas I and II while R10 is an unsubstituted or substituted group selected from 2-thienyl, 3-thienyl, phenyl, cyclohexyl or 1-methyl-cyclohexyl.

Even more preferably, the compounds of the present invention, and with their respective pharmaceutical compositions, have a structure represented by Structural Formula IV or V.

Structural Formula IV

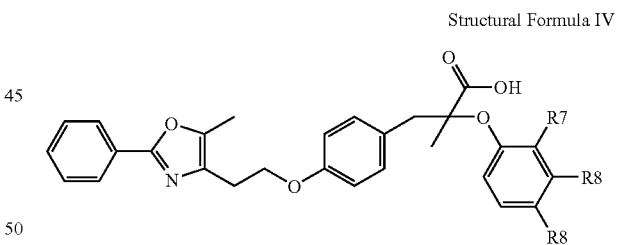

Structural Formula V

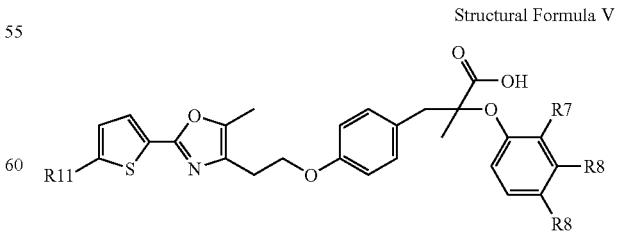

In Structural Formulas IV and V, R7 and R8 are as defined for Structural Formula II while R11 is H, halo or C1-C4 alkyl.

In an alternate embodiment, the compounds of the present invention, and with their respective pharmaceutical compositions, have a structure represented by Structural Formula VI.

Structural Formula VI

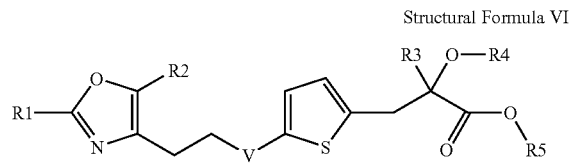

In Structural Formula VI, R1, R2, R3, R4 and R5 are as defined for Structural Formula I while V is C, C(OH) or C(O).

The compounds of Structural Formula I contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

In a more preferred embodiment, the compounds of the present invention are S-enantiomers. In a most preferred embodiment, the compounds are (S)-3-{4-[2-(2-Phenyl-5-methyl-oxazol-4-yl)-ethoxy]-phenyl}-2-methyl-2-phenoxypropionic acid, (S)-2-Methyl-3-{4-[2-(5-methyl-2-thiophen-2-yl-oxazol-4-yl)-ethoxy]-phenyl}-2-phenoxypropionic acid, and (S)-3-{4-[2-(2-cyclohexyl-5-methyl-oxazol-4-yl)ethoxy]-phenyl}-2-methyl-2-p-tolyloxy-propionic acid.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may exist in more than one crystal form. Polymorphs of compounds represented by Structural Formula I form part of this invention and may be prepared by crystallization of a compound of Structural Formula I under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of Structural Formula I followed by gradual or fast cooling. The presence of polymorphs may be determined by solid probe nmr spectroscopy, ir spectroscopy, differential scanning calorimetry, powder X-ray diffraction or such other techniques.

Certain compounds of Structural Formula I and their salts may exist in more than one crystal form and the present invention includes each crystal form and mixtures thereof.

Certain compounds of Structural Formula I and their salts may also exist in the form of solvates, for example hydrates, and the present invention includes each solvate and mixtures thereof.

"Pharmaceutically-acceptable salt" refers to salts of the compounds of the Structural Formula I which are substantially non-toxic to mammals. Typical pharmaceutically-acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

By virtue of its acidic moiety, a compound of Structural Formula I forms salts with pharmaceutically acceptable bases. Some examples of base addition salts include metal salts such as aluminum; alkali metal salts such as lithium, sodium or potassium; and alkaline earth metal salts such as calcium, magnesium, ammonium, or substituted ammonium salts. Examples of substituted ammonium salts include, for instance, those with lower alkylamines such as trimethylamine, triethylamine; hydroxyalkylamines such as 2-hydroxyethylamine, bis-(2-hydroxyethyl)-amine or tri-(2-hydroxyethyl)-amine, cycloalkylamines such as bicyclohexylamine or dibenzylpiperidine, N-benzyl-β-phenethylamine, dehydroabietylamine, N,N'-bisdehydro-abietylamine, glucamine, N-methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of Structural Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)- tartrates or mixtures thereof including racemic mixtures], succinates, benzoates and salts with amino acids such as glutamic acid.

These salts may be prepared by methods known to those skilled in the art.

Certain compounds of Structural Formula I and their salts may also exist in the form of solvates, for example hydrates, and the present invention includes each solvate and mixtures thereof.

Prodrugs are compounds of the present invention, which have chemically or metabolically cleavable groups and become by solvolysis or under physiological conditions the compounds of the invention which are pharmaceutically active in vivo. Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl) oxy)alkyl esters. Particularly preferred esters as prodrugs are methyl, ethyl, propyl, isopropyl, n-butyl, isobutyl, tert-butyl, morpholinoethyl, and N,N-diethylglycolamido.

Methyl ester prodrugs may be prepared by reaction of the acid form of a compound of Formula I in a medium such as methanol with an acid or base esterification catalyst (e.g., NaOH, $H_2SO_4$). Ethyl ester prodrugs are prepared in similar fashion using ethanol in place of methanol. Morpholinylethyl ester prodrugs may be prepared by reaction of the sodium salt of a compound of Structural Formula I (in a medium such as dimethylformamide) 4-(2-chloroethyl)morphine hydrochloride (available from Aldrich Chemical Co., Milwaukee, Wis. USA, Item No. C4, 220-3).

The term, "active ingredient" means the compounds generically described by Structural Formula I as well as the salts, solvates, and prodrugs of such compounds.

The term "pharmaceutically acceptable" means that the carrier, diluent, excipients and salt must be compatible with the other ingredients of the composition, and not deleterious to the recipient thereof. Pharmaceutical compositions of the present invention are prepared by procedures known in the art using well known and readily available ingredients.

"Preventing" refers to reducing the likelihood that the recipient will incur or develop any of the pathological conditions described herein.

"Treating" refers to mediating a disease or condition and preventing, or mitigating, its further progression or ameliorate the symptoms associated with the disease or condition.

"Pharmaceutically-effective amount" means that amount of a compound, or of its salt, solvate, hydrate or prodrug thereof, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a PPAR receptor, such as a PPARα or PPARγ receptor, which mediate a disease or condition. Conditions mediated by PPARα or PPARγ receptors include diabetes mellitus, cardiovascular disease, Syndrome X, obesity and gastrointestinal disease.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The human to whom the compounds and compositions of the present invention are administered has a disease or condition in which control blood glucose levels are not adequately controlled without medical intervention, but wherein there is endogenous insulin present in the human's blood. Non-insulin dependent diabetes mellitus (NIDDM) is a chronic disease or condition characterized by the presence of insulin in the blood, even at levels above normal, but resistance or lack of sensitivity to insulin action at the tissues. The compounds and compositions of the present invention are also useful to treat acute or transient disorders in insulin sensitivity, such as sometimes occur following surgery, trauma, myocardial infarction, and the like. The compounds and compositions of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof and/or a pharmaceutically acceptable solvate thereof to a hyperglycemic human or non-human mammal in need thereof.

They are useful as therapeutic substances in preventing or treating Syndrome X, diabetes mellitus and related endocrine and cardiovascular disorders and diseases in human or non-human animals.

The invention also relates to the use of a compound of Formula I as described above, for the manufacture of a medicament for treating a PPARα or PPARγ mediated condition, separately or in combination.

A therapeutically effective amount of a compound of Structural Formula I can be used for the preparation of a medicament useful for treating Syndrome X, diabetes, treating obesity, lowering tryglyceride levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention (1) typically reduces serum glucose levels, or more specifically HbA1c, of a patient by about 0.7% or more; (2) typically reduces serum triglyceride levels of a patient by about 20% or more, and (3) increases serum HDL levels in a patient. Preferably, HDL levels will be increased by about 30% or more.

Additionally, an effective amount of a compound of Structural Formula I and a therapeutically effective amount of one or more active agents selected from a group consisting of: antihyperlipidemic agent, plasma HDL-raising agents, antihypercholesterolemic agents, fibrates, vitamins, aspirin, insulin secretogogues, insulin and the like can be used together for the preparation of a medicament useful for the above-described treatments.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active-agents depending on the desired target therapy. Combination therapy includes administration of a single pharmaceutical dosage composition which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salts, solvates and hydrates thereof, have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient which is a compound of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

For oral administration, the compounds can be formulated readily by combining the active compounds with pharmaceutically acceptable carriers well known in the art. Such carriers enable the compounds of the invention to be formulated as tablets, pills, powders, sachets, granules, dragees, capsules, liquids, elixers, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid, or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like. When a dosage unit form is a capsule, it may contain, in addition to materials of the above type, a liquid carrier such as a fatty oil.

Solid form formulations include powders, tablets and capsules. A solid carrier can be one or more substance which may also act as flavoring agents, lubricants, solubilisers, suspending agents, binders, tablet disintegrating agents and encapsulating material.

In powders, the carrier is a finely divided solid which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration the compounds of the present invention, or salts thereof, can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks's solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

The following pharmaceutical formulations 1 through 8 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active Ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
| --- | --- |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| Active Ingredient | 225 mg |
| --- | --- |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| Active Ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |

| | |
|---|---|
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active Ingredient | 100 mg |
| Isotonic saline | 1,000 ml |

The solution of the above materials generally is administered intravenously to a subject at a rate of 1 ml per minute.

In yet another embodiment of the compounds of the present invention, the compound is radiolabelled, such as with carbon-14, or tritiated. Said radiolabelled or tritiated compounds are useful as reference standards for in vitro assays to identify new PPARα and PPARγ agonists.

SYNTHESIS

Compounds of the present invention have been formed by reacting a 2-(R1-substituted)-5-R2-substituted-oxazol-4-yl ethyl sulfonyl ester with a 3-(4-hydroxyphenyl)-2-R4-oxy-propionic acid or a 3-(5-hydroxy-thiophen-2,5-diyl)-2-R4-oxy-propionic acid. Generally, the sulfonyl ester chemical intermediates have been synthesized through two different routes, shown in Schemes IA and IB, while Scheme II is typical of the synthethic method used to make the propionic acid chemical intermediate. The formation of the compounds of the present invention from these chemical intermediates is shown in Scheme III.

In Scheme IA, the first step is a condensation of a dionemonooxime represented by Structural Formula IA-1 with a R1-substituted aldehyde represented by Structural Formula IA-2 in the presence of an acid such as aqueous concentrated hydrochloric acid or, preferably, acetic acid which is saturated with hydrogen chloride gas. Typically, hydrogen chloride is bubbled through a solution of the dionemonooxime and the R1-substituted aldehyde in acetic acid, which is held at a constant temperature of about 0° C. to about 20° C. for about 15 minutes to about 1 hour. The product of the condensation is an oxazole n-oxide represented by Structural Formula IA-3.

The oxazole n-oxide is then treated with phosphorous oxyhalide, such as phosphorous oxychloride or phosphorous oxybromide in an inert solvent such as dichloromethane or chloroform to form a 2-(R1-substituted)-4-halomethyl-oxazole represented by Structural Formula IA-4. The reaction typically is carried out at the reflux temperature of the solvent used and is complete in about 15 minutes to about 1 hour.

The 2-(R1-substituted)-4-chloromethyl-oxazole is then treated with a cyanide and an iodide salt to form a 2-(R1-substituted)-4-cyanomethyl-oxazole represented by Structural Formula IA-5. The reaction is typically carried out in a polar, aprotic solvent such as dimethylformamide at a temperature of about 30° C. to about 120° C. for about 1 hour to about 6 hours. Preferably, the cyanide and iodide salts are potassium cyanide and potassium iodide.

The cyano group of the a 2-(R1-substituted)-4-cyanomethyl-oxazole is converted to a carboxylic acid group by treatment with a alkali metal hydroxide to form a 2-(R1-substituted)-4-carboxymethyl-oxazole represented by Structural Formula IA-6. The reaction is generally carried out in an aqueous solution at about 80° C. to about 100° C. The concentration of the alkali metal hydroxide in the aqueous solution is typically about 25% to about 85% (weight/volume). Preferably, the alkali metal hydroxide is potassium hydroxide.

The 2-(R1-substituted)-4-carboxymethyl-oxazole is then treated with a carboxylic acid reducing agent, such as borane or lithium aluminum hydride, to form the 2-(R1-substituted)-4-(2-hydroxyethyl)-oxazole intermediate represented by Structural Formula IA-7. The reaction is typically carried out under anhydrous conditions in an ether solvent such as tetrahydrofuran (THF), dioxane, or ethyl ether. When borane is the reducing agent used, it typically forms a complex with the ether solvent such as a $BH_3$-THF complex. A solution having a concentration of about 0.5 M to about 1.5 M borane complex in the ether solvent is added dropwise to a solution of 0.1 M to 1.3 M of the 2-(R1-substituted)-4-carboxymethyl-oxazole in the ether solvent. The reaction temperature is about 20° C. to about 40° C. Typically, the reaction is complete in about 1 hour to about 5 hours.

The chemical intermediate, represented by Structural Formula IA-7, is then converted into a 2-(R1-substituted-oxazol-4-yl)ethyl sulfonyl ester represented by Structural Formula IA-8 by treatment with a sulfonyl anhydride, such as tosyl anhydride or mesyl anhydride, or a sulfonyl halide, such as tosyl chloride or mesyl chloride, in the presence of a base. The reaction is typically carried out in an aprotic solvent such as methylene chloride in the presence of an aprotic base such as pyridine or N,N-dimethylaminopyridine (DMAP). The reaction is complete in about 0.5 hours to about 5 hours.

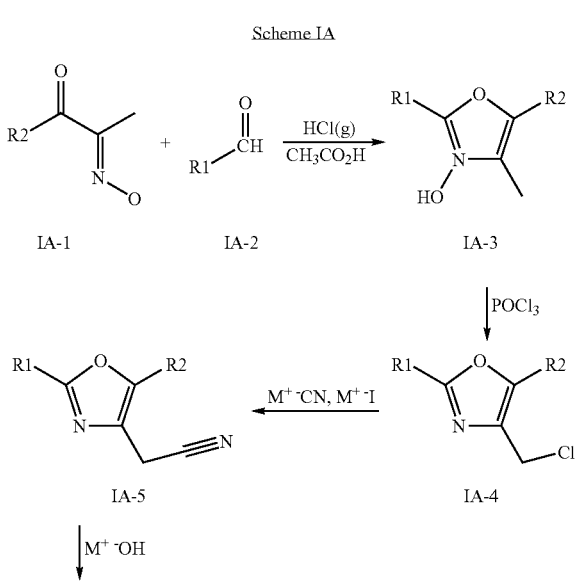

Scheme IA

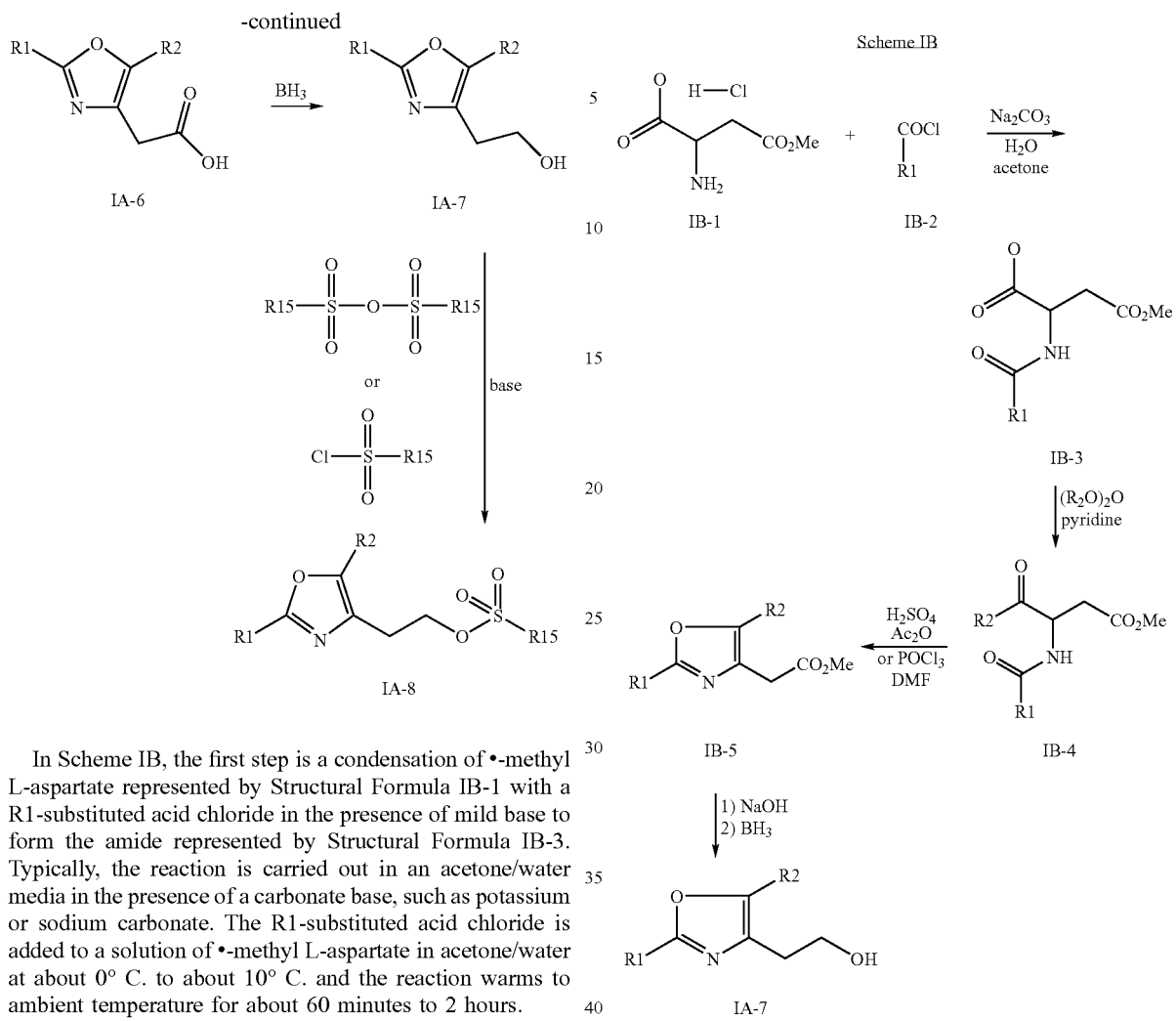

In Scheme IB, the first step is a condensation of •-methyl L-aspartate represented by Structural Formula IB-1 with a R1-substituted acid chloride in the presence of mild base to form the amide represented by Structural Formula IB-3. Typically, the reaction is carried out in an acetone/water media in the presence of a carbonate base, such as potassium or sodium carbonate. The R1-substituted acid chloride is added to a solution of •-methyl L-aspartate in acetone/water at about 0° C. to about 10° C. and the reaction warms to ambient temperature for about 60 minutes to 2 hours.

The acid is then treated with a base such as pyridine and an anhydride such as acetic, n-propyl or trifluoroacetic anhydride to form the R2-substituted ketone represented by Structural Formula IB-4. The reaction is typically carried out at 90° C. and is complete in about 90 minutes to about 2 hours.

Cyclo-dehydration of the R2-substituted ketone is completed with a protic acid such as sulfuric acid in the presence of acetic anhydride to form the 2-(R1-substituted)-5-(R2-substituted)-oxazole represented by Structural Formula IB-5. Alternatively, the ketone can be treated with a phosphorus oxyhalide, such as phosphorous oxychloride or phosphorous oxybromide in a polar, aprotic solvent such as dimethylformamide. In both methods, the reaction is heated to about 90° C. and is complete in about 15 minutes to 30 minutes.

The 2-(R1-substituted)-5-(R2-substituted)-oxazole is treated with aqueous base, such as aqueous sodium hydroxide in an alcohol solvent at about 25° C. to about 45° C. for about 30 minutes to form the corresponding acid. The acid is treated with a carboxylic acid reducing agent, such as borane or lithium aluminum hydride, to form the 2-(R1-substituted)-4-(2-hydroxyethyl)-oxazole intermediate represented by Structural Formula IA-7. The reaction is typically carried out as described for the formation of the intermediate represented by Structural Formula IA-7 in Scheme IA.

The compound represented by Structural Formula II-7 can be prepared by the method depicted in Scheme II. In this method, an α-bromoester represented by compound II-1 is reacted with a phenol represented by compound II-2 to form an α-phenoxy ester represented by compound II-3. This reaction is typically carried out in an anhydrous polar solvent such as DMF at a temperature of about 60° C. to about 110° C. The reaction time is about 10 h to about 20 h.

The α-phenoxy ester is then deprotonated with an alkylamide lithium compound, such as LDA (1.1 eq), to form the enol. This reaction is typically performed in an anhydrous, polar, aprotic solvent at a temperature of about −20° C. to about −110° C. After about 5 min to about 20 min. a 4-benzyloxybenzaldehyde represented by compound II-4 is added and the reaction is stirred for about 5 min. to about 30 min., then quenched with an aqueous solution of ammonium chloride to form a 3-(4-benzyloxyphenyl)-3-hydroxy-2-substituted-2-phenoxy-propanoic ester represented by Structure II-5.

A solution of 3-(4-benzyloxyphenyl)-3-hydroxy-2-substituted-2-phenoxy-propanoic ester in an anhydrous aprotic solvent at a temperature of about −10° C. to about 10° C. was treated with an ether complex of boron trifluoride and triethylsilane. The reaction is gradually allowed to warm to room temperature then stirred for about 1 h to about 2.5 h.

The mixture is quenched by adding an aqueous base to form 3-(4-benzyloxyphenyl)-2-substituted-2-phenoxy-propanoic ester represented by Structural Formula II-6.

The compound represented by Structural Formula II-6 is then treated to remove the benzyl protecting group to form the phenol represented by Structural Formula II-7. Methods of removing a benzyl protecting group from a phenol can be found in Green, et al., *Protective Groups in Organic Synthesis*, 2$^{nd}$ edition, (1991), John Wiley & Sons, Inc., New York, pages 156-158, the entire teachings of which are incorporated herein by reference. A preferred method of removing a benzyl protecting group is by treating the compound represented by Structural Formula II-3 with hydrogen in the presence of palladium on carbon (Pd—C) catalyst.

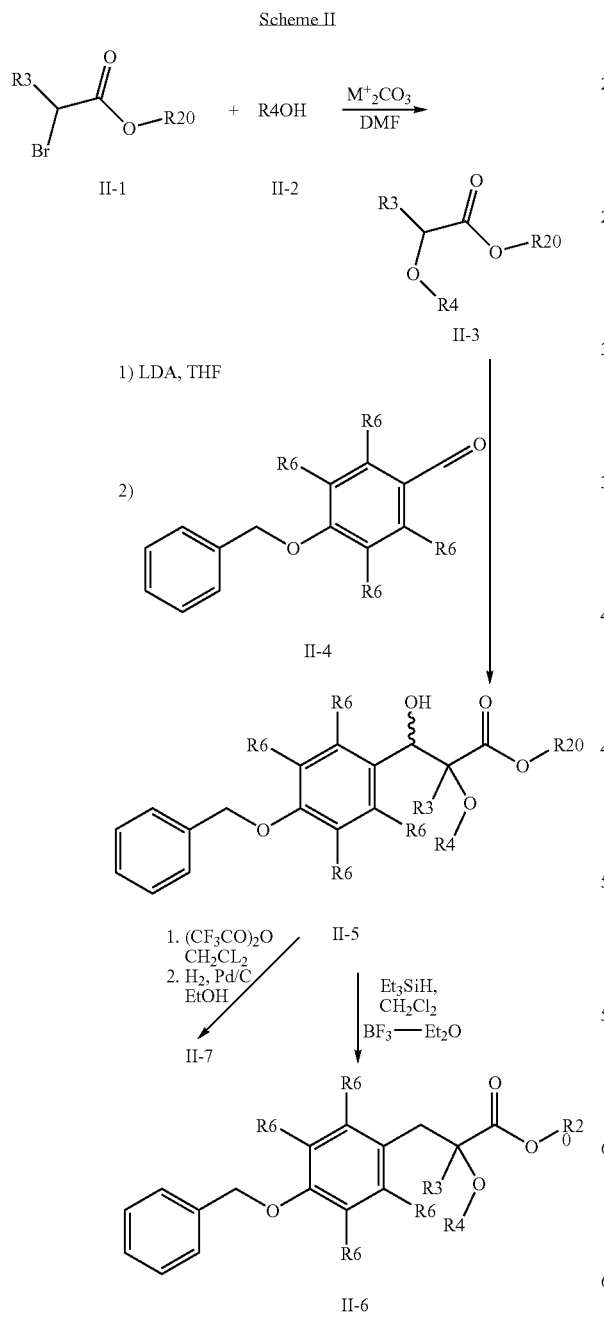

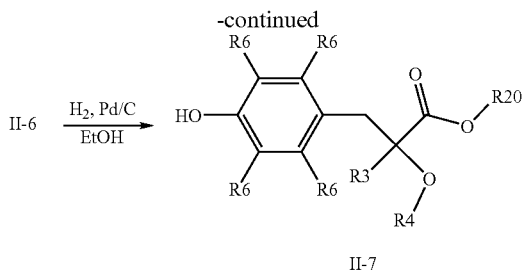

In Scheme III, the 2-(oxazol-4-yl)ethyl sulfonyl ester is then reacted with a phenol represented by Structural Formula II-7 in the presence of a metal carbonate, such as cesium carbonate, to form a 2-(3-{2-[2-oxazol-4-yl]ethoxy}-2-phenoxy)-alkanoic acid ester represented by Structural Formula III-1. In Structural Formula II-7, R3, R4 and R6 are as previously defined while R20 is a C1-C4 alkyl. The reaction is typically carried out in a polar, aprotic solvent such as dimethylformamide at about 40° C. to about 70° C. and is allowed to proceed for about 10 hours to about 24 hours. The reactants (i.e., the compounds represented by Structural Formulas IA-8 and II-7) are present in about equal molar amounts or with about 0.1 M to about 0.5 M excess of the sulfonyl ester compound represented by Structural Formula IA-8. The cesium carbonate is present in about one molar equivalent to about 1.5 molar equivalents with respect to the sulfonyl ester.

Alternatively, the 2-(oxazol-4-yl)ethyl sulfonyl ester is reacted with a phenol represented by Structural Formula II-7 in the presence of a hindered base to form a 3-(4-{2-[2-oxazol-4-yl]ethoxy}-phenyl)-2-methyl-2-phenoxy-propanoic acid ester represented by Structural Formula III-1. The reaction is typically carried out in a polar solvent such as an alcohol at about 40° C. to about 70° C. and is allowed to proceed for about 24 hours to about 48 hours. The reactants (i.e., the compounds represented by Structural Formulas IA-8 and II-7) are present in about equal molar amounts. The alkaline metal carbonate is present in about 20 molar equivalents and is preferably bound to an inert solid support such as polystyrene.

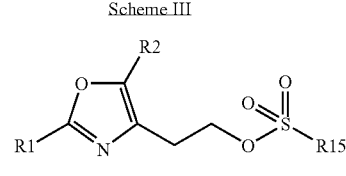

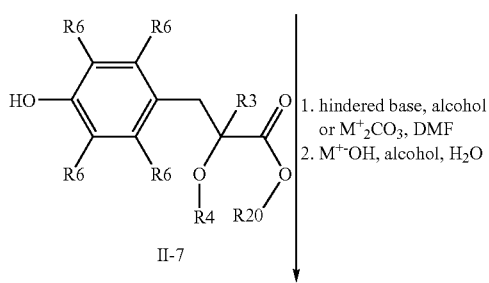

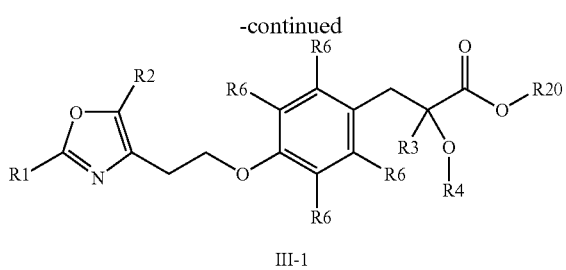

III-1

Hydrolysis of the 2-(3-{2-[2-oxazol-4-yl]ethoxy}-2-phenoxy)-alkanoic acid ester, represented by Structural Formula III-1 wherein R20 is a C1-C4 alkyl, is typically carried out in an alcohol solvent in the presence of an excess of aqueous alkali metal hydroxide. The reaction is heated at about 50° C. to about 60° C. and is allowed to proceed for about 10 hours to about 24 hours to form a 2-(3-{2-[2-oxazol-4-yl]ethoxy}-2-phenoxy)-alkanoic acid represented by Structural Formula III-1 wherein R20 is H.

EXEMPLIFICATION

Instrumental Analysis

Infrared spectra were recorded on a Perkin Elmer 781 spectrometer. $^1$H NMR spectra were recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR were recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses were performed by Eli Lilly & Company Microanalytical Laboratory. High resolution mass spectra were obtained on VG ZAB 3F or VG 70 SE spectrometers. Analytical thin layer chromatography was performed on EM Reagent 0.25 mm silica gel 60-F plates. Visualization was accomplished with UV light.

Standard Synthesis Procedures

Certain standard synthesis procedures were used in preparing many of the exemplified compounds of the present invention. These standard procedures were:

Standard Procedure (A): Toluene-4-sulfonic acid 2-(2-phenyl-5-methyl-oxazol-4-yl)-ethyl ester (0.47 g, 0.132 mmol) was added to a one dram, screw-cap vial and diluted with ethanol (0.5 mL). To this solution are added 3-(4-hydroxyphenyl)-2-methyl-2-phenoxypropionic acid ethyl ester (0.5 mL of a 0.264 M solution in ethanol, 0.132 mmol) and polystyrene bound 1,5,7-triazabicyclo[4.4.0]dec-5-ene (100-125 mg, 2.6 mmol/g) and the vial was tightly closed. The reaction vessel was heated in a block heater for 24-48 h at 55° C., or until TLC or MS analysis indicates the disappearance of starting materials. The suspension was filtered while warm and the residue washed with ethanol (1 mL). The solution was treated with aqueous NaOH (5N solution, 100 μl) and the vial resealed tightly. The solution was heated in a block heater at 55° C. for 3-16 h, or until MS analysis indicates the completion of the hydrolysis. The solvents are removed with a stream of nitrogen or under reduced pressure and the residue redissolved in 1 mL water. The solution was acidified with aqueous HCl (5N solution, 150 μl), often causing precipitation of product. The suspension was diluted with dichloromethane (3 mL) and the resultant biphasic solution was filtered through a Chrom-Elut column to remove water. The filtrate was concentrated in vacuo and the resultant residue was purified by mass-directed HPLC to provide analytically pure material. Overall yield after purification 25%.

Standard Procedure (B): A mixture of 3-(4-hydroxyphenyl)-2-methyl-2-m-tolyloxy-propionic acid ethyl ester (0.095 g, 0.030 mmol), toluene-4-sulfonic acid 2-(5-methyl-2-phenyl-oxazol-4-yl)-ethyl ester (0.108 g, 0.030 mmol) and 325 mesh K$_2$CO$_3$ (0.084 g, 0.60 mmol) in ethanol (2 mL) was heated to reflux for 24 h under N$_2$. Aqueous 5N NaOH (0.5 mL) and additional ethanol (1 mL) was added to the reaction mixture and it was heated at reflux for an additional 2 h. The reaction was cooled and the solvent removed in vacuo. The residue was acidified with aqueous 1 N HCl (5 mL), extracted with water and CH$_2$Cl$_2$ and the organic layer dried by passing it through a Varian Chem Elut 1003 cartridge. The solvent was removed in vacuo to give 0.134 g of crude product which was purified by LCMS to give 0.036 g (25%) of analytically pure 2-methyl-3-{4-[2-(5-methyl-2-phenyl-oxazol-4-yl)-ethoxy]-phenyl}-2-m-tolyloxy-propionic acid.

Exemplified Compounds

Example 1 rac-3-{4-[2-(2-Phenyl-5-methyl-oxazol-4-yl)-ethoxy]-phenyl}-2-methyl-2-phenoxy-propionic acid

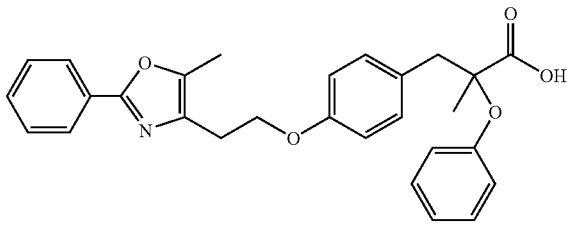

The title compound, shown above, was made as described below.

Step A

2-Phenoxypropionic acid ethyl ester

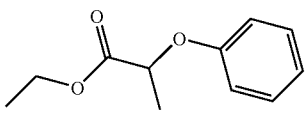

Phenol (28.5 g, 0.30 mol), Cs$_2$CO$_3$ (197.0 g, 0.61 mol), and ethyl 2-bromopropionate (54.3 g, 0.30 mol) were combined in anhydrous N,N-dimethylformamide (DMF) (1000 mL) and stirred at 90° C. under an atmosphere of nitrogen. After 16 h, the DMF was removed in vacuo. The residue was dissolved in ethyl acetate (300 mL) and washed twice with water and once with brine. The organic layer was dried over Na$_2$SO$_4$ and concentrated in vacuo to produce 2-phenoxypropionic acid ethyl ester, shown above, as a golden oil (48.5 g, 83%) $^1$H NMR (250 MHz, CDCl$_3$): δ 7.31 (d, 2H, J=7.8), 7.02 (t, 1H, J=7.9), 6.93 (d, 2H, J=7.8), 4.79 (q, 1H, J=6.1), 4.26 (q, 2H, J=7.2), 1.66 (d, 3H, J=6.1), 1.24 (t, 3H, J=7.2). MS [EI+] 195 (M+H)$^+$ Step B 2-Phenoxy-3-(4-benzyloxyphenyl)-2-methyl-propionic acid ethyl ester

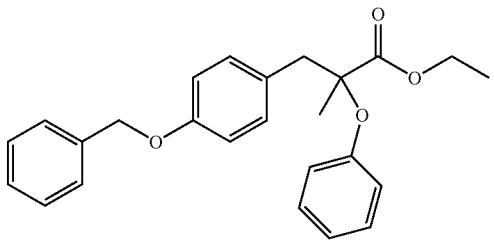

A solution of lithium diisopropylamide (LDA) (16.5 mL, 24.7 mmol, 1.5M in cyclohexane) was cooled to −78° C. in a dry ice/acetone bath and then added to a solution of 3-(4-hydroxyphenyl)-2-methyl-2-phenoxypropionic acid ethyl ester (4.79 g, 24.7 mmol) in anhydrous tetrahydrofuran (THF) (30 mL) also cooled to −78° C. under an atmosphere of nitrogen. After 5 min, 4-benzyloxybenzaldehyde (4.76 g, 22.4 mmol) was added in one portion. After stirring for 10 min, the reaction mixture was quenched with saturated solution of aqueous NH$_4$Cl (10 m L) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0-20% ethyl acetate in hexanes) to provide a colorless oil (3.84 g, 42%) as a mixture of inseparable diastereomers of 2-phenoxy-3-(4-benzyloxyphenyl)-3-hydroxy-2-methylpropionic acid ethyl ester which was used without further characterization or purification. R$_f$=0.32 in 4:1 hexanes:ethyl acetate.

2-Phenoxy-3-(4-benzyloxyphenyl)-3-hydroxy-2-methyl-propionic acid ethyl ester (3.84 g, 9.5 mmol) in anhydrous CH$_2$Cl$_2$ (30 mL) was cooled to 0° C. and treated with BF$_3$-Et$_2$O (1.16 mL, 9.5 mmol) and triethylsilane (1.51 mL, 9.5 mmol). The mixture was stirred for 2 h and gradually warmed to ambient temperature. Saturated aqueous Na$_2$CO$_3$ (15 mL) was added and the mixture was stirred vigorously. The solution was partitioned and the organic layer was washed twice with water and brine, dried over Na$_2$SO$_4$, and concentrated in vacuo to produce 2-phenoxy-3-(4-benzyloxyphenyl)-2-methyl-propionic acid ethyl ester, shown above, as a colorless oil (1.34 g, 36%). R$_f$=0.90 (9:1 hexanes:ethyl acetate). $^1$H NMR (300 MHz, CDCl$_3$): δ 7.36-7.42 (m, 3H), 7.34 (t, 1H), 7.17-7.24 (m, 5H), 6.98 (t, 1H), 6.91 (d, 2H), 6.83 (d, 2H), 5.05 (s, 2H), 4.22 (q, 1H, J=7.1), 3.26 (d, 1H, J=13.7), 3.13 (d, 1H, J=13.7), 1.40 (s, 3H), 1.22 (t, 3H, J=7.1). MS [EI+] 408 (M+NH$_4$)$^+$.

Step C 3-(4-Hydroxyphenyl)-2-methyl-2-phenoxypropionic acid ethyl ester

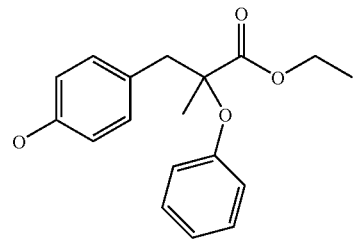

2-Phenoxy-3-(4-benzyloxyphenyl)-2-methyl-propionic acid ethyl ester (830 mg, 2.1 mmol) was dissolved in ethyl acetate (30 mL) and treated with 5% palladium on carbon (300 mg), and then stirred under an atmosphere of hydrogen for 20 h. The suspension was filtered through celite and concentrated in vacuo to produce 3-(4-hydroxyphenyl)-2-methyl-2-phenoxypropionic acid ethyl ester colorless oil (563 mg, 89%) $^1$H NMR (300 MHz, CDCl$_3$): δ 7.23 (t, 2H), 7.13 (d, 2H), 6.96 (t, 1H), 6.83 (d, 2H), 6.76 (d, 2H), 4.19 (q, 1H, J=7.1), 3.23 (d, 1H, J=12.4), 3.08 (d, 1H, J=12.4), 1.39 (s, 3H), 1.22 (t, J=7.1). MS [EI+] 318 (M+H)$^+$, [EI−] 359 (M+OAc$^-$).

Additional 3-(4-hydroxyphenyl)-2-methyl-2-phenoxypropionic acid ethyl ester (approx 48 g), prepared in the same manner, was purified by chiral chromatography to provided the individual enantiomers (Chiralcel OD, 8×27 cm, 7% IPA/heptane, 248 nm; (S)-isomer: 97.2% ee; (R)-isomer: >99% ee).

Step D

3-{4-[2-(2-Phenyl-5-methyl-oxazol-4-yl)-ethoxy]-phenyl}-2-methyl-2-phenoxy-propionic acid ethyl ester

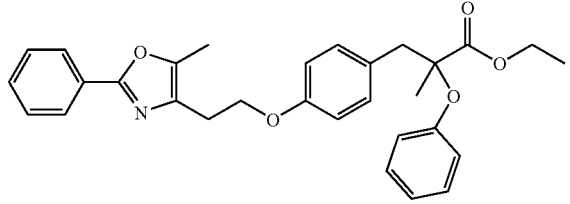

3-(4-Hydroxyphenyl)-2-methyl-2-phenoxypropionic acid ethyl ester (495 mg, 1.7 mmol), toluene-4-sulfonic acid 2-(2-phenyl-5-methyl-oxazol-4-yl)-ethyl ester (766 mg, 2.2 mmol) and Cs$_2$CO$_3$ (700 mg, 2.2 mmol) were combined in anhydrous DMF (25 mL) and stirred for 16 h at 55° C. under an atmosphere of nitrogen. The mixture was then cooled and diluted with ethyl acetate (100 mL), and washed with water then brine. The organic layer was dried with Na$_2$SO$_4$ and concentrated in vacuo to a viscous yellow oil. The residue was purified by flash column chromatography (100 g silica, 60×15 mL fractions, gradient elution 0-20% ethyl acetate in hexanes) to provide the ethyl ester as a colorless oil (48%). $^1$H NMR (300 MHz, CDCl$_3$): δ 7.96 (m, 2H), 7.41 (m, 3H), 7.19 (t, 2H), 7.12 (d, 2H), 6.93 (t, 1H), 6.82 (m, 4H), 4.20 (q, 2H), 4.18 (t, 2H), 3.23 (d, 1H), 3.06 (d, 1H), 2.95 (t, 2H), 2.37 (s, 3H), 1.33 (s, 3H). MS [EI+] 486 (M+H)$^+$, [EI−] 484 (M−H)$^+$ Step E 3-{4-[2-(2-Phenyl-5-methyl-oxazol-4-yl)-ethoxy]-phenyl}-2 methyl-2-phenoxy-propionic acid The title compound, was prepared as follows. 3-{4-[2-(2-Phenyl-5-methyl-oxazol-4-yl)ethoxy]-phenyl}-2-methyl-2-phenoxypropionic acid ethyl ester (4.6 g, 9.5 mmol) was dissolved in methanol (75 ml) and treated with 2.0 N NaOH (75 ml) with vigorous stirring, causing slight precipitation. The suspension was heated for 18 h at 55 C, allowing full dissolution of all reagents. The methanol was then removed in vacuo and the aqueous residue was acidified with 5.0 N HCl (75 ml) at 0° C. The suspension was extracted into ethyl acetate and the orgnaic solution dried over Na$_2$SO$_4$ and concentrated to produce a white solid (94%).

$^1$H NMR (300 MHz, d$_6$-DMSO): δ 7.87 (m, 2H), 7.44 (m, 3H), 7.21 (dd, 2H, J=7.8, 8.8), 7.10 (d, 2H, J=8.8), 6.91 (t, 1H, J=8.8), 6.81(d, 2H, J=7.8), 6.77 (d, 2H, J=7.8), 4.14 (t, 2H, J=6.6), 3.14 d, 1H, J=12.0), 3.01 (d, 1H, J=12.0), 2.88 (d, 2H, J=6.6), 2.31 (s, 3H), 1.24 (s, 3H). MS [EI+]458 (M+H)$^+$, 480 (M+Na)$^+$, [EI−] 456 (M−H)$^+$

Example 2

(R)-3-{4-[2-(2-Phenyl-5-methyl-oxazol-4-yl)-ethoxy]-phenyl}-2-methyl-2-phenoxy-propionic acid

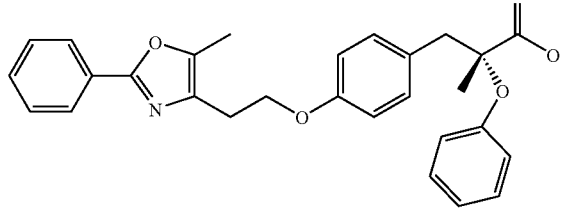

(R)-3-(4-hydroxyphenyl)-2-methyl-2-phenoxypropionic acid ethyl ester, shown below,

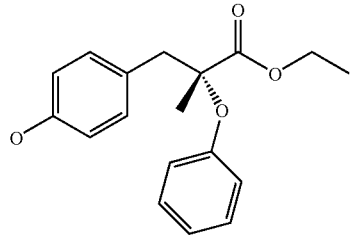

from Example 1, Step C, and toluene-4-sulfonic acid 2-(2-phenyl-5-methyloxazol-4-yl)-ethyl ester were reacted, as described in Example 1, Step D, to provide (R)-3-{4-[2-(2-phenyl-5-methyl-oxazol-4-yl)-ethoxy]-phenyl}-2-methyl-2-phenoxypropionic acid ethyl ester, shown below, as a colorless oil (61%). $^1$H NMR (300 MHz, CDCl$_3$): δ 7.96 (m, 2H), 7.41 (m, 3H), 7.19 (t, 2H), 7.12 (d, 2H), 6.93 (t, 1H), 6.82 (m, 4H), 4.20 (q, 2H), 4.18 (t, 2H), 3.23 (d, 1H), 3.06 (d, 1H), 2.95 (t, 2H), 2.37 (s, 3H), 1.33 (s, 3H). MS [EI+] 486 (M+H)$^+$, [EI−] 484 (M−H)$^+$.

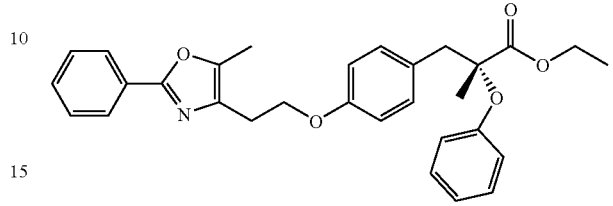

The title compound was then prepared from this phenoxy propionic acid ethyl ester, via the hydrolysis procedure of Example 1, Step E, to produce a white solid (99%). $^1$H NMR (300 MHz, d$_6$-DMSO): δ 7.87 (m, 2H), 7.44 (m, 3H), 7.21 (dd, 2H, J=7.8, 8.8), 7.10 (d, 2H, J=8.8), 6.91 (t, 1H, J=8.8), 6.81 (d, 2H, J=7.8), 6.77 (d, 2H, J=7.8), 4.14 (t, 2H, J=6.6), 3.14 d, 1H, J=12.0), 3.01 (d, 1H, J=12.0), 2.88 (d, 2H, J=6.6), 2.31 (s, 3H), 1.24 (s, 3H). MS [EI+] 458 (M+H)$^+$, [EI−] 456 (M−H)$^+$.

Example 3

(S)-3-{4-[2-(2-Phenyl-5-methyl-oxazol-4-yl)-ethoxy]-phenyl}-2-methyl-2-phenoxy-propionic acid

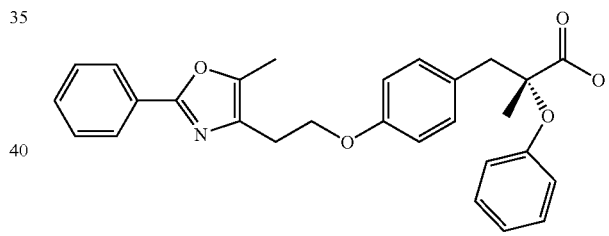

(S)-3-(4-hydroxyphenyl)-2-methyl-2-phenoxypropionic acid ethyl ester, shown below,

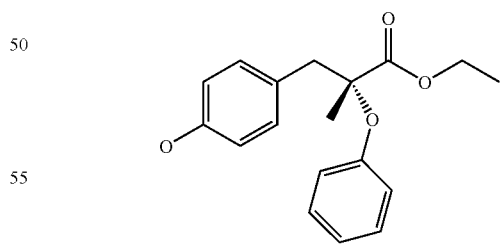

from Example 1, Step C, and toluene-4-sulfonic acid 2-(2-phenyl-5-methyloxazol-4-yl)-ethyl ester were reacted, as described in Example 1, Step D, to provide (S)-3-{4-[2-(2-phenyl-5-methyl-oxazol-4-yl)-ethoxy]-phenyl}-2-methyl-2-phenoxypropionic acid ethyl ester, shown below, as a colorless oil (41%). $^1$H NMR (300 MHz, CDCl$_3$): δ 7.96 (m, 2H), 7.41 (m, 3H), 7.19 (t, 2H), 7.12 (d, 2H), 6.93 (t, 1H), 6.82 (m, 4H), 4.20 (q, 2H), 4.18 (t, 2H), 3.23 (d, 1H), 3.06

(d, 1H), 2.95 (t, 2H), 2.37 (s, 3H), 1.33 (s, 3H). MS [EI+] 486 (M+H)⁺, [EI−] 484 (M−H)⁺.

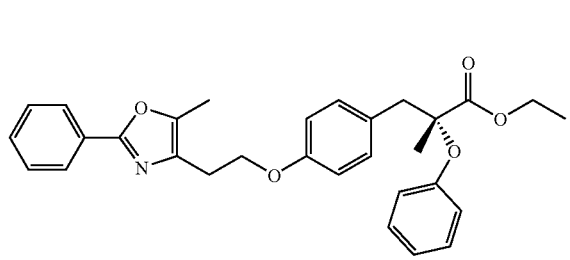

The title compound was then prepared from this phenoxy propionic acid ethyl ester, via the hydrolysis procedure of Example 1, Step E, to produce a white solid (96%). ¹H NMR (300 MHz, d₆-DMSO): δ 7.87 (m, 2H), 7.44 (m, 3H), 7.21 (dd, 2H, J=7.8, 8.8), 7.10 (d, 2H, J=8.8), 6.91 (t, 1H, J=8.8), 6.81 (d, 2H, J=7.8), 6.77 (d, 2H, J=7.8), 4.14 (t, 2H, J=6.6), 3.14 d, 1H, J=12.0), 3.01 (d, 1H, J=12.0), 2.88 (d, 2H, J=6.6), 2.31 (s, 3H), 1.24 (s, 3H). MS [EI+] 458 (M+H)⁺, [EI−] 456 (M−H)⁺.

Example 4 rac-2-Methyl-3-{4-[2-(5-methyl-2-thiophen-2-yl-oxazol-4-yl)-ethoxy]-phenyl}-2-phenoxypropionic acid

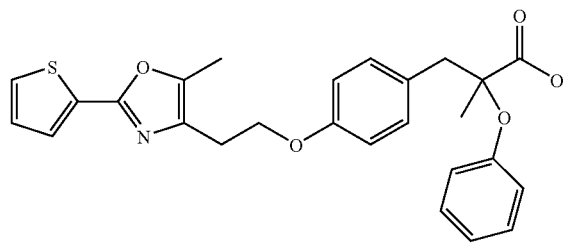

3-(4-Hydroxyphenyl)-2-methyl-2-phenoxypropionic acid ethyl ester and toluene-4-sulfonic acid 2-(5-methyl-2-thiophen-2-yl-oxazol-4-yl)-ethyl ester, shown below,

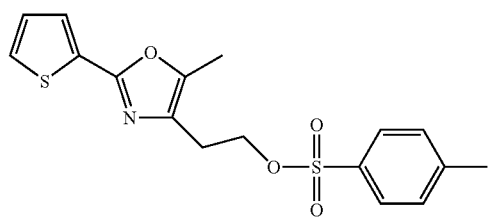

were reacted, as described in Example 1, Step D, to provide 2-methyl-3-{4-[2-(5-methyl-2-thiophen-2-yl-oxazol-4-yl)-ethoxy]-phenyl}-2-phenoxypropionic acid ethyl ester, shown below, as a colorless oil (30%). ¹H NMR (300 MHz, CDCl₃): δ 7.59 (d, 1H), 7.37 (d, 1H), 7.24 (t, 2H), 7.13, (d, 2H), 7.09 (t, 1H), 6.96 (t, 1H), 6.83 (d, 2H), 6.82 (d, 2H), 4.21 (t, 2H), 4.19 (q, 2H), 3.26 (d, 1H), 3.12 (d, 1H), 2.95 (t, 2H), 2.35 (s, 3H), 1.39 (s, 3H), 1.21 (t, 3H). MS [EI+] 492 (M+H)⁺, [EI−] 490 (M−H)⁺.

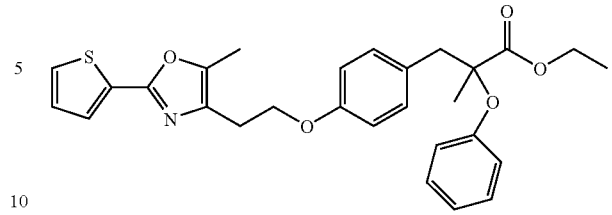

The title compound was then prepared from this phenoxy propionic acid ethyl ester, using the hydrolysis procedure of Example 1, Step E, to provide a white solid (88%). ¹H NMR (300 MHz, d₆-DMSO): δ 7.70 (d, 1H, J=5.1), 7.57 (d, 1H, J=3.5), 7.23 (t, 2H, J=7.4), 7.15 (dd, 1H, J=3.5, 5.1), 7.12 (d, 2H, J=8.6), 6.93 (dd, 1H, J=7.4, 7.8), 6.83 (d, 2H, J=8.6), 6.79 (d, 2H, J=7.8), 4.14 (t, 2H, J=6.6), 3.15 (d, 1H, J=13.7), 3.03 (d, 1H, J=13.7), 2.87 (t, 2H, J=6.6), 2.30 (s, 3H), 1.26 (s, 3H). MS [EI+] 464 (M+H)⁺, [EI−] 462 (M−H)⁺ HPLC: T=2.78 min, purity 99%.

Example 5

(R)-2-Methyl-3-{4-[2-(5-methyl-2-thiophen-2-yl-oxazol-4-yl)-ethoxy]-phenyl}-2-phenoxypropionic acid

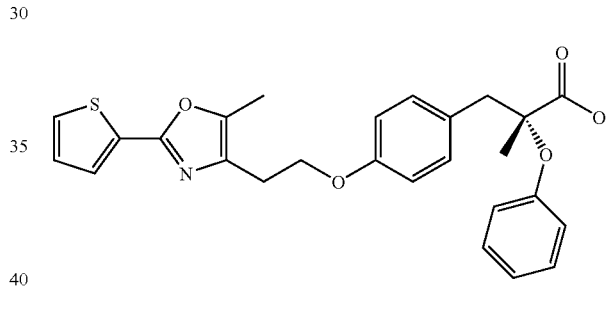

(R)-3-(4-Hydroxyphenyl)-2-methyl-2-phenoxypropionic acid ethyl ester and toluene-4-sulfonic acid 2-(5-methyl-2-thiophen-2-yl-oxazol-4-yl)-ethyl ester were reacted, as described in Example 1, Step D, to provide (R)-2-methyl-3-{4-[2-(5-methyl-2-thiophen-2-yl-oxazol-4-yl)-ethoxy]-phenyl}-2-phenoxypropionic acid ethyl ester, shown below, as a colorless oil (54%). ¹H NMR (300 MHz, CDCl₃): δ 7.59 (d, 1H), 7.37 (d, 1H), 7.24 (t, 2H), 7.13, (d, 2H), 7.09 (t, 1H), 6.96 (t, 1H), 6.83 (d, 2H), 6.82 (d, 2H), 4.21 (t, 2H), 4.19 (q, 2H), 3.26 (d, 1H), 3.12 (d, 1H), 2.95 (t, 2H), 2.35 (s, 3H), 1.39 (s, 3H), 1.21 (t, 3H). MS [EI+] 492 (M+H)⁺, [EI−] 490 (M−H)⁺.

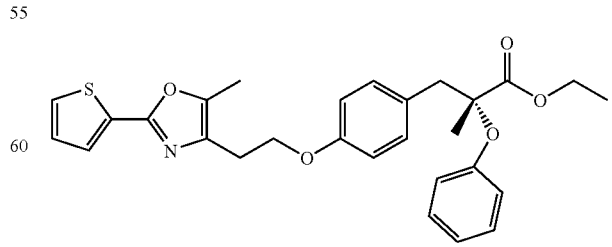

The title compound was then prepared using the hydrolysis procedure of Example 1, Step E, to provide a white solid (78%). ¹H NMR (300 MHz, d₆-DMSO): • 7.70 (d, 1H, J=5.1), 7.57 (d, 1H, J=3.5), 7.23 (t, 2H, J=7.4), 7.15 (dd, 1H, J=3.5, 5.1), 7.12 (d, 2H, J=8.6), 6.93 (dd, 1H, J=7.4, 7.8), 6.83 (d, 2H, J=8.6), 6.79 (d, 2H, J=7.8), 4.14 (t, 2H, J=6.6), 3.15 (d, 1H, J=13.7), 3.03 (d, 1H, J=13.7), 2.87 (t, 2H, J=6.6), 2.30 (s, 3H), 1.26 (s, 3H). MS [EI+] 464 (M+H)⁺, [EI−] 462 (M−H)⁺.

Example 6

(S)-2-Methyl-3-{4-[2-(5-methyl-2-thiophen-2-yl-oxazol-4-yl)-ethoxy]-phenyl}-2-phenoxypropionic acid

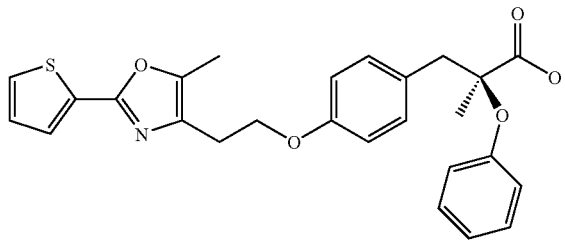

(S)-3-(4-hydroxyphenyl)-2-methyl-2-phenoxypropionic acid ethyl ester and toluene-4-sulfonic acid 2-(5-methyl-2-thiophen-2-yl-oxazol-4-yl)-ethyl ester were reacted, as described in Example 1, Step D, to provide (S)-2-methyl-3-{4-[2-(5-methyl-2-thiophen-2-yl-oxazol-4-yl)-ethoxy]-phenyl}-2-phenoxypropionic acid ethyl ester, shown below, as a colorless oil (48%). ¹H NMR (300 MHz, CDCl₃): δ 7.59 (d, 1H), 7.37 (d, 1H), 7.24 (t, 2H), 7.13, (d, 2H), 7.09 (t, 1H), 6.96 (t, 1H), 6.83 (d, 2H), 6.82 (d, 2H), 4.21 (t, 2H), 4.19 (q, 2H), 3.26 (d, 1H), 3.12 (d, 1H), 2.95 (t, 2H), 2.35 (s, 3H), 1.39 (s, 3H), 1.21 (t, 3H). MS [EI+] 492 (M+H)⁺, [EI−] 490 (M−H)⁺.

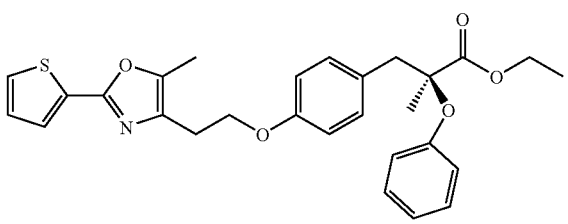

The title compound was then prepared using the hydrolysis procedure of Example 1, Step E, to provide a white solid (78%). ¹H NMR (300 MHz, d₆-DMSO): δ 7.70 (d, 1H, J=5.1), 7.57 (d, 1H, J=3.5), 7.23 (t, 2H, J=7.4), 7.15 (dd, 1H, J=3.5, 5.1), 7.12 (d, 2H, J=8.6), 6.93 (dd, 1H, J=7.4, 7.8), 6.83 (d, 2H, J=8.6), 6.79 (d, 2H, J=7.8), 4.14 (t, 2H, J=6.6), 3.15 (d, 1H, J=13.7), 3.03 (d, 1H, J=13.7), 2.87 (t, 2H, J=6.6), 2.30 (s, 3H), 1.26 (s, 3H). MS [EI+] 464 (M+H)⁺, [EI−] 462 (M−H)⁺.

Example 7

2-Methyl-3-(4-{2-[5-methyl-2-cyclohexyl-oxazol-4-yl]-ethoxy}-phenyl)-2-phenoxypropionic acid

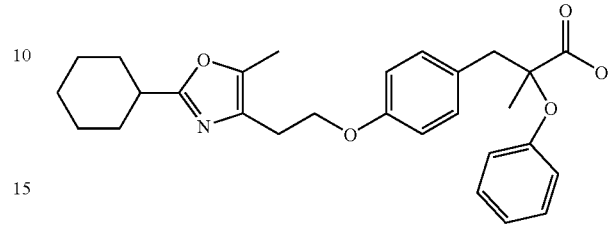

The title compound, shown above, was synthesized as follows:

Step A 2-(Cyclohexanecarbonyl-amino)-succinic acid 4-benzyl ester

Benzyl L-aspartate (25.0 g, 0.109 moles), DI water (325 mL), acetone (25 mL), and Na₂CO₃ (41.1 g, 0.384 mol) were combined and cooled to 8° C. Cyclohexanecarbonyl chloride (16 mL, 0.120 mol) was added dropwise via addition funnel over 10 min. The reaction was allowed to warm to ambient temperature and stirred for at least 90 min. Concentrated HCl (50 mL) was added to the slurry until the pH was ≦4.0 (pH paper). The mixture was stirred for an additional 45 min, and then filtered. The solid was rinsed with DI water (2×25 mL) and dried under vacuum at 30° C. overnight to provide 34.3 g of crude amide. Further purification was not necessary.

Step B 3-(Cyclohexanecarbonyl-amino)-4-oxo-pentanoic acid benzyl ester

In a 2 L flask, 2-(cyclohexanecarbonyl-amino)-succinic acid 4-benzyl ester (34.2 g, 0.102 moles), pyridine (155 mL) and acetic anhydride (127 mL) were combined. The reaction mixture was heated to 90° C. for 2 h and then cooled to ambient temperature. DI water (950 mL) was added slowly and the reaction mixture cooled to ambient temperature before adding conc. HCl (50 mL) to the slurry until the pH was ≦4.0 (pH paper). After stirring for 45 min, the solid was filtered, rinsed with DI water (2×50 mL) and then dried under vacuum at 40° C. overnight to obtain 26.0 g of crude ketone. Further purification was not necessary.

Step C (2-Cyclohexyl-5-methyl-oxazol-4-yl)-acetic acid benzyl ester

Phosphorous oxychloride (22 mL, 0.235 moles, 3.0 eq) was added dropwise to a solution of 3-(cyclohexanecarbonyl-amino)-4-oxo-pentanoic acid benzyl ester (26.0 g, 0.078 moles) in DMF (330 mL). The mixture was heated to 90° C. for 30 min, and then cooled to ambient temperature before diluting by slowly adding DI water (600 mL, Caution, exothermic). The mixture was cooled to ambient temperature and extracted with MTBE (3×150 mL). The combined organic phases were washed with DI water, brine (150 mL), dried over MgSO$_4$ and concentrated to obtain 21.1 g as a brown oil. Further purification was not necessary.

Step D (2-Cyclohexyl-5-methyl-oxazol-4-yl)-acetic acid (2-Cyclohexyl-5-methyl-oxazol-4-yl)-acetic acid benzyl ester (23.8 g, 0.076 moles), 2B-3 ethanol (120 mL), DI water (95 mL) and KOH (10.0 g, 0.152 moles, 2 eq) were stirred at ambient temperature for 60 min or until HPLC showed disappearance of benzyl ester. The reaction mixture was concentrated and then conc. HCL was added to the oily residue until the pH=1 (pH paper). The reaction mixture was partitioned with MTBE (100 mL) and then the organic layer was washed with DI water, brine (1×120 mL), dried over MgSO$_4$ and concentrated to obtain a brown semi-solid.

The brown semi-solid was dissolved in 5% Na$_2$CO$_3$ (100 mL) and washed with MTBE (3×100 mL). The combined organic phases were back-extracted with 5% Na$_2$CO$_3$ (1×50 mL). The combined aqueous layers were acidified to pH=1 with conc. HCl and extracted with MTBE (3×50 mL). The combined organic phases were washed with brine (1×50 mL), dried over MgSO$_4$ and concentrated to obtain 9.5 g of acid. The $^1$H NMR showed <1% benzyl alcohol.

Step E 2-(2-Cyclohexyl-5-methyl-oxazol-4-yl)-ethanol

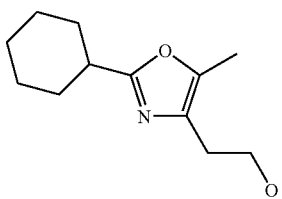

BH$_3$-THF complex (96 mL, 0.096 moles, 2.3 eq) was added dropwise via addition funnel to a solution of (2-cyclohexyl-5-methyl-oxazol-4-yl)-acetic acid (9.4 g, 0.041 moles) in THF (45 mL) over 50 min. The reaction mixture was stirred for 3 h, and then quenched with MeOH (30 mL). After heating at 60° C. for 2 h, the reaction mixture was cooled to ambient temperature, concentrated and the residue dissolved in CH$_2$Cl$_2$ (50 mL). The organic phase was washed with 1N NaOH and brine (1×50 mL), dried over MgSO$_4$ and concentrated to obtain 7.80 g of a yellow oil. The $^1$H NMR was consistent with desired product. $^1$H NMR (400 MHz, CDCl$_3$) δ3.73 (t, J=6.8 Hz, 2H), 2.58 (tt, J=11.6, 3.6 Hz, 1H), 2.54 (t, J=6.8 Hz, 2H), 2.13 (s, 3H), 1.93-1.89 (m, 2H), 1.74 (dt, J=12.8, 3.6 Hz, 2H), 1.67-1.62 (m, 1H), 1.41 (qd, J=12.0, 3.2 Hz, 1H), 1.33-1.17 (m, 4H); MS (EI+) 210.1 (M+H), 232.1 (M+H+Na).

Step F

Toluene-4-sulfonic acid 2-(2-cyclohexyl-5-methyl-oxazol-4-yl)-ethyl ester

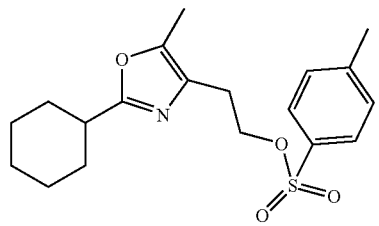

A solution of 2-(2-cyclohexyl-5-methyl-oxazol-4-yl)-ethanol, (8.7 g, 41.6 mmol) in CH$_2$Cl$_2$ (120 mL) at ambient temperature was treated with pyridine (12 mL, 150 mmol), 4-dimethylamino pyridine (DMAP) (1.6 g, 13.1 mmol), and tosyl anhyride (25.3 g, 77.5 mmol). After 18 h, the reaction mixture was partitioned with vigorous stirring between CH$_2$Cl$_2$ and 1N HCl. The aqueous layer was extracted with CH$_2$Cl$_2$ and then combined organic phases were washed with brine, dried (MgSO$_4$), filtered and concentrated. The residue was purified by Biotage chromatography (40 L, 25% EtOAc/hexanes) to provide the product (9.8 g, 65%): $^1$H NMR (400 MHz, CDCl$_3$) δ7.67 (d, J=8.4 Hz, 2H), 7.27 (d, J=8.4 Hz, 2H), 4.16 (t, J=6.8 Hz, 2H), 2.70 (t, J=6.8 Hz, 2H), 2.56 (tt, J=11.6, 3.6 Hz, 1H), 2.39 (s, 3H), 2.13 (s, 3H), 1.93-1.89 (m, 2H), 1.74 (dt, J=12.8, 3.6 Hz, 2H), 1.67-1.62 (m, 1H), 1.41 (qd, J=12.0, 3.2 Hz, 1H), 1.33-1.17 (m, 4H); MS (EI+) 364.1 (M+H).

Step G

2-Methyl-3-(4-{2-[5-methyl-2-cyclohexyl-oxazol-4-yl]-ethoxy}-phenyl)-2-phenoxypropionic acid ethyl ester

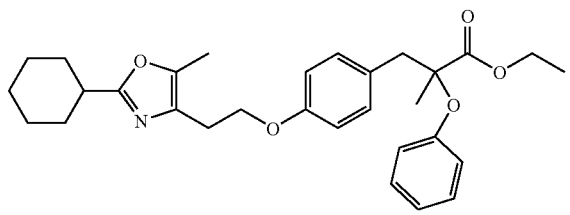

3-(4-Hydroxyphenyl)-2-methyl-2-phenoxypropionic acid ethyl ester (300 mg, 1.0 mmol), toluene-4-sulfonic acid 2-(2-cyclohexyl-5-methyl-oxazol-4-yl)-ethyl ester (386 mg, 1.06 mmol) and Cs$_2$CO$_3$ (423 mg, 1.3 mmol) were combined in anhydrous DMF (7 mL) and stirred for 16 h at 55° C. under an atmosphere of nitrogen. The mixture was then cooled, diluted with ethyl acetate (50 mL), and washed with water and brine. The organic layer was dried with Na$_2$SO$_4$ and concentrated in vacuo to a viscous yellow oil. The residue was purified by flash column chromatography (100 g silica, 60×15 mL fractions, gradient elution 0-20% ethyl acetate in hexanes) to provide the ethyl ether compound as a colorless oil (177 mg, 28%).

Step H

2-Methyl-3-(4-{2-[5-methyl-2-cyclohexyl-oxazol-4-yl]-ethoxy}-phenyl)-2-phenoxypropionic acid The title compound was produced as follows.

2-Methyl-3-(4-{2-[5-methyl-2-cyclohexyl-oxazol-4-yl]-ethoxy}-phenyl)-2-phenoxypropionic acid ethyl ester (175 mg, 3.6 mmol) in MeOH (7 mL) was treated with 2N NaOH (7 mL) and warmed to 55° C. After 18 h, the mixture was concentrated under reduced pressure and then acidified with 5N HCl to a pH of 1. The solution was extracted with EtOAc and then the organic phases dried ($Na_2SO_4$), filtered and concentrated to a white foam (157 mg, 88%): $^1$H NMR (300 MHz, $d_6$-DMSO): δ7.23 (t, J=7.2 Hz, 2H), 7.15 (d, J=8.3 Hz, 2H), 6.91 (dd, J=7.3, 7.2 Hz, 1H), 6.82 (d, J=8.3 Hz, 2H), 6.80 (d, J=7.3 Hz, 2H), 4.16 (t, J=6.3 Hz, 2H), 3.14 (d, J=14.0 Hz, 1H), 3.02 (d, J=14.0 Hz, 1H), 2.77 (t, J=6.3 Hz, 2H), 2.66 (m, 1H), 2.18 (s, 3H), 1.90 (m, 1H), 1.86 (m, 1H), 1.69 (m, 2H), 1.61 (m, 1H), 1.42 (m, 2H), 1.27 (m, 1H), 1.24 (s, 3H), 1.21 (m, 2H). MS [EI+] 464 (M+H)$^+$, [EI−] 462 (M−H)$^+$. HPLC: T=2.98 min, purity 94%.

Example 8

3-(4-{2-[2-(3-Bromophenyl)-5-methyloxazol-4-yl]ethoxy}phenyl)-2-methyl-2-phenoxypropionic acid

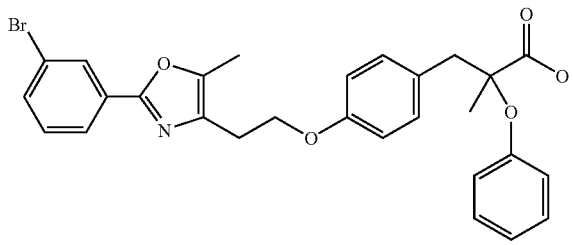

Step A

Toluene-4-sulfonic acid 2-[2-(3-bromophenyl)-5-methyloxazol-4-yl]ethyl ester

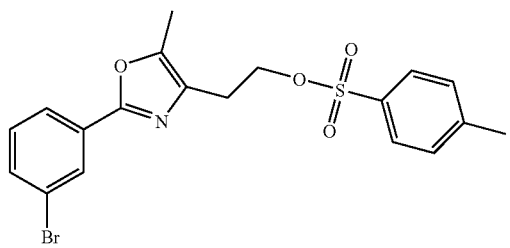

To a solution of 2-(3-bromophenyl)-5-methyl-4-oxazole ethanol (3.27 g, 11.6 mmol) in $CH_2Cl_2$ (46 mL) at rt under $N_2$ was added pyridine (3.28 mL) and DMAP (0.43 g, 3.48 mmol) followed by portionwise addition of tosyl anhydride (4.54 g, 13.9 mmol). The reaction exothermed to 32° C. and was stirred 2 h before 1N HCl (50 mL) was added. The mixture was stirred vigorously 15 min, and then the organic phase was dried ($MgSO_4$) and then concentrated under reduced pressure. The residue was purified by column chromatography (40 mL $SiO_2$, 50% EtOAc/hexanes) to provide toluene-4-sulfonic acid 2-[2-(3-bromophenyl)-5-methyloxazol-4-yl]ethyl ester (4.58 g, 91%) as a white powder: $^1$H NMR (400 MHz, $CDCl_3$) δ 8.01 (t, J=1.6 Hz, 1H) 7.80 (dt, J=7.6 Hz, J=1.6 Hz, 1H), 7.66 (d, J=8.4 Hz, 2H), 7.53 (dt, J=7.6 Hz, J=1.6 Hz, 1H), 7.30 (t, J=7.6 Hz, 1H), 7.19 (d, J=8.4 Hz, 2H), 4.30 (t, J=6.4 Hz, 2H), 2.82 (t, J=6.4 Hz, 2H), 2.31 (s, 3H), 2.24 (s, 3H); MS (EI) 437.0 (M+H)$^+$.

Step B

3-(4-{2-[2-(3-Bromophenyl)-5-methyloxazol-4-yl]ethoxy}phenyl)-2-methyl-2-phenoxypropionic acid ethyl ester

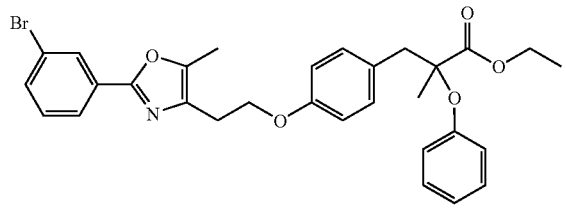

This compound was prepared according to the procedure in Example 1, part D, using 3-(4-hydroxyphenyl)-2-methyl-2-phenoxy-propionic acid ethyl ester (551.5 mg, 1.84 mmol) and toluene-4-sulfonic acid 2-[2-(3-bromophenyl)-5-methyloxazol-4-yl]ethyl ester (1.04 g, 2.39 mmol): Rf=0.54 in 1:4 EtOAc:hexanes; $^1$H NMR (400 MHz, $CDCl_3$) δ 8.14 (s, 1H), 7.92 (d, J=8.0 Hz, 1H), 7.52 (d, J=8.0 Hz, 1H) 7.30 (t, J=7.6 Hz, 1H), 7.21 (t, J=7.6 Hz, 2H), 7.15 (d, J=8.4 Hz, 2H), 6.98-6.95 (m, 1H), 6.82 (d, J=8.4 Hz, 2H) 6.83-6.81 (m, 2H), 4.23 (t, J=6.8 Hz, 2H), 4.20 (q, J=7.6 Hz, 2H), 3.26 (d, J=14.0 Hz, 1H), 3.09 (d, J=14.0 Hz, 1H), 2.97 (t, J=7.6 Hz, 2H), 2.38 (s, 3H), 1.38 (s, 3H), 1.21 (t, J=7.6 Hz, 3H); MS (EI)=564.2 (M+H)$^+$.

Step C

3-(4-{2-[2-(3-Bromophenyl)-5-methyloxazol-4-yl]ethoxy}phenyl)-2-methyl-2-phenoxypropionic acid The title compound was prepared according to the procedure in Example 1, Step E, using 3-(4-{2-[2-(3-bromophenyl)-5-methyloxazol-4-yl]ethoxy}phenyl)-2-methyl-2-phenoxypropionic acid ethyl ester (52 mg, 0.092 mmol): $^1$H NMR (400 MHz, DMSO-$d_6$) δ 7.96 (s, 1H), 7.83 (d, J=8.0 Hz, 1H), 7.62 (d, J=8.0 Hz, 1H), 7.40 (t, J=8.0 Hz, 1H), 7.91 (t, J=7.6 Hz, 2H), 7.08 (d, J=8.4 Hz, 2H), 6.89 (t, J=7.6 Hz, 1H), 6.79 (d, J=8.4 Hz, 2H), 6.75 (d, J=7.6 Hz, 2H), 4.12 (t, J=6.8 Hz, 2H), 3.11 (d, J=13.6 Hz, 1H), 2.99 (d, J=13.6 Hz, 1H), 2.86 (t, J=6.8 Hz, 2H), 2.30 (s, 3H), 1.21 (s, 3H); MS (EI) 536.1 (M+H)$^+$, 535.1 (M−H)$^-$.

Example 9

2-Methyl-3-(4-{2-[5-methyl-2-(1-methylcyclohexyl)oxazol-4-yl]ethoxy}phenyl)-2-phenoxypropionic acid

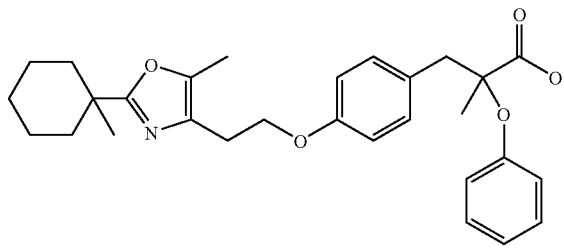

In this synthesis, the following chemical intermediates and title compound were sequentially formed by the procedure of Example 7 using 2-[5-methyl-2-(1-methylcyclohexyl)oxazol-4-yl]ethanol, shown below.

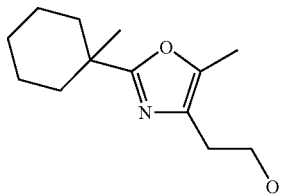

Toluene-4-sulfonic acid 2-[5-methyl-2-(1-methylcyclohexyl)oxazol-4-yl]ethyl ester, shown below:

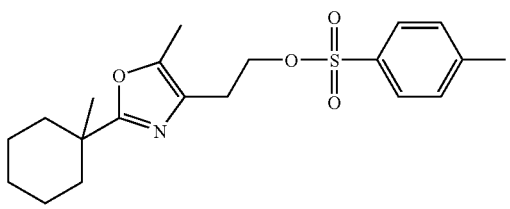

$^1$H NMR (400 MHz, CDCl$_3$) δ 7.73 (d, J=8.4 Hz, 2H), 7.30 (t, J=8.4 Hz, 2H), 4.12 (t, J=6.6 Hz, 2H), 2.76 (t, J=6.6 Hz, 2H), 2.42 (s, 3H), 2.17 (s, 3H), 2.61-2.02 (m, 2H), 1.56-1.30 (m, 8H), 1.19 (s, 3H); MS (EI) 378.2 (M+H)$^+$.

2-Methyl-3-(4-{2-[5-methyl-2-(1-methylcyclohexyl)oxazol-4-yl]ethoxy}phenyl)-2-phenoxypropionic acid ethyl ester, shown below:

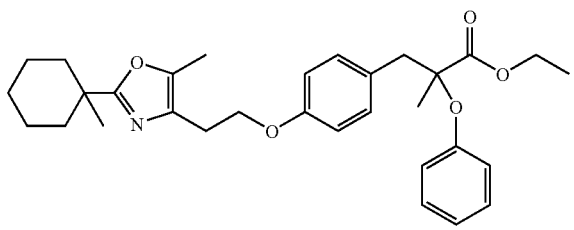

$^1$H NMR (400 MHz, CDCl$_3$) δ 7.24-7.19 (m, 2H), 7.15-7.13 (m, 2H), 6.99-6.95 (m, 1H), 6.83-6.80 (m, 4H), 4.20 (q, J=7.6 Hz, 2H), 4.14 (t, J=6.4 Hz, 2H), 3.29 (d, J=14.0 Hz, 1H), 3.10 (d, J=14.0 Hz, 1H), 2.89 (t, J=6.4 Hz, 2H), 2.24 (s, 3H), 2.11 (broad m, 2H), 1.56-1.24 (v. broad m, 14H), 1.21 (t, J=7.6 Hz, 3H); MS (EI) 506.3 (M+H)$^+$, 528.3 (M+Na)$^+$.

The title compound, 2-methyl-3-(4-{2-[5-methyl-2-(1-methylcyclohexyl)oxazol-4-yl]ethoxy}phenyl)-2-phenoxypropionic acid: $^1$H NMR (400 MHz, DMSO-d$_6$) δ 7.24 (t, J=7.2 Hz, 2H), 7.12 (d, J=8.4 Hz, 2H), 6.94 (t, J=7.2 Hz, 1H), 6.81 (d, J=8.4 Hz, 2H), 6.80 (d, J=7.2 Hz, 2H), 4.09 (t, J=6.8 Hz, 2H), 3.16 (d, J=13.2 Hz, 1H), 3.03 (d, J=13.2 Hz, 1H), 2.78 (t, J=6.8 Hz, 2H), 2.19 (s, 3H), 2.03-1.99 (m, 2H), 1.48-1.27 (m, 11H), 1.16 (s, 3H); MS (EI) 478.3 (M+H)$^+$, 476.3 (M-H)$^-$.

Example 10

3-{4-[2-(2-Cyclohex-1-enyl-5-methyloxazol-4-yl)ethoxy]phenyl}-2-methyl-2-phenoxypropionic acid

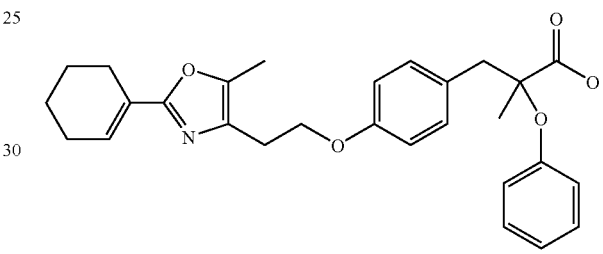

In this synthesis, the following chemical intermediates and the title compound were sequentially prepared by the procedure of Example 7 using 2-(2-cyclohex-1-enyl-5-methyl-oxazol-4-yl)ethanol, shown below.

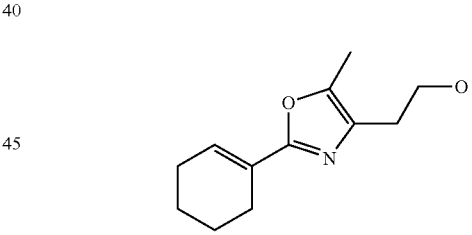

Toluene-4-sulfonic acid 2-(2-cyclohex-1-enyl-5-methyloxazol-4-yl)ethyl ester, shown below: $^1$H NMR (400 MHz, CDCl$_3$) δ 7.68 (d, J=8.0 Hz, 2H), 7.27 (d, J=8.0 Hz, 2H), 6.61 (s, 1H), 4.23 (t, J=6.4 Hz, 2H) 2.76 (t, J=6.4 Hz, 2H), 2.42-2.20 (m, 8H), 1.72-1.63 (m, 6H); MS (EI) 362.2 (M+H)$^+$.

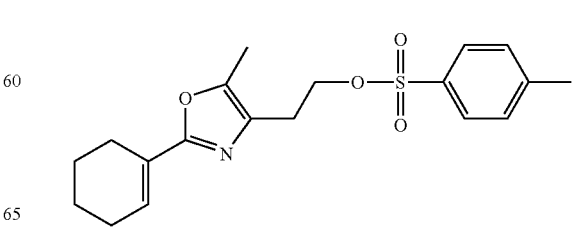

3-{4-[2-(2-Cyclohex-1-enyl-5-methyloxazol-4-yl) ethoxy]phenyl}-2-methyl-2-phenoxypropionic acid ethyl ester, shown below:

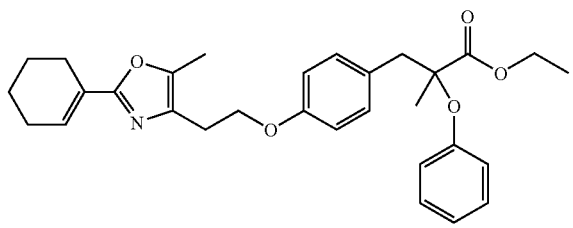

$^1$H NMR (400 MHz, CDCl$_3$) δ 7.23-7.19 (m, 2H), 7.15-7.13 (m, 2H), 6.97 (m, 1H), 6.83-6.79 (m, 4H), 6.34 (s, 1H), 4.20 (q, J=7.6 Hz, 2H), 4.16 (t, J=6.8 Hz, 2H), 3.26 (d, J=13.6 Hz, 1H), 3.09 (d, J=7.6 Hz, 1H), 2.90 (t, J=6.8 Hz, 2H), 2.45-2.43 (m, 2H), 2.28 (s, 3H), 2.22-2.21 (m, 2H), 2.04 (s, 3H), 1.73-1.64 (m, 4H), 1.38 (s, 3H), 1.26 (t, J=7.6 Hz, 3H); MS (EI) 490.3 (M+H)$^+$, 512.3 (M+Na)$^+$.

The title compound, 3-{4-[2-(2-Cyclohex-1-enyl-5-methyloxazol-4-yl)ethoxy]phenyl}-2-methyl-2-phenoxypropionic acid: $^1$H NMR (400 MHz, DMSO-d$_6$) δ 7.24 (t, J=7.2 Hz, 2H), 7.12 (d, J=8.4 Hz, 2H), 6.94 (t, J=7.2 Hz, 1H), 6.82 (d, J=7.2 Hz, 2H), 6.80 (d, J=8.4 Hz, 2H), 6.55 (s, 1H), 4.09 (t, J=6.8 Hz, 2H), 3.16 (d, J=13.2 Hz, 1H), 3.04 (d, J=13.2 Hz, 1H), 2.80 (t, J=6.8 Hz, 2H), 2.32 (bs, 2H) 2.23 (s, 3H), 2.16-2.15 (m, 2H), 1.63-1.55 (m, 4H), 1.27 (s, 3H); MS (EI) 462.2 (M+H)$^+$, 460.3 (M–H)$^-$.

Example 11

3-{3-Methoxy-4-[2-(5-methyl-2-thiophen-2-yloxazol-4-yl)ethoxy]phenyl}-2-methyl-2-phenoxypropionic acid

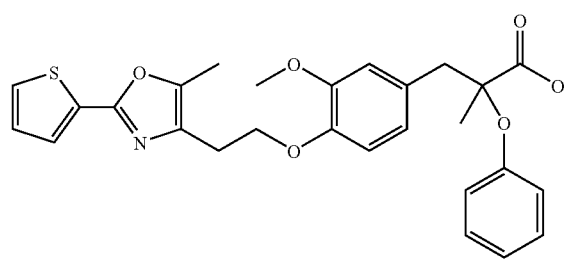

Step A 3-(4-Benzyloxy-3-methoxyphenyl)-3-hydroxy-2-methyl-2-phenoxypropionic acid A stirred solution of LDA in cyclohexane (1.5 M) was cooled to –20° C., to which a solution of 2-phenoxypropionic acid (10 g, 60.2 mmol) in THF (80.3 mL) was slowly added, keeping the temperature below –10° C. The resulting dianion solution was stirred for 15 min, then a solution of 4-benzyloxy-3-methoxybenzaldehyde (14.58 g, 60.2 mmol) in THF (80.3 mL) was added over 1 h, maintaining temperature below –10° C. Fifteen minutes after completion of aldehyde addition, the reaction mixture was poured onto ice water (200 mL), and extracted using 1:2 Et$_2$O:hexane (500 mL). The aqueous layer was isolated, extracted again with 1:2 Et$_2$O:hexane (240 mL), then acidified with concentrated HCl until pH=3. The product acid was extracted into EtOAc (2×165 mL), which was dried over Na$_2$SO$_4$ and concentrated to an orange paste (16.5 g crude, 67%): MS (EI) 426.2 (M+NH$_4$)$^+$, 407.2 (M–H)$^-$.

Step B 3-(4-Benzyloxy-3-methoxyphenyl)-2-methyl-2-phenoxypropionic acid

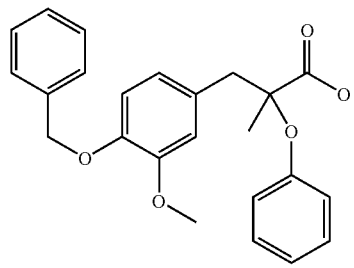

A stirred solution of Et$_3$SiH (8.67 mL, 54.3 mmol) in CH$_2$Cl$_2$ (45 mL) was treated with BF$_3$.Et$_2$O (6.8 mL, 54.3 mmol). 3-(4-Benzyloxy-3-methoxyphenyl)-3-hydroxy-2-methyl-2-phenoxypropionic acid (7.39 g, 18.1 mmol) in CH$_2$Cl$_2$ (90.5 mL) was then added dropwise via addition funnel, maintaining temperature below –7° C. After the addition was complete, the reaction was stirred for 1.5 h at –10° C., then quenched with 1 M NaOH (18.1 mL) and diluted with H$_2$O (12 mL). 1N HCl was used to adjust pH to 4, followed by separation of layers. The aqueous layer was extracted with CH$_2$Cl$_2$ (2×15 mL), and combined organic layers were washed first with 1N HCl (15 mL), then H$_2$O (15 mL), followed by drying over Na$_2$SO$_4$ and concentration to a gummy orange solid (6.86 g, 97%): MS (EI) 410.2 (M+NH$_4$)$^+$, 391.3 (M–H)$^-$.

Step C 3-(4-Hydroxy-3-methoxy-phenyl)-2-methyl-2-phenoxypropionic acid

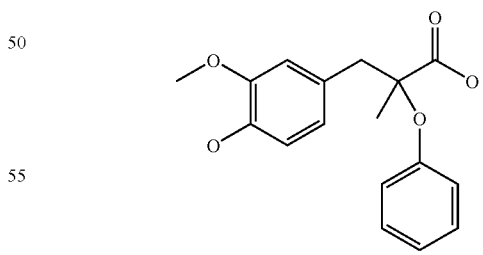

A solution of 3-(4-benzyloxy-3-methoxyphenyl)-2-methyl-2-phenoxypropionic acid (6.86 g, 17.5 mmol) in EtOH (175 mL) was added to 5% Pd/C (186 mg, 10 wt %). The mixture was purged first with nitrogen, then with H$_2$, which was then applied at 45 p.s.i. for 2 h. Pd/C was subsequently filtered off through celite, and the filtrate was concentrated to a crude oil (5.42 g, in excess of theory). MS (EI) 301.2 (M–H)$^-$.

Step D 3-(4-Hydroxy-3-methoxyphenyl)-2-methyl-2-phenoxypropionic acid ethyl ester

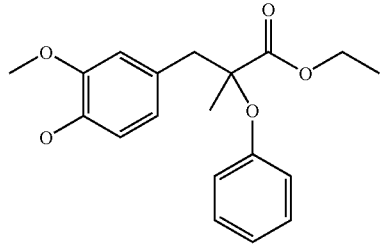

A solution of 3-(4-hydroxy-3-methoxyphenyl)-2-methyl-2-phenoxy-propionic acid (4.56 g, 15.08 mmol) in EtOH (150 mL) was treated with $SOCl_2$ and heated at 75° C. for 14 h, then cooled to rt and partitioned between EtOAc (300 mL) and $H_2O$ (400 mL). The aqueous layer was removed and back-extracted with EtOAc (100 mL). Combined organic phases were washed with 10% $Na_2CO_3$, which was isolated and back-extracted with EtOAc (100 mL). Combined organic phases were washed with brine (200 mL), dried over $Na_2SO_4$, concentrated, and purified by column chromatography (200 g $SiO_2$, 1:4 EtOAc:hexanes) to provide a colorless oil, which developed a green color over a 24-hour period. The material was taken up in EtOAc and filtered through celite, then concentrated to yield a colorless oil (1.99 g, 40%): Rf=0.40 in 1:4 EtOAc:hexanes; $^1$H NMR (400 MHz, $CDCl_3$) δ 7.66-7.55 (m, 1H), 7.25-7.21 (m, 2H), 6.99-6.92 (m, 1H) 6.84-6.79 (m, 3H), 6.74-6.71 (m, 1H), 5.54 (s, 1H), 4.22 (q, J=6.8 Hz, 2H), 3.84 (s, 3H), 3.30 (d, J=14 Hz, 1H), 3.07 (d, J=14 Hz, 1H), 1.40 (s, 3H), 1.23 (t, J=6.8 Hz, 3H).

Step E

3-{3-methoxy-4-[2-(5-methyl-2thiophen-2-yl-oxazol-4-yl)ethoxy]phenyl-2-methyl-2-phenoxypropionic acid The title compound was prepared from 2-(5-methyl-2-thiophen-2-yloxazol-4-yl)ethyl tosylate and 3-(4-hydroxy-3-methoxyphenyl)-2-methyl-2-phenoxypropionic acid ethyl ester according to the parallel synthesis procedure (A). MS (EI) 494.4 (M+H)$^+$.

Example 12

3-{4-[2-(2-Cyclohexyl-5-methyloxazol-4-yl)ethoxy]-3-methoxyphenyl}-2-methyl-2-phenoxypropionic acid

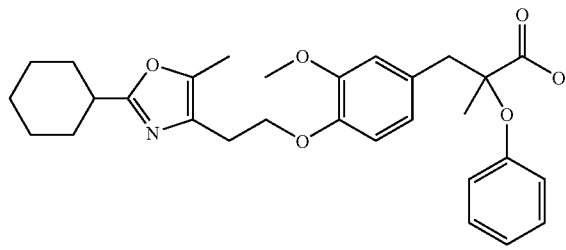

The title compound was prepared by Standard Procedure (A), using 2-(2-cyclohexyl-5-methyloxazol-4-yl)ethyl tosylate. MS (EI) 494.0 (M+H)$^+$.

Example 13

2-Methyl-3-(4-[2-(5-methyl-2-phenyl-oxazol-4-yl)-ethoxy]-3-propyl-phenyl)-2-phenoxy-propionic acid ethyl ester

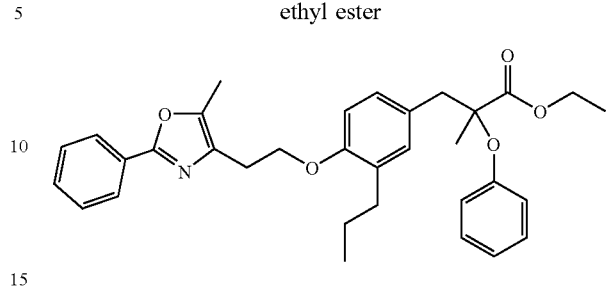

Step A 3-(4-Allyloxyphenyl)-2-methyl-2-phenoxy-propionic acid ethyl ester

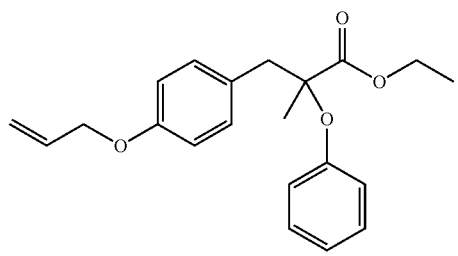

A solution of 3-(4-hydroxyphenyl)-2-methyl-2-phenoxy-propionic acid ethyl ester (500 mg, 1.67 mmol) in methyl ethyl ketone (6 mL) was treated with allyl bromide (232 mg, 1.92 mmol, 0.17 mL) and potassium carbonate (311 mg, 2.25 mmol) and then heated to reflux. After 18 h, the mixture was cooled to ambient temperature and then partitioned between EtOAc and water. The aqueous phase was extracted with EtOAc and then the organic phases were dried ($MgSO_4$), filtered and concentrated under reduced pressure. The residue was purified by column chromatography (100 mL $SiO_2$, hexanes to 10% EtOAc/hexanes) to provide the desired product (478 mg, 84%) as a clear, colorless oil: $^1$H NMR (400 MHz, $CDCl_3$) δ 7.22 (t, J=8.0 Hz, 2H), 7.16 (d, J=8.8 Hz, 2H), 6.97 (dt, J=7.6, 1.2 Hz, 1H), 6.83 (d, J=7.8 Hz, 2H), 6.84 (t, J=8.4 Hz, 2H), 6.05 (ddd, J=17.2, 10.6, 5.2 Hz, 1H), 5.41 (dd, J=17.2, 1.6 Hz, 1H), 5.28 (dd, J=10.8, 1.4 Hz, 1H), 4.22 (d, J=5.2 Hz, 2H), 4.19 (q, J=6.8 Hz, 2H), 3.27 (A of AB, J=14 Hz, 1H), 3.11 (B of AB, J=14 Hz, 1H), 1.40 (s, 3H), 1.21 (t, J=6.8 Hz, 3H).

Step B 3-(3-Allyl-4-hydroxyphenyl)-2-methyl-2-phenoxypropionic acid ethyl ester

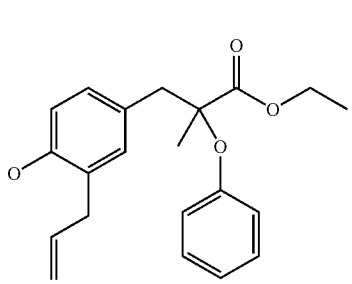

A solution of 3-(4-allyloxyphenyl)-2-methyl-2-phenoxypropionic acid ethyl ester (475 mg, 1.39 mmol) in dimethylaniline (1.5 mL) was heated at reflux for 18 h. After cooling to ambient temperature, the reaction mixture was partitioned between EtOAc and 1N H₂SO₄. The organic phase was dried (MgSO₄), filtered and concentrated. The residue was purified by column chromatography (100 mL SiO₂, hexanes to 30% EtOAc/hexanes) to provide the desired product (343 mg, 72%) as a pale yellow oil: ¹H NMR (400 MHz, CDCl₃) δ 7.23 (t, J=8.4 Hz, 2H), 7.02-6.96 (m, 3H), 6.83 (d, J=8.8 Hz, 2H), 6.72 (d, J=7.6 Hz, 1H), 6.05 (m, 1H), 5.16-5.09 (m, 2H), 4.21 (q, J=6.8 Hz, 2H), 3.38 (d, J=6.4 Hz, 2H), 3.25 (A of AB, J=13.6 Hz, 1H), 3.10 (B of AB, J=13.6 Hz, 1H), 1.41 (s, 3H), 1.23 (t, J=6.8 Hz, 3H).

Step C 3-(4-Hydroxy-3-propylphenyl)-2-methyl-2-phenoxy-propionic acid ethyl ester

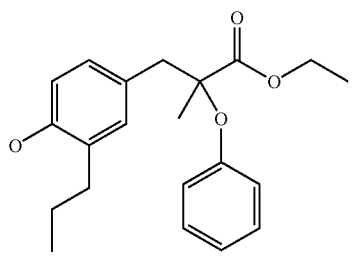

A solution of 3-(3-allyl-4-hydroxyphenyl)-2-methyl-2-phenoxy-propionic acid ethyl ester (330 mg, 0.97 mmol) in absolute EtOH (5 mL) was treated with 5% Pd/C and then the mixture was evacuated three times with N₂. The reaction mixture was hydrogenated at 1 atm with an H₂-filled balloon for 24 h before filtering the mixture over celite and rinsing with EtOH. The product was used without further purification. ¹H NMR (400 MHz, CDCl₃) δ 7.22 (t, J=7.6 Hz, 2H), 7.99-6.95 (m, 3H), 6.82 (m, 2H), 6.68 (d, J=8.0 Hz, 1H), 4.20 (q, J=6.8 Hz, 2H), 3.24 (A of AB, J=13.6 Hz, 1H), 3.08 (B of AB, J=13.6 Hz, 1H), 2.55 (t, J=7.6 Hz, 2 h), 1.62 (sextet, J=7.6 Hz, 2H), 1.41 (s, 3H), 1.23 (t, J=6.8 Hz, 3H), 0.96 (t, J=7.2 Hz, 3H).

Step D

2-Methyl-3-{4-[2-(5-methyl-2-phenyl-oxazol-4-yl)-ethoxy]-3-propyl-phenyl}-2-phenoxy-propionic acid ethyl ester

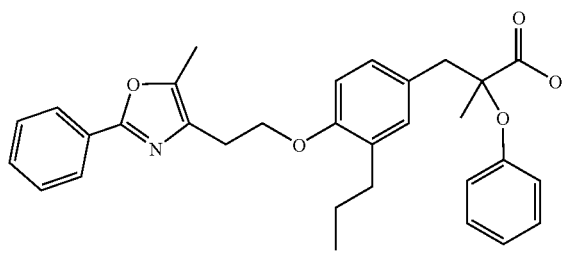

A solution of 3-(4-hydroxy-3-propylphenyl)-2-methyl-2-phenoxy-propionic acid ethyl ester (266 mg, 1.0 mmol) in DMF (10 mL) was treated with cesium carbonate (407 mg, 1.25 mmol) and toluene-4-sulfonic acid 2-(2-phenyl-5-methyl-oxazol-4-yl)-ethyl ester and then heated at 55° C. for 18 h. After cooling to ambient temperature, the mixture was partitioned between EtOAc and water. The aqueous phase was extracted with EtOAc and then the organic phases were dried (MgSO₄), filtered and concentrated under reduced pressure. The residue was purified by column chromatography (100 mL SiO₂, hexanes to 30% EtOAc/hexanes) to provide the desired product (315 mg, 60%) as a clear, colorless oil: MS (EI) 528.3 (M+H)⁺.

Step E

2-Methyl-3-{4-[2-(5-methyl-2-phenyl-oxazol-4-yl)-ethoxy]-3-propyl-phenyl}-2-phenoxy-propionic acid A solution of 3-{4-[2-(5-methyl-2-phenyloxazol-4-yl)-ethoxy]-3-propyl-phenyl}-2-methyl-2-phenoxy-propionic acid ethyl ester in EtOH (1.5 mL) was treated with 5 N NaOH (140 μL) and then warmed to 65° C. After 18 h, the mixture was acidified to pH=1 with 5 N HCl. The mixture was extracted with EtOAc and then the combined organic phases were dried (MgSO₄), filtered and concentrated under reduced pressure to yield the title product. MS (EI) 500.2 (M+H)⁺; LC RT=3.22 min (>99% pure).

Example 14

3-{4-[2-(2-Cyclohexyl-5-methyl-oxazol-4-yl)-ethoxy]-3-propyl-phenyl}-2-methyl-2-phenoxy-propionic acid

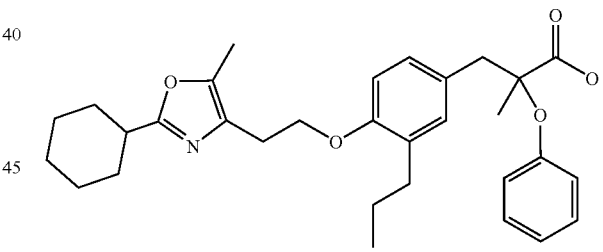

The title compound, and its corresponding ester: MS (EI) 534.3 (M+H)⁺ shown below, were synthesized according to the procedure of Example 13, Steps D and E, respectively from toluene-4-sulfonic acid 2-(2-cyclohexyl-5-methyl-oxazol-4-yl)-ethyl ester, and then purified by LC/MS: MS (EI) 506.2 (M+H)⁺; LC RT=3.11 min (>85% pure).

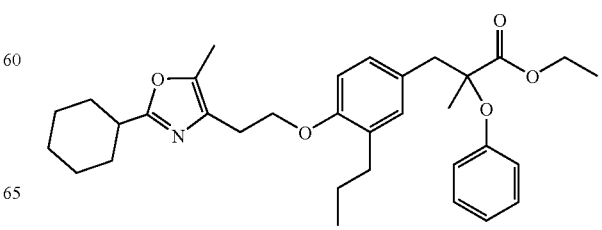

Example 15

2-Methyl-3-{4-[2-(5-methyl-2-thiophen-2-yl-oxazol-4-yl)-ethoxy]-3-propyl-phenyl}-2-phenoxy-propionic acid

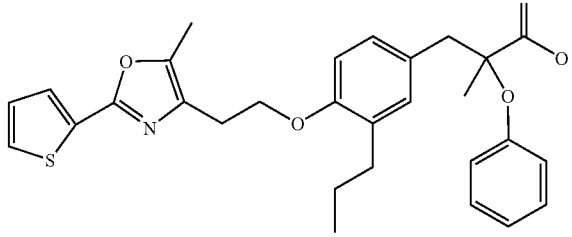

The title compound, and its corresponding ester: MS (EI) 534.2 (M+H)$^+$ shown below, were synthesized according to the procedure of Example 13, Steps D and E, respectively from toluene-4-sulfonic acid 2-(5-methyl-2-thiophen-5-methyl-oxazol-4-yl)-ethyl ester, and then purified by LC/MS: MS (EI) 506.1 (M+H)$^+$; LC RT=3.12 min (>99% pure).

Example 16

3-{4-[2-(2-Phenyl-5-methyl-oxazol-4-yl)-ethoxy]-phenyl}-2-methyl-2-(4-tert-butylphenoxy)-propionic acid

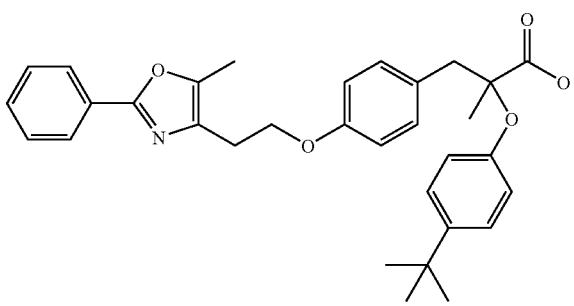

Step A 2-(4-tert-Butyl-phenoxy)-propionic acid ethyl ester

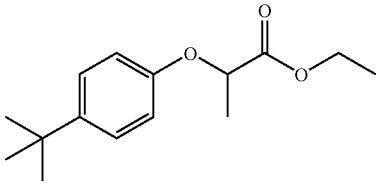

4-t-Butylphenol (7.52 g, 50 mmol) in anhydrous DMF (40 mL) was added dropwise to NaH (2.2 g, 55 mmol, 60% w/w in mineral oil) at 0° C. under an atmosphere of nitrogen. After five min, ethyl 2-bromopropionate (6.49 mL, 50 mmol, d=1.394) was added rapidly dropwise and the resultant mixture was allowed to stir for 18 h, gradually warming to ambient temperature. The reaction mixture was diluted with ethyl acetate (300 mL) and extracted twice with water and once with brine. The organic layer was dried over Na$_2$SO$_4$ and concentrated in vacuo to produce a colorless oil (12.5 g, 100%) $^1$H NMR (300 MHz, CDCl$_3$): δ 7.28 (d, 2H, J=5.5), 6.80 (d, 2H, J=5.5), 4.70 (q, 1H, J=6.6), 4.22 (q, 2H, J=7.1), 1.59 (d, 3H, J=6.6), 1.28 (s, 9H), 1.25 (t, 3H, J=7.1). MS [EI+] 251 (M+H)$^+$, 268 (M+NH$_4$)$^+$.

Step B 2-(4-tert-Butyl-phenoxy)-3-(4-hydroxyphenyl)-2-methylpropionic acid ethyl ester

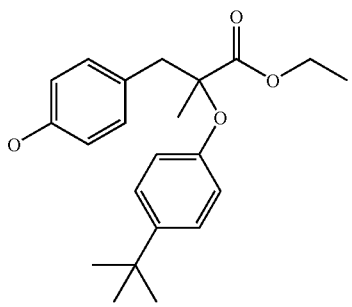

A solution of LDA (12.7 mL, 19.1 mmol, 1.5M in cyclohexane) was cooled to −78° C. in a dry ice/acetone bath and then added to a solution of 2-(4-tert-butyl-phenoxy)-propionic acid ethyl ester in anhydrous THF (20 mL) also cooled to −78° C. under an atmosphere of nitrogen. After five min, 4-benzyloxybenzaldehyde (3.69 g, 17.4 mmol) was added in one portion. After stirring for 10 min, the reaction mixture was quenched with saturated solution of aqueous NH$_4$Cl (10 mL) and the mixture allowed to warm to ambient temperature. The biphasic mixture was diluted with ether (100 mL) and partitioned, and the organic layer was washed with brine, dried over MgSO$_4$ and concentrated in vacuo. The residue was purified by flash column chromatography (600 g silica, 25×200 mL fractions, gradient elution 0-20% ethyl acetate in hexanes) to provide a colorless oil (3.46 g, 58%) as a mixture of inseparable diastereomers of 3-(4-benzyloxy-phenyl)-2-(4-tert-butyl-phenoxy)-3-hydroxy-2- methylpropionic acid ethyl ester which was used without further characterization or purification.

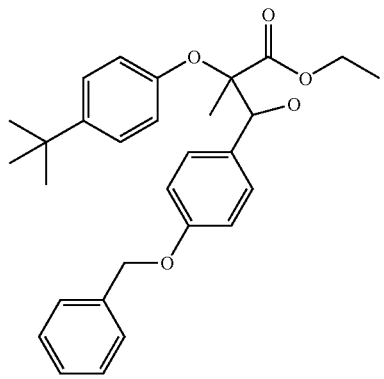

3-(4-Benzyloxy-phenyl)-2-(4-tert-butyl-phenoxy)-3-hydroxy-2-methylpropionic acid ethyl ester (3.46 g, 7.5 mmol) in anhydrous CH$_2$Cl$_2$ (50 mL) was cooled to 0° C. and treated with pyridine (6.0 mL, 75 mmol, d=0.978). Trifluoroacetic anhydride (2.11 mL, 15 mmol, d=1.487) was added dropwise and the mixture was stirred for 1 h, gradually warming to ambient temperature. The solution was washed twice with 1N HCl and the organic layer dried over Na$_2$SO$_4$ and concentrated in vacuo to produce 3-(4-benzyloxyphenyl)-2-(4-tert-butyl-phenoxy)-3-trifluoroacetoxy-2-methylpropionic acid ethyl ester which was used without characterization.

The material was dissolved in ethyl acetate (50 mL) and treated with 10% palladium on carbon (1.5 g), and stirred under an atmosphere of hydrogen for 48 h. The suspension was filtered through celite and concentrated in vacuo to a golden oil. The residue was purified by flash column chromatography (200 g silica, 30×20 mL fractions, 2% ethyl acetate in CHCl$_3$) to provide the title compound as a colorless oil (1.06 g, two steps 40%) $^1$H NMR (300 MHz, CDCl$_3$): δ 7.21 (d, 2H, J=8.6), 7.12 (d, 2H, J=8.6), 4.19 (q, 1H, J=7.1), 3.24 (d, 1H, J=12.3), 3.11 (d, 1H, J=12.3), 1.38 (s, 3H), 1.27 (s, 9H), 1.23 (t, J=7.1). MS [EI+] 357 (M+H)$^+$, [EI−] 355 (M−H)$^+$.

Step C

3-{4-[2-(2-Phenyl-5-methyl-oxazol-4-yl)-ethoxy]-phenyl}-2-methyl-2-(4-tert-butylphenoxy)-propionic acid

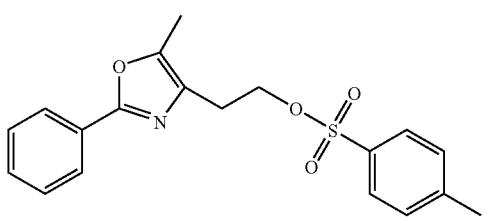

The title compound was prepared using the representative Standard Procedure (A) from 3-(4hydroxyphenyl)-2-methyl-2-(4-tert-butylphenoxy)-propionic acid ethyl ester and toluene-4-sulfonic acid 2-(5-methyl-2-phenyl)-oxazol-4-yl)-ethyl ester to produce a white solid (17%). MS [EI+] 514 (M+H)$^+$, [EI−] 512 (M−H)$^+$.

Example 17

2-Methyl-3-{4-[2-(5-methyl-2-thiophen-2-yl-oxazol-4-yl)-ethoxy]-phenyl}-2-(4-tert-butylphenoxy)-propionic acid

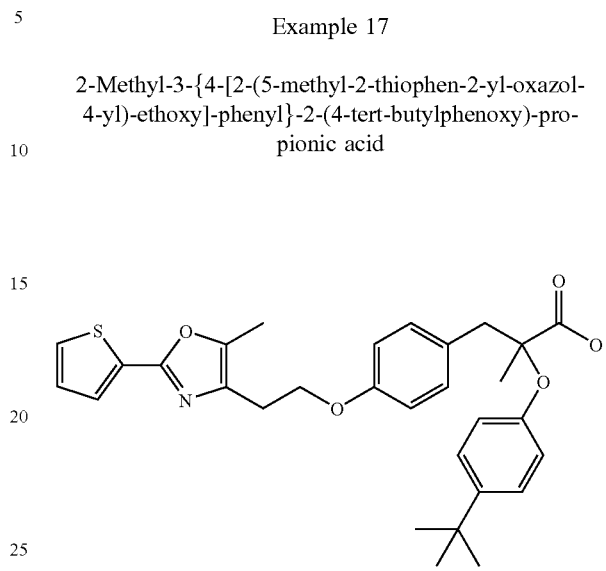

The title compound was prepared, acording to the procedure of Example 16, Step C, using 3-(4-hydroxyphenyl)-2-methyl-2-(4-tert-butylphenoxy)-propionic acid ethyl ester and toluene-4-sulfonic acid 2-(5-methyl-2-thiophen-2-yl-oxazol-4-yl)-ethyl ester to produce a white solid (19%). MS [EI+] 520 (M+H)$^+$, [EI−] 518 (M−H)$^+$.

Example 18

2-Methyl-3-(4-{2-[5-methyl-2-cyclohexylyl-oxazol-4-yl]-ethoxy}-phenyl)-2-(4-tert-butylphenoxy)-propionic acid

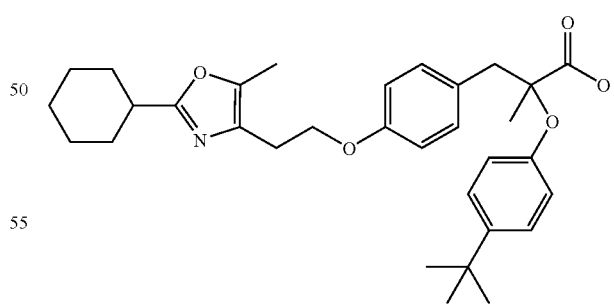

The title compound was prepared, according to the procedure of Example 16, Step C, using 3-(4-hydroxyphenyl)-2-methyl-2-(4-tert-butylphenoxy)-propionic acid ethyl ester and toluene-4-sulfonic acid 2-(5-methyl-2-cyclohexylyl-oxazol-4-yl)-ethyl ester to produce a white solid (18%). MS [EI+] 520 (M+H)$^+$, [EI−] 518 (M−H)$^+$

Example 19

2-Methyl-3-{4-[2-(5-methyl-2-thiophen-2-yl-oxazol-4-yl)-ethoxy]-phenyl}-2-(4-methoxyphenoxy)-propionic acid

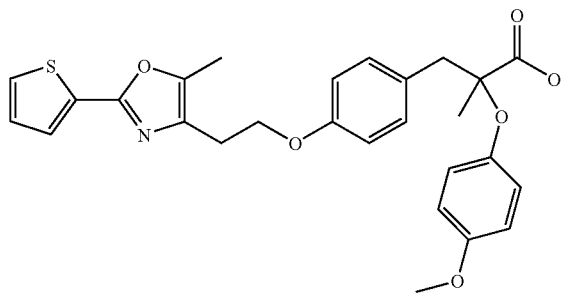

Step A 2-(4-Methoxyphenoxy)-propionic acid ethyl ester

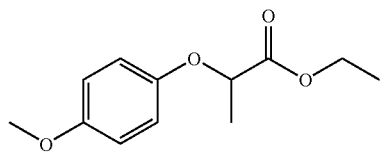

4-Methoxyphenol (3.29 g, 26.5 mmol), K$_2$CO$_3$ (7.32 g, 53 mmol), and ethyl 2-bromopropionate (4.8 g, 26.5 mmol) were combined in anhydrous DMF (50 mL) and stirred at 90° C. under an atmosphere of nitrogen. After 16 h, the DMF was removed in vacuo. The residue was dissolved in ethyl acetate (100 mL) and washed twice with water and once with brine. The organic layer was dried over Na$_2$SO$_4$ and concentrated in vacuo to produce a golden oil (4.8 g, 81%) $^1$H NMR (250 MHz, CDCl$_3$): δ 6.76 (d, 2H, J=7.9), 6.73 (d, 2H, J=7.9), 4.58 (q, 1H, J=6.1), 4.14 (q, 2H, J=7.2), 3.69 (s, 3H), 1.52 (d, 3H, J=6.1), 1.19 (t, 3H, J=7.2). MS [EI+] 225 (M+H)$^+$, [EI−] 223 (M−H)$^+$.

Step B 2-(4-Methoxyphenoxy)-3-(4-benzyloxyphenyl)-2-methylpropionic acid ethyl ester

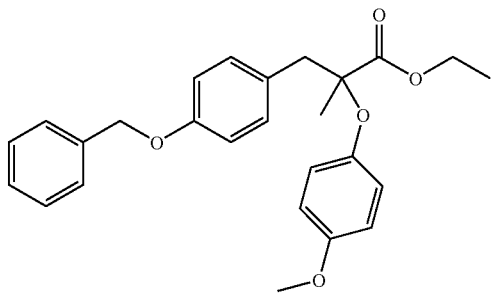

A solution of 2-(4-methoxyphenoxy)-propionic acid ethyl ester in anhydrous THF (20 mL) was cooled to −78° C. under nitrogen and then treated with dropwise addition of LDA (13.4 mL, 20 mmol, 1.5M in cyclohexane) at a rate slow enough to keep the temperature below −70° C. After 30 min, 4-benzyloxybenzaldehyde (3.88 g, 18.3 mmol) in anhydrous THF was added slowly dropwise in the fashion previously described. After stirring for 30 min, the reaction mixture was quenched with saturated solution of aqueous NH$_4$Cl (20 mL) and the mixture was warmed to ambient temperature. The biphasic mixture was diluted with ether (100 mL) and partitioned, and the organic layer was washed with brine, dried over MgSO$_4$ and concentrated in vacuo. The residue was purified by flash column chromatography (500 g silica, 40×125 mL fractions, gradient elution 0-20% ethyl acetate in hexanes) to provide a colorless oil (3.97 g, 50%) as a mixture of inseparable diastereomers of 3-(4-benzyloxy-phenyl)-2-(4-methoxyphenoxy)-3-hydroxy-2-methylpropionic acid ethyl ester which was used without further characterization or purification. R$_f$=0.28 in 4:1 hexanes:ethyl acetate.

3-(4-Benzyloxyphenyl)-2-(4-methoxyphenoxy)-3-hydroxy-2-methylpropionic acid ethyl ester (2.15 g, 4.9 mmol) in anhydrous CH$_2$Cl$_2$ (30 mL) was cooled to 0° C. and treated with BF$_3$-Et$_2$O (0.91 mL, 7.4 mmol, d=1.154) and triethylsilane (1.18 mL, 7.4 mmol, d=0.728). The mixture was stirred for 2 h, gradually warming to ambient temperature. Saturated aqueous Na$_2$CO$_3$ (15 mL) was added and the mixture was stirred vigorously. The solution was partitioned and the organic layer was washed twice with water and brine, dried over Na$_2$SO$_4$, and concentrated in vacuo to produce 3-(4-benzyloxy-phenyl)-2-(4-methoxyphenoxy)-2-methylpropionic acid ethyl ester as a colorless oil (428 mg, 21%). R$_f$=0.36 in 4:1 hexanes:ethyl acetate $^1$H NMR (300 MHz, CDCl$_3$): δ 7.45 (t, 2H, J=7.1), 7.35 (d, 2H, J=7.1), 7.34 (t, 1H, J=7.0), 7.18 (d, 2H, 8.6), 6.91 (d, 2H, J=6.6), 6.79 (d, 2H, 8.6), 6.74 (d, 2H, J=6.6), 5.05 (s, 2H), 4.21 (q, 1H, J=7.1), 3.75 (s, 3H), 3.23 (d, 1H, J=13.7), 3.10 (d, 1H, J=13.7), 1.31 (s, 3H), 1.25 (t, 3H, J=7.1). MS [EI+] 438 (M+NH$_4$)$^+$, [EI−] 419 (M−H)$^+$.

Step C 2-(4-Methoxyphenoxy)-3-(4-hydroxyphenyl)-2-methylpropionic acid ethyl ester

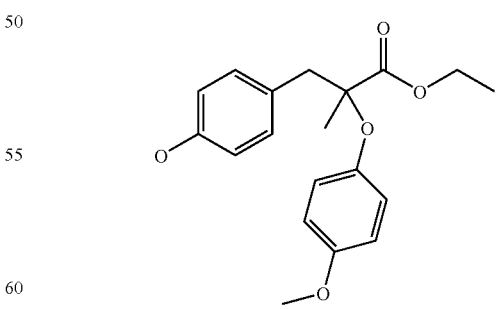

3-(4-Benzyloxy-phenyl)-2-(4-methoxyphenoxy)-2-methylpropionic acid ethyl ester (428 mg, 1.0 mmol) was dissolved in ethanol (50 mL) and treated with 5% palladium on carbon (200 mg), and stirred under an atmosphere of hydrogen for 16 h. The suspension was filtered through celite and concentrated in vacuo to provide a colorless oil. (257 mg, 76%) ¹H NMR (300 MHz, CDCl₃): δ 7.06 (d, 2H, J=8.6), 6.73 (d, 2H, J=6.6), 6.72 (d, 2H, J=8.6), 6.69 (t, 1H, J=6.6), 4.16 (q, 1H, J=7.4), 3.68 (s, 3H), 3.14 (d, 1H, J=13.7), 3.01 (d, 1H, J=13.7), 1.23 (s, 3H), 1.18 (t, J=7.4). MS [EI+] 331 (M+H)⁺, 348 (M+NH₄)⁺, [EI−] 329 (M−H)⁺.

2-(4-Methoxyphenoxy)-3-(4-hydroxyphenyl)-2-methyl-propionic acid ethyl ester (515821) (approx. 2.5 g) prepared in the same manner was purified by chiral chromatography to provide the individual enantiomers (Chiracel OD, 8×29 cm, 5% IPA/heptane, 275 nm; (S)-isomer: 1.09 g, 97.4% ee, (R)-isomer: 1.01 g, >99% ee).

Step D

2-Methyl-3-{4-[2-(5-methyl-2-thiophen-2-yl-oxazol-4-yl)-ethoxy]-phenyl}-2-(4-methoxyphenoxy)-propionic acid ethyl ester

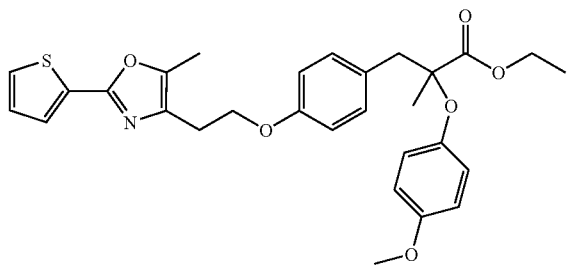

Prepared from 3-(4-hydroxyphenyl)-2-methyl-2-(4-methoxyphenoxy)-propionic acid ethyl ester and toluene-4-sulfonic acid 2-(5-methyl-2-thiophen-2-yl-oxazol-4-yl)-ethyl ester to produce a colorless oil (86%). ¹H NMR (300 MHz, CDCl₃): δ 7.57 (d, 1H, J=3.5), 7.36 (d, 1H, J=5.1), 7.15 (d, 2H, J=8.6), 7.07 (dd, 1H, J=5.1, 3.5), 6.81 (d, 2H, J=6.6), 6.78 (d, 2H, J=8.6), 6.71 (d, 2H, J=6.6), 4.21 (q, 2H, J=7.2), 4.20 (t, 2H, J=6.4), 3.74 (s, 3H), 3.21 (d, 1H, J=13.7), 3.08 (d, 1H, J=13.7), 2.95 (t, 2H, J=6.4), 2.35 (s, 3H), 1.28 (s, 3H), 1.25 (t, 3H, J=7.2). MS [EI+] 522 (M+H)⁺.

Step E

2-Methyl-3-{4-[2-(5-methyl-2-thiophen-2-yl-oxazol-4-yl)-ethoxy]-phenyl}-2-(4-methoxyphenoxy)-propionic acid The title compound was prepared from 2-methyl-3-{4-[2-(5-methyl-2-thiophen-2-yl-oxazol-4-yl)-ethoxy]-phenyl}-2-(4-methoxyphenoxy)-propionic acid ethyl ester using the hydrolysis procedure of Example 1, Step E, to provide a white solid (63%). ¹H NMR (300 MHz, d₆-DMSO): δ 7.70 (d, 1H, J=4.8), 7.57 (d, 1H, J=3.9), 7.15 (dd, 1H, J=4.8, 3.9), 7.10 (d, 2H, J=8.6), 6.83 (d, 2H, J=8.6), 6.76 (d, 2H, J=9.0), 6.71 (d, 2H, J=9.0), 4.12 (t, 2H, J=6.4), 3.65 (s, 3H), 3.07 (d, 1H, J=13.7), 3.06 (d, 1H, J=13.7), 2.86 (t, 2H, J=6.4), 2.30 (s, 3H), 1.20 (s, 3H). MS [EI+] 494 (M+H)⁺, [EI−] 492 (M−H).

Example 20

(S)-2-Methyl-3-{4-[2-(5-methyl-2-thiophen-2-yl-oxazol-4-yl)-ethoxy]-phenyl}-2-(4-methoxyphenoxy)-propionic acid

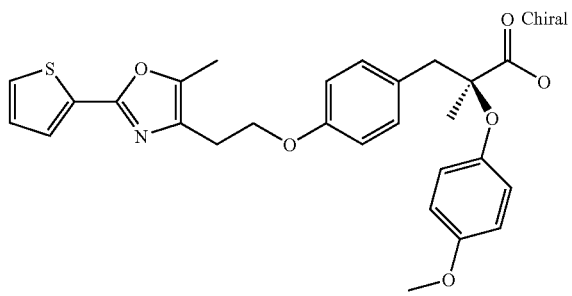

Step A (S)-2-Methyl-3-{4-[2-(5-methyl-2-thiophen-2-yl-oxazol-4-yl)-ethoxy]-phenyl}-2-(4-methoxyphenoxy)-propionic acid ethyl ester

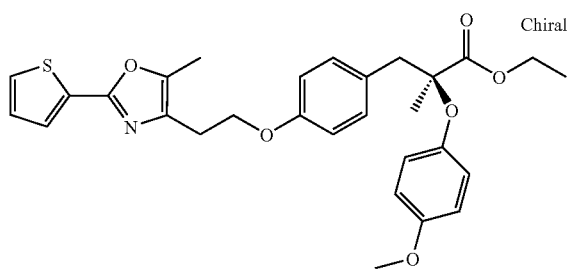

The title compound was prepared from (S)-3-(4-hydroxyphenyl)-2-methyl-2-(4-methoxyphenoxy)-propionic acid ethyl ester and toluene-4-sulfonic acid 2-(5-methyl-2-thiophen-2-yl-oxazol-4-yl)-ethyl ester to produce a colorless oil (32%). ¹H NMR (300 MHz, CDCl₃): δ 7.57 (d, 1H, J=3.5), 7.36 (d, 1H, J=5.1), 7.15 (d, 2H, J=8.6), 7.07 (dd, 1H, J=5.1, 3.5), 6.81 (d, 2H, J=6.6), 6.78 (d, 2H, J=8.6), 6.71 (d, 2H, J=6.6), 4.21 (q, 2H, J=7.2), 4.20 (t, 2H, J=6.4), 3.74 (s, 3H), 3.21 (d, 1H, J=13.7), 3.08 (d, 1H, J=13.7), 2.95 (t, 2H, J=6.4), 2.35 (s, 3H), 1.28 (s, 3H), 1.25 (t, 3H, J=7.2). MS [EI+] 522 (M+H)⁺.

Step B (S)-2-Methyl-3-{4-[2-(5-methyl-2-thiophen-2-yl-oxazol-4-yl)-ethoxy]-phenyl}-2-(4-methoxyphenoxy)-propionic acid The title compound was prepared from (S)-2-methyl-3-{4-[2-(5-methyl-2-thiophen-2-yl-oxazol-4-yl)-ethoxy]-phenyl}-2-(4-methoxyphenoxy)-propionic acid ethyl ester, according to the procedure of Example 19, Step E, to provide a sticky white solid (83%). ¹H NMR (300 MHz, d₆-DMSO): δ 7.70 (d, 1H, J=4.8), 7.57 (d, 1H, J=3.9), 7.15 (dd, 1H, J=4.8, 3.9), 7.10 (d, 2H, J=8.6), 6.83 (d, 2H, J=8.6), 6.76 (d, 2H, J=9.0), 6.71 (d, 2H, J=9.0), 4.12 (t, 2H, J=6.4), 3.65 (s, 3H), 3.07 (d, 1H, J=13.7), 3.06 (d, 1H, J=13.7), 2.86 (t, 2H, J=6.4), 2.30 (s, 3H), 1.20 (s, 3H). MS [EI+] 494 (M+H)$^+$, [EI−] 492 (M−H).

Example 21

2-(3-Fluoro-phenoxy)-2-methyl-3-{4-[2-(5-methyl-2-phenyl-oxazol-4-yl)-ethoxy]-phenyl}-propionic acid

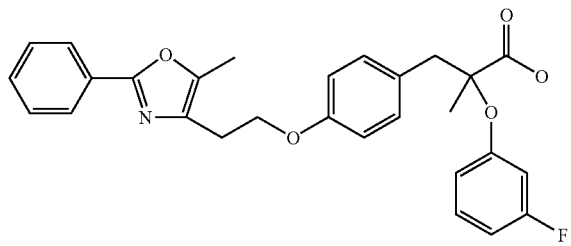

2-(3-Fluoro-phenoxy)-2-methyl-3-{4-[2-(5-methyl-2-phenyl-oxazol-4-yl)-ethoxy]-phenyl}-propionic acid was obtained from 2-(3-fluoro-phenoxy)-3-(4-hydroxyphenyl)-2-methyl-propionic acid ethyl ester by the Standard Procedure (B). $^1$H NMR (400 MHz, CDCl$_3$) δ 7.99-7.97 (m, 2H), 7.47-7.45 (m, 3H), 7.21-7.15 (m, 3H), 6.82 (d, 2H, J=8.2 Hz), 6.76-6.61 (m, 3H), 4.20 (t, 2H, J=6.3 Hz), 3.26 (d, 1H, J=14.1 Hz), 3.12 (d, 1H, J=14.1 Hz), 3.05 (t, 2H, J=6.3 Hz), 2.42 (s, 3H), 1.44 (s, 3H). HRMS (ES$^+$) m/z exact mass calcd for C$_{28}$H$_{26}$FNO$_5$ 476.1873, found 476.1869.

Example 22

2-(3-Fluoro-phenoxy)-2-methyl-3-{4-[2-(5-methyl-2-thiophen-2-yl-oxazol-4-yl)-ethoxy]-phenyl}-propionic acid

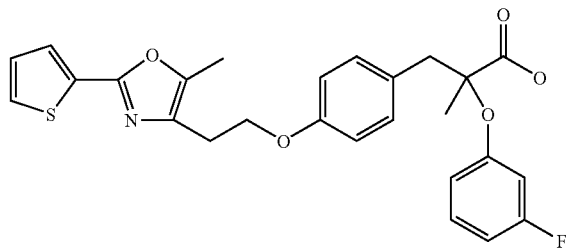

The title compound was prepared from 2-(3-fluoro-phenoxy)-3-(4-hydroxyphenyl)-2-methyl-propionic acid ethyl ester and toluene-4-sulfonic acid 2-(5-methyl-2-thiophen-2-yl-oxazol-4-yl)-ethyl ester according to the method of Example 21. $^1$H NMR (400 MHz, CDCl$_3$) δ 7.64 (dd, 1H, J=3.5 Hz, 1.17 Hz), 7.41 (dd, 1H, J=5.1 Hz, 1.17 Hz), 7.19-7.16 (m, 3H), 7.08 (dd, 0.1H, J=5.1 Hz, 3.91 Hz), 6.81 (d, 2H, J=8.6 Hz), 6.75-6.62 (m, 3H), 4.17 (t, 2H, J=6.6 Hz), 3.26 (d, 1H, J=13.7 Hz), 3.14 (d, 1H, J=13.69 Hz), 2.98 (t, 2H, J=6.65 Hz), 2.36 (s, 3H), 1.45 (s, 3H). HRMS (ES$^+$) m/z exact mass calcd for C$_{26}$H$_{25}$FNO$_5$S 482.1437, found 482.1454.

Example 23

2-(3-Fluoro-phenoxy)-2-methyl-3-{4-[2-(5-methyl-2-cyclohexyl-oxazol-4-yl)-ethoxy]-phenyl}-propionic acid

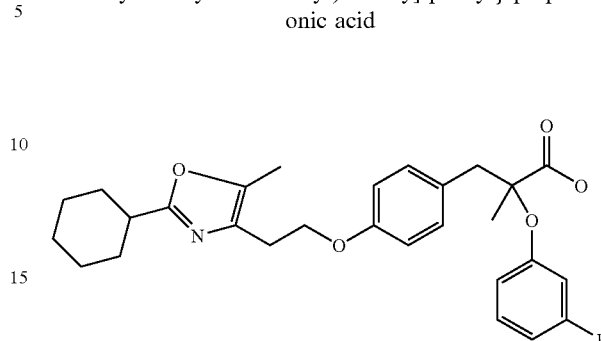

The title compound was prepared from 2-(3-fluoro-phenoxy)-3-(4-hydroxyphenyl)-2-methyl-propionic acid ethyl ester and toluene-4-sulfonic acid 2-(2-cyclohexyl-5-methyl-oxazol-4-yl)-ethyl ester according to the method of Example 21.

$^1$H NMR (400 MHz, CDCl$_3$) δ 7.87 (d, 1H, J=7.8 Hz), 7.57 (d, 2H, J=7.8 Hz), 7.50-7.27 (m, 5H), 7.12 (m, 3H), 6.76 (d, 2H, J=8.6 Hz), 6.72-6.58 (m, 3H), 4.14 (t, 2H, J=6.7 Hz), 3.18 (d, 1H, J=14.1 Hz), 3.08 (d, 1H, J=14.1 Hz), 2.94 (t, 2H, J=6.7 Hz), 2.37 (s, 3H), 1.38 (s, 3H). MS (ES$^+$) m/z mass calcd for C$_{34}$H$_{31}$FNO$_5$ 552.21, found 552.2.

Example 24

2-(3-tert-Butyl-phenoxy)-2-methyl-3-{4-[2-(5-methyl-2-phenyl-oxazol-4-yl)-ethoxy]-phenyl}-propionic acid

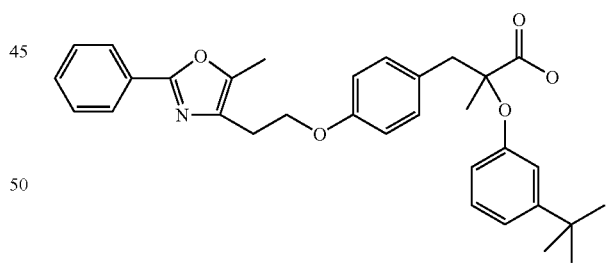

2-(3-t-Butyl-phenoxy)-2-methyl-3-{4-[2-(5-methyl-2-phenyl-oxazol-4-yl)-ethoxy]-phenyl}-propionic acid was obtained from 2-(3-tert-butyl-phenoxy)-3-(4-hydroxy-phenyl)-2-methyl-propionic acid ethyl ester by the Standard Procedure (B). $^1$H NMR (400 MHz, CDCl$_3$) δ 7.19-7.16 (m, 3H), 7.08 (dt, 1H, J=7.0 Hz, 0.8 Hz), 7.92 (t, 1H, J=2.0 Hz), 6.83 (d, 2H, J=8.6 Hz), 6.72-6.99 (m, 1H), 4.21 (t, 2H, J=6.3 Hz), 3.25 (d, 1H, J=14.1 Hz), 3.15 (d, 1H, J=14.1 Hz), 3.00 (t, 2H, J=6.3 Hz), 2.39 (s, 3H), 1.43 (s, 3H), 1.25 (s, 9H). HRMS (ES$^+$) m/z exact mass calcd for C$_{32}$H$_{354}$NO$_5$ 514.2593, found 514.2622.

Example 25

2-(3-tert-Butyl-phenoxy)-2-methyl-3-{4-[2-(5-methyl-2-thiophen-2-yl-oxazol-4-yl)-ethoxy]-phenyl}-propionic acid

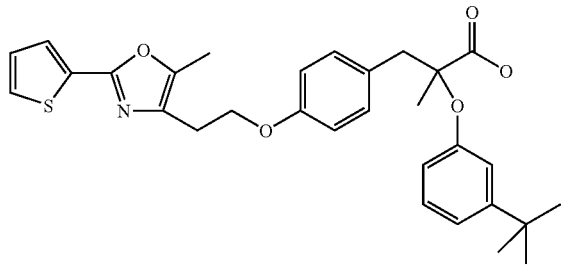

The title compound was prepared from 2-(3-tert-butyl-phenoxy)-3-(4-hydroxy-phenyl)-2-methyl-propionic acid ethyl ester and toluene-4-sulfonic acid 2-(5-methyl-2-thiophen-2-yl-oxazol-4-yl)-ethyl ester by the procedure of Example 24.

$^1$H NMR (400 MHz, CDCl$_3$) δ 7.60 (dd, 1H, J=3.91 Hz, 1.17 Hz), 7.37 (dd, 1H, J=5.09 Hz, 1.17 Hz), 7.19-7.16 (m, 3H), 7.08-7.06 (m, 2H), 6.89 (t, 1H, J=2.35 Hz), 6.82 (d, 2H, J=8.60 Hz), 6.71 (dd, 1H, J=8.60 Hz, 2.74 Hz), 4.19 (t, 2H, J=6.26 Hz), 3.25 (d, 1H, J=14.08 Hz), 3.15 (d, 1H, J=14.08 Hz), 2.96 (t, 2H, J=6.26 Hz), 2.35 (s, 3H), 1.43 (s, 3H), 1.26 (s, 9H). HRMS (ES$^+$) m/z exact mass calcd for C$_{30}$H$_{34}$NO$_5$S 520.2157, found 520.2182.

Example 26

2-(2-Fluoro-phenoxy)-2-methyl-3-{4-[2-(5-methyl-2-phenyl-oxazol-4-yl)-ethoxy]-phenyl}-propionic acid

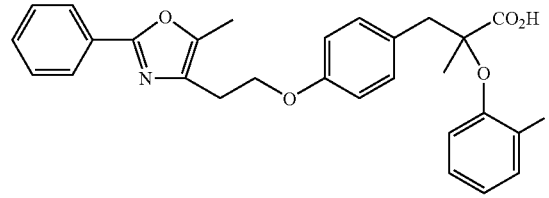

2-(2-Fluorophenoxy)-2-methyl-3-{4-[2-(5-methyl-2-phenyl-oxazol-4-yl)-ethoxy]-phenyl}-propionic acid was prepared from 2-(2-fluorophenoxy)-3-(4-hydroxy-phenyl)-2-methyl-propionic acid ethyl ester by the parallel synthesis method (B). $^1$H NMR (400 MHz, CDCl$_3$) δ 7.96 (dd, 2H, J=7.43 Hz, 2.35 Hz), 7.42-7.40 (m, 3H), 7.22 (d, 2H, J=8.99 Hz), 7.12-6.95 (m, 4H), 6.84 (d, 2H, J=8.60 Hz), 4.20 (t, 2H, J=6.65 Hz), 3.26 (d, 1H, J=14.08 Hz), 3.18 (d, 1H, J=14.08 Hz), 2.99 (t, 2H, J=6.65 Hz), 2.38 (s, 3H), 1.42 (s, 3H). HRMS (ES$^+$) m/z exact mass calcd for C$_{28}$H$_{26}$FNO$_5$ 476.1873, found 476.1858.

Example 27

2-(2-Fluoro-phenoxy)-2-methyl-3-{4-[2-(5-methyl-2-thiophen-2-yl-oxazol-4-yl)-ethoxy]-phenyl}-propionic acid

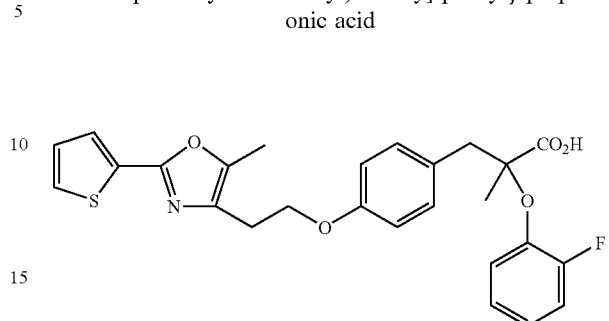

The title compound was prepared from 2-(2-fluorophenoxy)-3-(4-hydroxy-phenyl)-2-methyl-propionic acid ethyl ester and toluene-4-sulfonic acid 2-(5-methyl-2-thiophen-2-yl-oxazol-4-yl)-ethyl ester by the procedure of Example 26.
$^1$H NMR (400 MHz, CDCl$_3$) δ 7.58 (dd, 1H, J=3.52 Hz, 1.17 Hz), 7.36 (dd, 1H, J=5.08 Hz, 1.17 Hz), 7.21 (d, 3H, J=8.60 Hz), 7.12-6.95 (m, 3H), 6.83 (d, 3H, J=8.60 Hz), 4.19 (t, 2H, J=6.65 Hz), 3.27 (d, 1H, J=14.08 Hz), 3.17 (d, 1H, J=14.08 Hz), 2.95 (t, 2H, J=6.65 Hz), 2.35 (s, 3H), 1.41 (s, 3H). HRMS (ES$^+$) m/z exact mass calcd for C$_{26}$H$_{25}$FNO$_5$S 482.1437, found 482.1454.

Example 28

3-{4-[2-(2-Cyclohexyl-5-methyl-oxazol-4-yl)-ethoxy]-phenyl}-2-(2-fluoro-phenoxy)-2-methyl-propionic acid

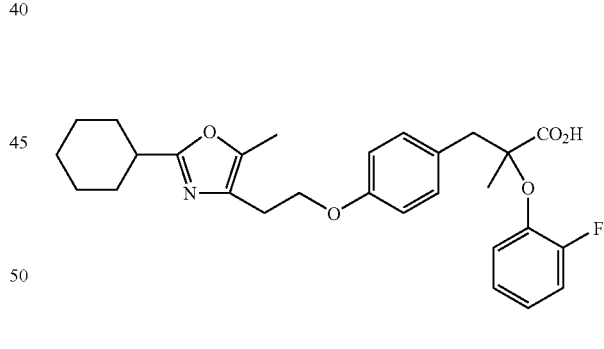

The title compound was prepared from 2-(2-fluorophenoxy)-3-(4-hydroxy-phenyl)-2-methyl-propionic acid ethyl ester and toluene-4-sulfonic acid 2-(2-cyclohexyl-5-methyl-oxazol-4-yl)-ethyl ester by the procedure of Example 26. $^1$H NMR (400 MHz, CDCl$_3$) δ 7.21 (d, 2H, J=8.60 Hz), 7.12-6.96 (m, 4H), 6.79 (d, 2H, J=8.60 Hz), 4.15 (t, 2H, J=6.65 Hz), 3.26 (d, 1H, J=14.08 Hz), 3.19 (d, 1H, J=14.08 Hz), 2.98-2.80 (m, 2H), 2.32 (s, 3H), 2.02 (d, 2H, J=10.95 Hz), 1.81 (d, 2H, J=12.90 Hz), 1.70 (d, 1H, J=12.90 Hz), 1.85 (q, 2H, J=11.73 Hz), 1.40 (s, 3H), 1.39-1.23 (m, 3H). HRMS (ES$^+$) m/z exact mass calcd for C$_{28}$H$_{33}$FNO$_5$ 482.2343, found 482.2349.

Example 29

2-(4-Chloro-phenoxy)-2-methyl-3-{4-[2-(5-methyl-2-phenyl-oxazol-4-yl)-ethoxy]-phenyl}-propionic acid

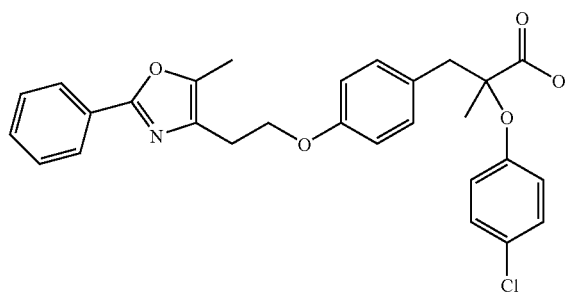

2-(4-Chlorophenoxy)-2-methyl-3-{4-[2-(5-methyl-2-phenyl-oxazol-4-yl)-ethoxy]-phenyl}-propionic acid was obtained from 2-(4-chlorophenoxy)-3-(4-hydroxy-phenyl)-2-methyl-propionic acid ethyl ester by the Standard Procedure (B). $^1$H NMR (400 MHz, CDCl$_3$) δ 7.98-7.96 (m, 2H), 7.45 (d, 3H, J=6.65 Hz), 7.17 (t, 4H, J=7.43 Hz), 6.82 (dd, 4H, J=8.60 Hz, 2.74 Hz), 4.20 (t, 2H, J=6.26 Hz), 3.23 (d, 1H, J=14.08 Hz), 3.12 (d, 1H, J=14.08 Hz), 3.04 (t, 2H, J=6.26 Hz), 2.41 (s, 3H), 1.39 (s, 3H). MS (ES$^+$) m/z mass calcd for $C_{28}H_{27}ClNO_5$ 492.16, found 492.2.

Example 30

2-(4-Chlorophenoxy)-2-methyl-3-{4-[2-(5-methyl-2-thiophen-2-yl-oxazol-4-yl)-ethoxy]-phenyl}-propionic acid

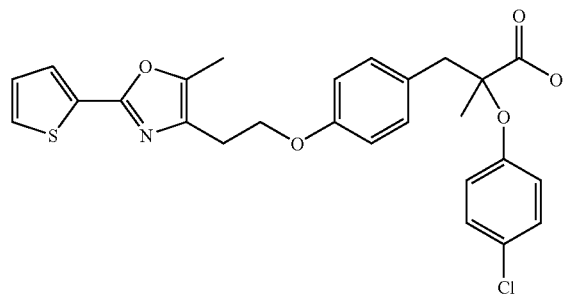

The title compound was prepared from 2-(4-chlorophenoxy)-3-(4-hydroxy-phenyl)-2-methyl-propionic acid ethyl ester and toluene-4-sulfonic acid 2-(5-methyl-2-thiophen-2-yl-oxazol-4-yl)-ethyl ester by the procedure of Example 29. $^1$H NMR (400 MHz, CDCl$_3$) δ 7.59 (d, 1H, J=4.30 Hz), 7.38 (d, 1H, J=4.30 Hz), 7.20-7.16 (m, 4H), 7.06 (dd, 1H, J=8.60 Hz, 3.91 Hz), 6.83 (t, 4H, J=8.60 Hz), 4.17 (t, 2H, J=6.65 Hz), 3.23 (d, 1H, J=14.08 Hz), 3.14 (d, 1H, J=14.08 Hz), 2.97 (t, 2H, J=6.65 Hz), 2.36 (s, 3H), 1.41 (s, 3H). MS (ES$^+$) m/z mass calcd for $C_{26}H_{25}ClNO_5S$ 498.12, found 498.1.

Example 31

2-(4-Chlorophenoxy)-3-{4-[2-(2-cyclohexyl-5-methyl-oxazol-4-yl)-ethoxy]-phenyl}-2-methyl-propionic acid The title compound was prepared from 2-(4-chlorophenoxy)-3-(4-hydroxy-phenyl)-2-methyl-propionic acid ethyl ester and toluene-4-sulfonic acid 2-(2-cyclohexyl-5-methyl-oxazol-4-yl)-ethyl ester by the procedure of Example 29. $^1$H NMR (400 MHz, CDCl$_3$) δ 7.19 (d, 2H, J=8.60 Hz), 7.16 (d, 2H, J=8.60 Hz), 6.83 (d, 2H, J=8.60 Hz), 6.79 (d, 2H, J=8.60 Hz), 4.12 (t, 2H, J=6.26 Hz), 3.21 (d, 1H, J=14.08 Hz), 3.11 (d, 1H, J=14.08 Hz), 2.95 (t, 2H, J=6.26 Hz), 2.89-2.83 (m, 3H), 2.05 (d, 2H, J=11.73 Hz), 1.80 (d, 2H, J=11.73 Hz), 1.55 (q, 2H, J=11.73 Hz), 1.40 (s, 3H), 1.37-1.20 (m, 4H). MS (ES$^+$) m/z mass calcd for $C_{28}H_{33}ClNO_5$ 498.21, found 498.2.

Example 32

2-(4-Cyclohexyl-phenoxy)-2-methyl-3-{4-[2-(5-methyl-2-phenyl-oxazol-4-yl)-ethoxy]-phenyl}-propionic acid 2-(4-Cyclohexyl-phenoxy)-2-methyl-3-{4-[2-(5-methyl-2-phenyl-oxazol-4-yl)-ethoxy]-phenyl}-propionic acid was obtained from 2-(4-cyclohexylphenoxy)-3-(4-hydroxyphenyl)-2-methylpropionic acid ethyl ester by the Standard Procedure (B). $^1$H NMR (400 MHz, CDCl$_3$) δ 7.99-7.98 (m, 2H), 7.45 (t, 3H, J=2.80 Hz), 7.18 (d, 2H, J=8.60 Hz), 7.08 (d, 2H, J=7.90 Hz), 6.82 (d, 4H, J=8.60 Hz), 4.21 (t, 2H, J=6.26 Hz), 3.22 (d, 1H, J=14.08 Hz), 3.12 (d, 1H, J=14.08 Hz), 2.40 (s, 4H), 1.83-1.71 (m, 5H), 1.40 (s, 3H), 1.38-1.16 (m, 6H). MS (ES$^+$) m/z mass calcd for $C_{34}H_{38}NO_5$ 540.28, found 540.3.

Example 33

2-(4-Cyclohexyl-phenoxy)-2-methyl-3-{4-[2-(5-methyl-2-thiophen-2-yl-oxazol-4-yl)-ethoxy]-phenyl}-propionic acid

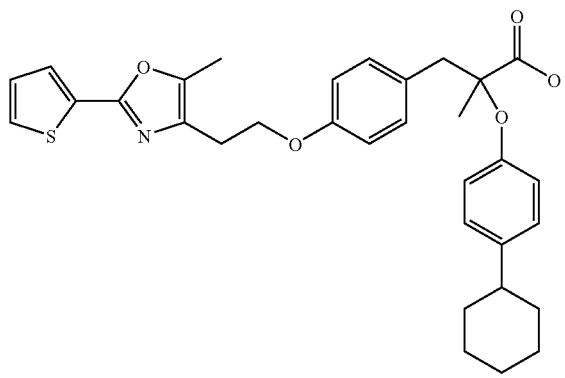

The title compound was prepared from 2-(4-cyclohexylphenoxy)-3-(4-hydroxyphenyl)-2-methylpropionic acid ethyl ester by the method of Example 32. $^1$H NMR (400 MHz, CDCl$_3$) δ 7.68 (d, 1H, J=3.13 Hz), 7.43 (dd, 1H, J=4.69 Hz, 0.78 Hz), 7.18 (d, 2H, J=8.60 Hz), 7.10 (dd, 1H, J=5.08 Hz, 3.52 Hz), 7.08 (d, 2H, J=8.60 Hz), 6.87-6.80 (m, 4H), 4.19 (t, 2H, J=6.26 Hz), 3.39 (s, 5H), 3.23 (d, 1H, J=14.08 Hz), 3.11 (d, 1H, J=14.08 Hz), 2.99 (t, 2H, J=6.26 Hz), 2.37 (s, 3H), 1.82 (d, 4H, J=11.73 Hz), 1.73 (d, 1H, J=11.73 Hz), 1.40 (s, 3H). MS (ES$^+$) m/z mass calcd for C$_{32}$H$_{36}$NO$_5$S 546.23, found 546.2.

Example 34

3-{4-[2-(2-Cyclohexyl-5-methyl-oxazol-4-yl)-ethoxy]-phenyl}-2-(4-cyclohexyl-phenoxy)-2-methyl-propionic acid

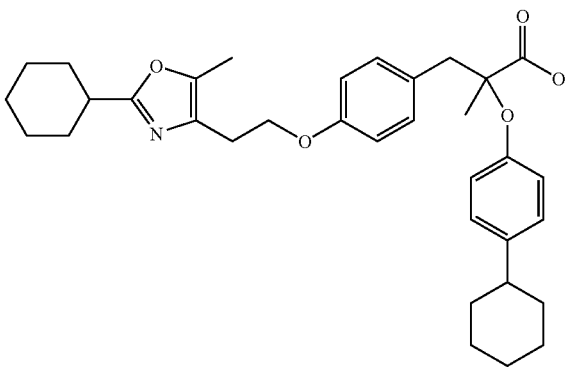

The title compound was prepared from 2-(4-cyclohexylphenoxy)-3-(4-hydroxyphenyl)-2-methylpropionic acid ethyl ester by the method of Example 32. $^1$H NMR (400 MHz, CDCl$_3$) δ 7.18 (d, 2H, J=8.60 Hz), 7.08 (d, 2H, J=8.60 Hz), 6.80 (q, 4H, J=8.60 Hz), 4.14 (t, 2H, J=6.26 Hz), 3.38 (s, 6H), 3.22 (d, 1H, J=14.08 Hz), 3.12 (d, 1H, J=14.08 Hz), 2.96 (t, 2H, J=6.26 Hz), 2.92-2.83 (m, 2H), 2.30 (s, 3H), 2.02 (d, 2H, J=10.56), 1.81-1.78 (m, 6H), 1.76-1.68 (m, 2H), 1.59-1.50 (m, 2H), 1.40 (s, 3H). MS (ES$^+$) m/z mass calcd for C$_{34}$H$_{44}$NO$_5$ 546.32, found 546.3.

Example 35

3-{4-[2-(2-Cyclohexyl-5-methyl-oxazol-4-yl)-ethoxy]-phenyl}-2-(3,4-dimethyl-phenoxy)-2-methyl-propionic acid

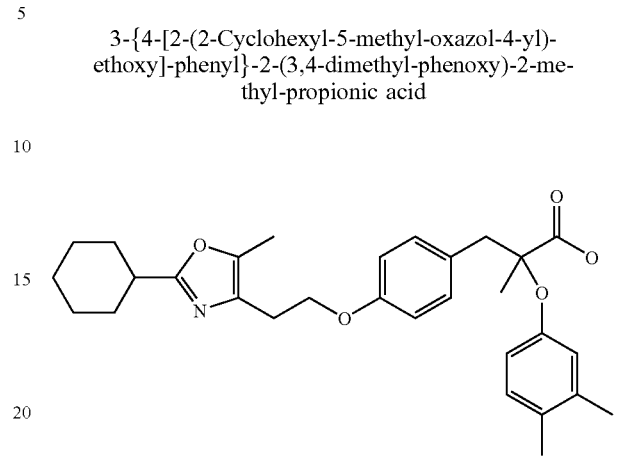

The representative parallel synthesis procedure (B) was used to prepare the title compound from 2-(3,4-dimethylphenoxy)-3-(4-hydroxyphenyl)-2-methylpropionic acid ethyl ester and toluene-4-sulfonic acid 2-(2-cyclohexyl-5-methyl-oxazol-4-yl)-ethyl ester. $^1$H NMR (400 MHz, CDCl$_3$) δ 7.18 (d, 2H, J=8.4 Hz), 6.99 (d, 1H, J=8.4 Hz), 6.79 (d, 2H, J=8.4 Hz), 6.71 (d, 1H, J=2.4 Hz), 6.64 (dd, 1H, J=8.4, 2.4 Hz), 4.16 (t, 2H, J=6.0 Hz), 3.21 and 3.11 (d of Abq, 2H, J=14.0 Hz), 2.98 (t, 2H, J=6.0 Hz), 2.91 (tt, 1H, J=11.4, 3.2 Hz), 2.31 (s, 3H), 2.20 (s, 3H), 2.19 (s, 3H), 2.06-2.02 (m, 2H), 1.85-1.79 (m, 2H), 1.73-1.68 (m, 1H), 1.62-1.51 (m, 2H), 1.42-1.22 (m, 3H), 1.39 (s, 3H). IR (KBr) 3500, 2935, 1735, 1612, 1513, 1249, 1178 cm$^{-1}$. HRMS (ES$^+$) m/z exact mass calcd for C$_{30}$H$_{38}$NO$_5$ 492.2750, found 492.2751.

Example 36

2-(3,4-Dimethyl-phenoxy)-2-methyl-3-{4-[2-(5-methyl-2-thiophen-2-yl-oxazol-4-yl)-ethoxy]-phenyl}-propionic acid

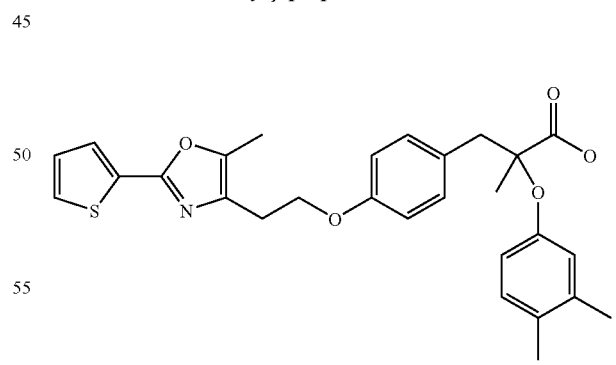

The procedure of Example 35 was used to prepare the title compound from 2-(3,4-dimethylphenoxy)-3-(4-hydroxyphenyl)-2-methylpropionic acid ethyl ester and toluene-4-sulfonic acid 2-(5-methyl-2-thipohen-2-yl-oxazol-4-yl)-ethyl ester. $^1$H NMR (400 MHz, CDCl$_3$) δ 7.73 (d, 1H, J=3.2 Hz), 7.46 (d, 1H, J=4.8 Hz), 7.18 (d, 2H, J=8.4 Hz), 7.13-7.10 (m, 1H), 7.06 (bs, 1H), 6.99 (d, 1H, J=8.0 Hz), 6.81 (d, 2H, J=8.4 Hz), 6.70 (d, 1H, J=2.4 Hz), 6.63 (dd, 1H, J=8.0, 2.4 Hz), 4.20 (t, 2H, J=6.0 Hz), 3.23 and 3.11 (d of Abq, 2H, J=14.0 Hz), 3.02 (t, 2H, J=6.0 Hz), 2.38 (s, 3H), 2.19 (s, 3H), 2.18 (s, 3H), 1.39 (s, 3H). IR (KBr) 3500, 3000, 1729, 1512, 1250, 1178 cm$^{-1}$. HRMS (ES$^+$) m/z exact mass calcd for $C_{28}H_{30}NO_5S$ 492.1845, found 492.1845.

Example 37

2-(3,4-Dimethyl-phenoxy)-2-methyl-3-{4-[2-(5-methyl-2-phenyl-oxazol-4-yl)-ethoxy]-phenyl}-propionic acid

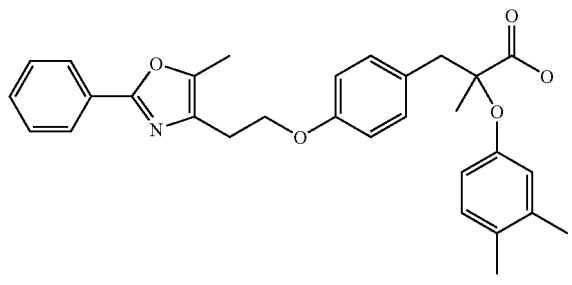

The representative parallel synthesis procedure (B) was used to prepare the title compound from 2-(3,4-dimethylphenoxy)-3-(4-hydroxyphenyl)-2-methylpropionic acid ethyl ester and toluene-4-sulfonic acid 2-(2-phenyl-5-methyl-oxazol-4-yl)-ethyl ester. $^1$H NMR (400 MHz, CDCl$_3$) δ 8.01-7.99 (m, 2H), 7.48-7.46 (m, 3H), 7.18 (d, 2H, J=8.8 Hz), 6.99 (d, 1H, J=8.4 Hz), 6.82 (d, 2H, J=8.4 Hz), 6.70 (d, 1H, J=2.0 Hz), 6.63 (dd, 1H, J=8.4, 2.0 Hz), 6.28 (bs, 1H), 4.22 (t, 2H, J=6.4 Hz), 3.22 and 3.11 (d of Abq, 2H, J=13.6 Hz), 3.06 (t, 2H, J=6.4 Hz), 2.42 (s, 3H), 2.19 (s, 3H), 2.18 (s, 3H), 1.39 (s, 3H). IR (KBr) 3100, 2950, 1772, 1611, 1512, 1177 cm$^{-1}$. HRMS (ES$^+$) m/z exact mass calcd for $C_{30}H_{32}NO_5$ 486.2280, found 486.2295.

Example 38

2-(3,4-Dimethyl-phenoxy)-2-methyl-3-(4-{2-[5-methyl-2-(1-methyl-cyclohexyl)-oxazol-4-yl]-ethoxy}-phenyl)-propionic acid

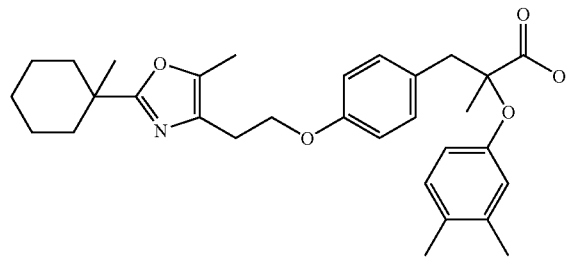

The representative parallel synthesis procedure (B) was used to prepare the title compound from 2-(3,4-dimethylphenoxy)-3-(4-hydroxyphenyl)-2-methylpropionic acid ethyl ester and toluene-4-sulfonic acid 2-(5-methyl-2-(1-methylcyclohexyl)-oxazol-4-yl)-ethyl ester. $^1$H NMR (400 MHz, CDCl$_3$) δ 7.10 (d, 2H, J=8.60 Hz), 6.92 (d, 1H, J=8.60 Hz), 6.73 (d, 2H, J=8.99 Hz), 6.64 (d, 1H, J=2.35 Hz), 6.57 (dd, 1H, J=8.21 Hz, J=3.13 Hz), 4.06 (t, 2H, J=6.25 Hz), 3.14 (d, 1H, J=14.08 Hz), 3.04 (d, 1H, J=14.08 Hz), 2.85 (t, 2H, J=6.25 Hz), 2.19 (s, 3H), 2.13 (s, 3H), 2.12 (s, 3H), 2.07-2.01 (m, 2H), 1.53-1.28 (m, 8H), 1.36 (s, 3H), 1.20 (s, 3H); MS (ES$^+$) calcd for $C_{31}H_{40}NO_5$: Found m/e 506.3 (M+1, 100%).

Example 39

2-Methyl-3-{4-[2-(5-methyl-2-phenyl-oxazol-4-yl)-ethoxy]-phenyl}-2-p-tolyloxy-propionic acid

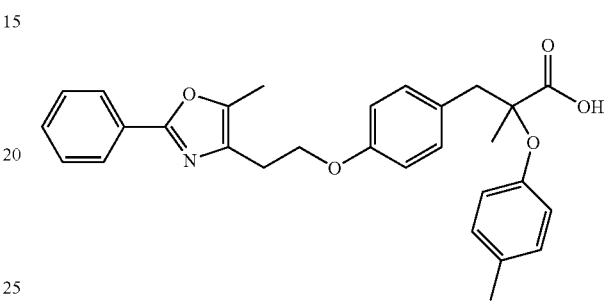

The representative procedure (B) was utilized to prepare the title compound from 3-(4-hydroxyphenyl)-2-methyl-2-p-tolyloxypropionic acid ethyl ester and toluene-4-sulfonic acid 2-(2-phenyl-5-methyl-oxazol-4-yl)-ethyl ester.

$^1$H NMR (400 MHz, CDCl$_3$) δ 8.05 (bs, 1H), 8.02-7.96 (m, 2H), 7.51-7.45 (m, 3H), 7.18 (d, 2H, J=8.4 Hz), 7.05 (d, 2H, J=8.4 Hz), 6.81 and 6.81 (d of Abq, 4H, J=8.0 Hz), 4.22 (t, 2H, J=6.0 Hz), 3.23 and 3.11 (d of Abq, 2H, J=14.0 Hz), 3.06 (t, 2H, J=6.0 Hz), 2.42 (s, 3H), 2.28 (s, 3H), 1.38 (s, 3H). IR (KBr) 3420, 1718, 1712, 1508, 1228 cm$^{-1}$. HRMS (ES$^+$) m/z exact mass calcd for $C_{29}H_{30}NO_5$ 472.2124, found 474.2139.

Example 40

2-Methyl-3-{4-[2-(5-methyl-2-thiophen-2-yl-oxazol-4-yl)-ethoxy]-phenyl}-2-p-tolyloxy-propionic acid

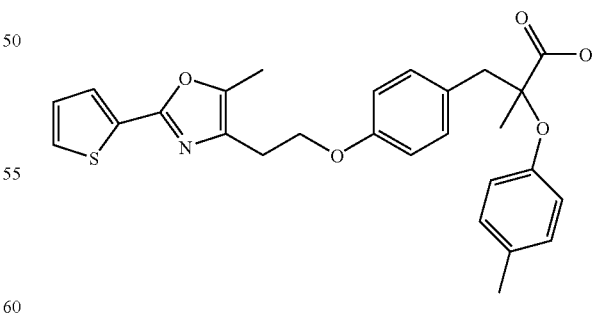

The representative procedure (B) was utilized to prepare the title compound from 3-(4-hydroxyphenyl)-2-methyl-2-p-tolyloxypropionic acid ethyl ester and toluene-4-sulfonic acid 2-(5-methyl-2-thiophen-2-yl-oxazol-4-yl)-ethyl ester.
$^1$H NMR (400 MHz, CDCl$_3$) δ 10.0 (bs, 1H), 7.59 (dd, 1H, J=3.8, 1.2 Hz), 7.36 (dd, 1H, J=5.0, 1.2 Hz), 7.19 (d, 2H, J=8.4 Hz), 7.05 (dd, 1H, J=5.0, 3.8 Hz), 7.02 (d, 2H, J=8.0 Hz), 6.83-6.80 (m, 4H), 4.17 (t, 2H, J=6.4 Hz), 3.29 and 3.14 (d of Abq, 2H, J=13.8 Hz), 2.96 (t, 2H, J=6.4 Hz), 2.35 (s, 3H), 2.27 (s, 3H), 1.38 (s, 3H). IR (KBr) 3420, 1715, 1509, 1225 cm$^{-1}$. HRMS (ES$^+$) m/z exact mass calcd for $C_{27}H_{28}NO_5S$ 478.1688, found 478.1714.

Example 41

3-{4-[2-(2-Cyclohexyl-5-methyl-oxazol-4-yl)-ethoxy]-phenyl}-2-methyl-2-p-tolyloxy-propionic acid

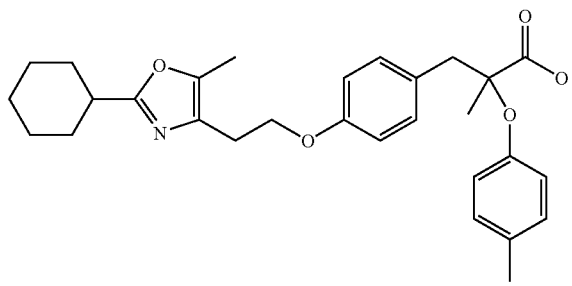

The representative procedure (B) was utilized to prepare the title compound from 3-(4-hydroxyphenyl)-2-methyl-2-p-tolyloxypropionic acid ethyl ester and toluene-4-sulfonic acid 2-(2-cyclohexyl-5-methyl-oxazol-4-yl)-ethyl ester. $^1$H NMR (400 MHz, CDCl$_3$) δ 10.90 (bs, 1H), 7.18 (d, 2H, J=8.4 Hz), 7.05 (d, 2H, J=8.4 Hz), 6.79 and 6.79 (d of Abq, 4H, J=8.0 Hz), 4.15 (t, 2H, J=6.0 Hz), 3.23 and 3.11 (d of Abq, 2H, J=13.8 Hz), 3.02-2.93 (m, 3H), 2.34 (s, 3H), 2.29 (s, 3H), 2.10-2.00 (m, 2H), 1.89-1.80 (m, 2H), 1.77-1.70 (m, 1H), 1.64-1.51 (m, 2H), 1.45-1.19 (m, 3H), 1.38 (s, 3H). IR (KBr) 3450, 1734, 1509, 1228 cm$^{-1}$. HRMS (ES$^+$) m/z exact mass calcd for $C_{29}H_{36}NO_5$ 478.2593, found 478.2613.

The following compounds were prepared from (S)-3-(4-hydroxyphenyl)-2-methyl-2-p-tolyloxypropionic acid ethyl ester (96% ee, Chiracel OD separation, 8×29 cm, 7% IPA/heptane, 275 nm) by the procedure described in Example 1: (S)-2-Methyl-3-{4-[2-(5-methyl-2-thiophen-2-yl-oxazol-4-yl)-ethoxy]-phenyl}-2-p-tolyloxy-propionic acid and (S)-3-{4-[2-(2-cyclohexyl-5-methyl-oxazol-4-yl)-ethoxy]-phenyl}-2-methyl-2-p-tolyloxy-propionic acid

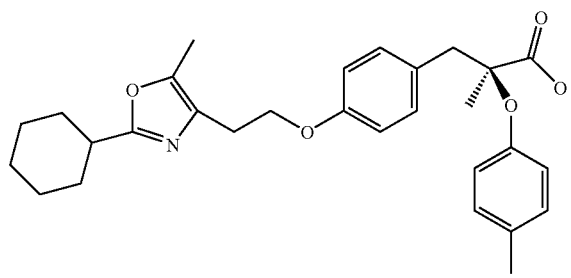

Example 42

2-Methyl-3-{4-[2-(5-methyl-2-phenyl-oxazol-4-yl)-ethoxy]-phenyl}-2-(4-trifluoromethoxy-phenoxy)-propionic acid

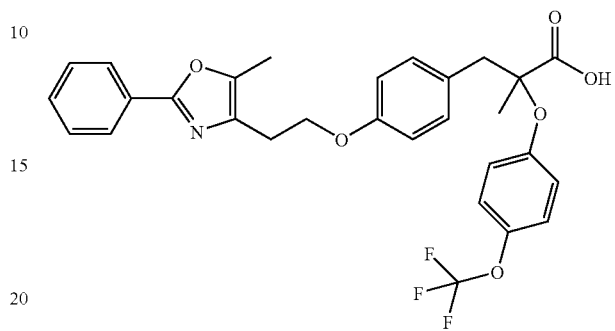

The representative procedure (B) was utilized to prepare the title compound from 3-(4-hydroxy-phenyl)-2-methyl-2-(4-trifluoromethoxy-phenoxy)-propionic acid ethyl ester and toluene-4-sulfonic acid 2-(2-cyclohexyl-5-methyl-oxazol-4-yl)-ethyl ester. $^1$H NMR (400 MHz, CDCl$_3$) δ 7.79-7.94 (m, 2H), 7.43-7.41 (m, 3H), 7.18 (d, 2H, J=8.8 Hz), 7.07 (d, 2H, J=8.4 Hz), 6.89 (d, 2H, J=8.8 Hz), 6.82 (d, 2H, J=8.4 Hz), 4.19 (t, 2H, J=6.4 Hz), 3.24 and 3.14 (d of Abq, 2H, J=14.0 Hz), 3.01 (t, 2H, J=6.4 Hz), 3.00 (bs, 1H), 2.39 (s, 3H), 1.42 (s, 3H). IR (KBr) 3600, 2980, 1725, 1611, 1504, 1265 cm$^{-1}$. HRMS (ES$^+$) m/z exact mass calcd for $C_{29}H_{27}NO_6F_3$ 542.1790, found 542.1802.

Example 43

2-Methyl-3-{4-[2-(5-methyl-2-thiophen-2-yl-oxazol-4-yl)-ethoxy]-phenyl}-2-(4-trifluoromethoxy-phenoxy)-propionic acid

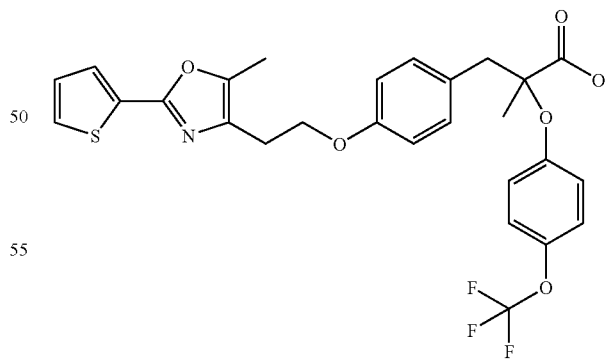

The title compound was prepared from 3-(4-hydroxy-phenyl)-2-methyl-2-(4-trifluoromethoxy-phenoxy)-propionic acid ethyl ester and toluene-4-sulfonic acid 2-(5-methyl-2-thiophen-2-yl-oxazol-4-yl)-ethyl ester using the procedure of Example 42. $^1$H NMR (400 MHz, CDCl$_3$) δ 7.70-7.67 (m, 1H), 7.41 (dd, 1H, J=5.2, 1.2 Hz), 7.17 (d, 2H, J=8.8 Hz), 7.11-7.07 (m, 3H), 6.90 (d, 2H, J=8.8 Hz), 6.83 (d, 2H, J=8.8. Hz), 4.20 (t, 2H, J=6.6 Hz), 3.25 and 3.14 (d of Abq, 2H, J=14.0 Hz), 2.99 (t, 2H, J=6.4 Hz), 2.37 (s, 3H), 1.43 (s, 3H). IR (KBr) 3600, 3000, 1727, 1611, 1504, 1265 cm$^{-1}$. HRMS (ES$^+$) m/z exact mass calcd for $C_{27}H_{25}NO_6F_3S$ 548.1354, found 548.1362.

Example 44

3-{4-[2-(2-Cyclohexyl-5-methyl-oxazol-4-yl)-ethoxy]-phenyl}-2-methyl-2-(4-trifluoromethoxy-phenoxy)-propionic acid

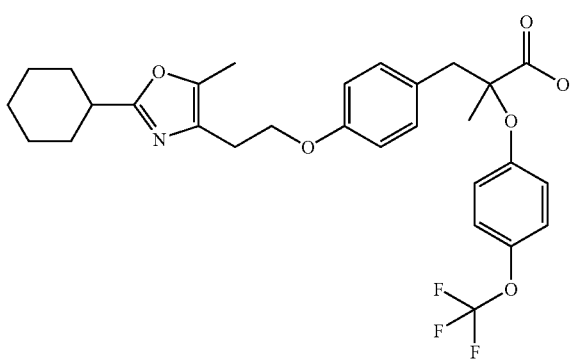

The title compound was prepared from 3-(4-hydroxyphenyl)-2-methyl-2-(4-trifluoromethoxy-phenoxy)-propionic acid ethyl ester and toluene-4-sulfonic acid 2-(2-cyclohexyl-5-methyl-oxazol-4-yl)-ethyl ester using the procedure of Example 42. $^1$H NMR (400 MHz, CDCl$_3$) δ 7.17 (d, 2H, J=8.4 Hz), 7.13 (d, 2H, J=8.4 Hz), 6.90 (d, 2H, J=8.4 Hz), 6.79 (d, 2H, J=8.4 Hz), 4.43 (bs, 1H), 4.16 (t, 2H, J=6.0 Hz), 3.25 and 3.13 (d of Abq, 2H, J=14.0 Hz), 3.02 (t, 2H, J=6.0 Hz), 3.02-2.98 (m, 1H), 2.36 (s, 3H), 2.09-2.00 (m, 2H), 1.88-1.79 (m, 2H), 1.78-1.69 (m, 1H), 1.64-1.52 (m, 2H), 1.43 (s, 3H), 1.40-1.23 (m, 3H). IR (KBr) 3600, 2980, 1725, 1601, 1500, 1268 cm$^{-1}$. HRMS (ES$^+$) m/z exact mass calcd for $C_{29}H_{33}NO_6F_3$ 548.2260, found 548.2274.

Example 45

2-Methyl-3-(4-{2-[5-methyl-2-(1-methyl-cyclohexyl)-oxazol-4-yl]-ethoxy}-phenyl)-2-(4-trifluoromethoxy-phenoxy)-propionic acid

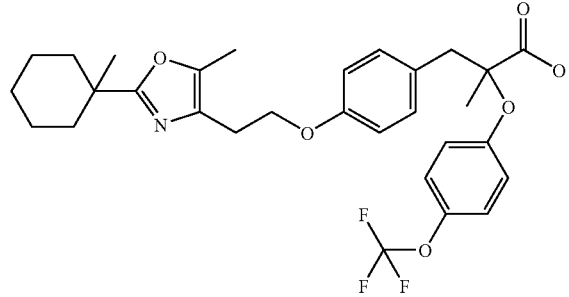

The title compound was prepared from 3-(4-hydroxyphenyl)-2-methyl-2-(4-trifluoromethoxy-phenoxy)-propionic acid ethyl ester and toluene-4-sulfonic acid 2-(5-methyl-2-(1-methylcyclohexyl)oxazol-4-yl)-ethyl ester using the procedure of Example 42. $^1$H NMR (400 MHz, CDCl$_3$) δ 7.16 (d, 2H, J=8.60 Hz), 7.08 (d, 2H, J=8.60 Hz), 6.89 (d, 2H, J=8.60 Hz), 6.79 (d, 2H, J=8.60 Hz), 4.13 (t, 2H, J=6.25 Hz), 3.23 (d, 1H, J=14.08 Hz), 3.11 (d, 1H, J=14.08 Hz), 2.99 (t, 2H, J=6.25 Hz), 2.33 (s, 3H), 2.16-2.08 (m, 2H), 1.62-1.32 (m, 8H), 1.42 (s, 3H), 1.32 (s, 3H); MS (ES$^+$) calcd for $C_{30}H_{35}NO_6F_3$: Found m/e 562.3 (M+1, 100%)

Example 46

2-{4-[2-(5-Methyl-2-phenyl-oxazol-4-yl)-ethoxy]-benzyl}-2-phenoxy-butyric acid

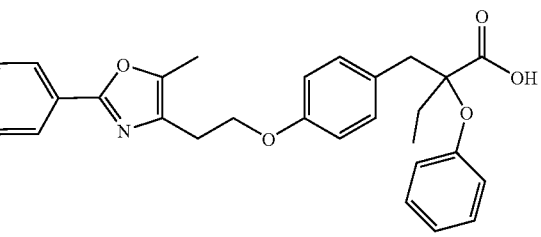

The Standard Procedure (B) was utilized to prepare the title compound from 2-(4-hydroxybenzyl)-2-phenoxybutyric acid ethyl ester and toluene-4-sulfonic acid 2-(2-phenyl-5-methyl-oxazol-4-yl)-ethyl ester. $^1$H NMR (400 MHz, CDCl$_3$) δ 7.99-7.94 (m, 2H), 7.44-7.40 (m, 3H), 7.32-7.28 (m, 2H), 7.07 (t, 1H, J=7.4 Hz), 7.02-6.97 (m, 4H), 6.79-6.74 (m, 2H), 4.18 (t, 2H, J=6.6 Hz), 3.29 (s, 2H), 2.98 (t, 2H, J=6.6 Hz), 2.37 (s, 3H), 2.14 (qd, 1H, J=14.8, 7.6 Hz), 2.07 (qd, 1H, J=14.8, 7.6 Hz), 0.91 (t, 3H, J=7.6 Hz).

Example 47

2-{4-[2-(5-Methyl-2-thiophen-2-yl-oxazol-4-yl)-ethoxy]-benzyl}-2-phenoxy-butyric acid

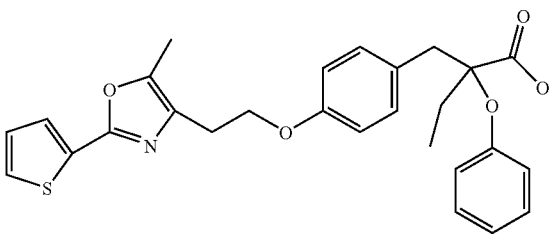

The title compound was prepared from 2-(4-hydroxybenzyl)-2-phenoxybutyric acid ethyl ester and toluene-4-sulfonic acid 2-(5-methyl-2-thiophen-2-yl-oxazol-4-yl)-ethyl ester using the method of Example 46. $^1$H NMR (400 MHz, CDCl$_3$) δ 7.59 (dd, 1H, J=3.6, 0.8 Hz), 7.37 (dd, 1H, J=5.2, 1.2 Hz), 7.33-7.27 (m, 2H), 7.09-7.05 (m, 2H), 7.02-6.96 (m, 4H), 6.78-6.73 (m, 2H), 4.16 (t, 2H, J=6.6 Hz), 3.29 (s, 2H), 2.94 (t, 2H, J=6.6 Hz), 2.34 (s, 3H), 2.14 (qd, 1H, J=14.8, 7.6 Hz), 2.07 (qd, 1H, J=14.8, 7.6 Hz), 0.91 (t, 3H, J=7.6 Hz).

Example 48

2-{4-[2-(2-Cyclohexyl-5-methyl-oxazol-4-yl)-ethoxy]-benzyl}-2-phenoxy-butyric acid

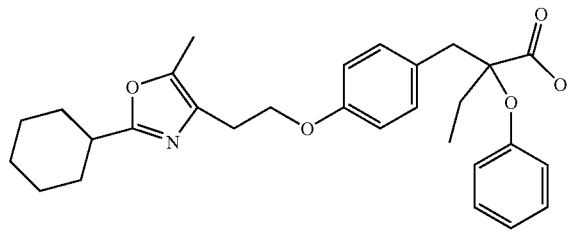

The title compound was prepared from 2-(4-hydroxybenzyl)-2-phenoxybutyric acid ethyl ester and toluene-4-sulfonic acid 2-(2-cyclohexyl-5-methyl-oxazol-4-yl)-ethyl ester using the method of Example 46. $^1$H NMR (400 MHz, CDCl$_3$) δ 8.01 (bs, 1H), 7.31-7.26 (m, 2H), 7.06-6.96 (m, 5H), 6.72 (d, 2H, J=8.8 Hz), 4.08 (t, 2H, J=6.4 Hz), 3.28 (s, 2H), 2.91 (t, 2H, J=6.4 Hz), 2.81 (tt, 1H, J=11.6, 3.6 Hz), 2.26 (s, 3H), 2.18-1.98 (m, 4H), 1.82-1.77 (m, 2H), 1.72-1.67 (m, 1H), 1.58-1.48 (m, 2H), 1.39-1.18 (m, 3H), 0.92 (t, 3H, J=7.6 Hz).

Example 49

2-(4-{2-[5-Methyl-2-(1-methyl-cyclohexyl)-oxazol-4-yl]-ethoxy}-benzyl)-2-phenoxy-butyric acid

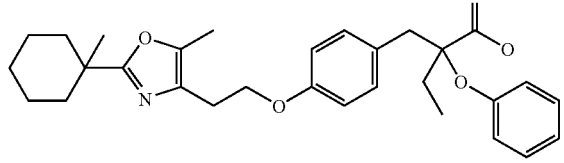

The title compound was prepared from 2-(4-hydroxybenzyl)-2-phenoxybutyric acid ethyl ester and toluene-4-sulfonic acid 2-[5-methyl-2-(1-methylcyclohexyl)oxazol-4-yl)-ethyl ester using the method of Example 46. $^1$H NMR (400 MHz, CDCl$_3$) δ 7.29 (dd, 2H, J=8.60 Hz, J=7.43 Hz), 7.07-7.03 (m, 1H), 7.02-6.96 (m, 4H), 6.72 (d, 2H, J=8.60 Hz), 4.10 (t, 2H, J=6.25 Hz), 2.38 (s, 2H), 2.95 (t, 2H, J=6.25 Hz), 2.29 (s, 3H), 2.15-2.01 (m, 4H), 1.56-1.36 (m, 8H), 1.30 (s, 3H), 0.91 (t, 3H, J=7.43 Hz); MS (ES$^+$) calcd for C$_{30}$H$_{38}$NO$_5$: Found m/e 492.3 (M+1, 100%).

Example 50

2-Methyl-3-{4-[2-(5-methyl-2-phenyl-oxazol-4-yl)-ethoxy]-phenyl}-2-(4-trifluoromethyl-phenoxy)-propionic acid

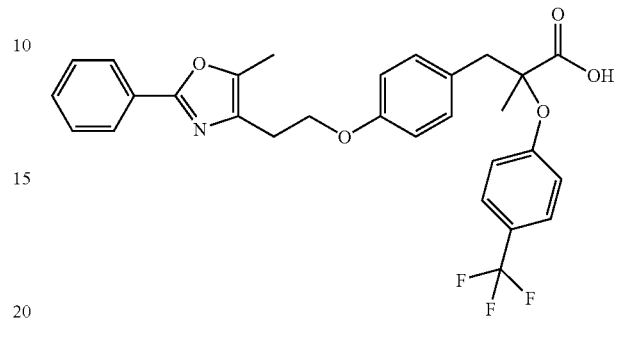

Standard Procedure (B) was utilized to prepare the title compound from 3-(4-hydroxyphenyl)-2-methyl-2-(4-trifluoromethyl-phenoxy)-propionic acid ethyl ester. $^1$H NMR (400 MHz, CDCl$_3$) δ 9.18 (bs, 1H), 7.96 (d, 2H, J=6.8 Hz), 7.52-7.40 (m, 5H), 7.16 (d, 2H, J=8.4 Hz), 6.93 (d, 2H, J=8.8 Hz), 6.80 (d, 2H, J=8.4 Hz), 4.18 (t, 2H, J=6.0 Hz), 3.28 and 3.15 (d of Abq, 2H, J=14.0 Hz), 3.05 (t, 2H, J=6.0 Hz), 2.42 (s, 3H), 1.47 (s, 3H). IR (KBr) 3420, 1734, 1613, 1513, 1328 cm$^{-1}$. HRMS (ES$^+$) m/z exact mass calcd for C$_{29}$H$_{27}$NO$_5$F$_3$ 526.1841, found 526.1851.

Example 51

2-Methyl-3-{4-[2-(5-methyl-2-thiophen-2-yl-oxazol-4-yl)-ethoxy]-phenyl}-2-(4-trifluoromethyl-phenoxy)-propionic acid

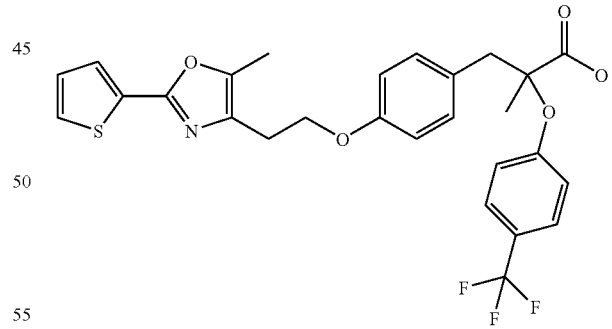

The title compound was prepared from 3-(4-hydroxyphenyl)-2-methyl-2-(4-trifluoromethyl-phenoxy)-propionic acid ethyl ester and toluene-4-sulfonic acid 2-(5-methyl-2-thiophen-2-yl-oxazol-4-yl)-ethyl ester using the procedure of Example 50. $^1$H NMR (400 MHz, CDCl$_3$) δ 8.67 (bs, 1H), 7.66 (d, 1H, J=3.2 Hz), 7.48 (d, 2H, J=8.4 Hz), 7.43 (d, 1H, J=5.0 Hz), 7.16 (d, 2H, J=8.4 Hz), 7.08 (dd, 1H, J=5.0, 3.2 Hz), 6.95 (d, 2H, J=8.4 Hz), 6.80 (d, 2H, J=8.4 Hz), 4.16 (t, 2H, J=6.2 Hz), 3.28 and 3.16 (d of Abq, 2H, J=13.8 Hz), 3.00 (t, 2H, J=6.2 Hz), 2.37 (s, 3H), 1.49 (s, 3H). IR (KBr) 3420, 3000, 1714, 1614, 1513, 1327 cm$^{-1}$. HRMS (ES$^+$) m/z exact mass calcd for $C_{27}H_{25}NO_5F_3S$ 532.1406, found 532.1412.

Example 52

3-{4-[2-(2-Cyclohexyl-5-methyl-oxazol-4-yl)-ethoxy]-phenyl}-2-methyl-2-(4-trifluoromethyl-phenoxy)-propionic acid

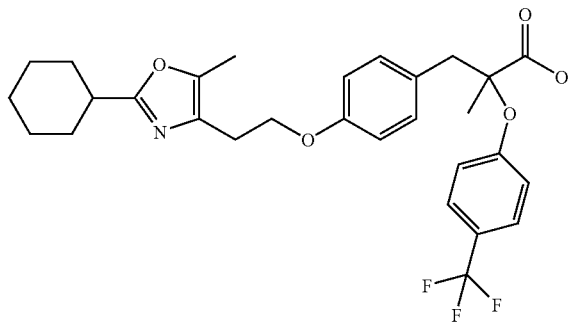

The title compound was prepared from 3-(4-hydroxyphenyl)-2-methyl-2-(4-trifluoromethyl-phenoxy)-propionic acid ethyl ester and toluene-4-sulfonic acid 2-(2-cyclohexyl-5-methyl-oxazol-4-yl)-ethyl ester using the procedure of Example 50. $^1$H NMR (400 MHz, CDCl$_3$) δ 7.48 (d, 2H, J=8.8 Hz), 7.16 (d, 2H, J=8.8 Hz), 6.95 (d, 2H, J=8.4 Hz), 6.78 (d, 2H, J=8.4 Hz), 4.11 (t, 2H, J=6.2 Hz), 3.24 and 3.15 (d of ABq, 2H, J=13.8 Hz), 2.95 (t, 2H, J=6.2 Hz), 2.85 (tt, 1H, J=11.6, 3.4 Hz), 2.30 (s, 3H), 2.03-1.95 (m, 2H), 1.83-1.74 (m, 2H), 1.73-1.68 (m, 1H), 1.58-1.47 (m, 1H), 1.49 (s, 3H), 1.38-1.17 (m, 4H). IR (KBr) 3400, 2937, 1735, 1614, 1513, 1328 cm$^{-1}$. HRMS (ES$^+$) m/z exact mass calcd for $C_{29}H_{33}NO_5F_3$ 532.2311, found 532.2332.

Example 53

2-Methyl-3-(4-{2-[5-methyl-2-(1-methyl-cyclohexyl)-oxazol-4-yl]-ethoxy}-phenyl)-2-(4-trifluoromethyl-phenoxy)-propionic acid

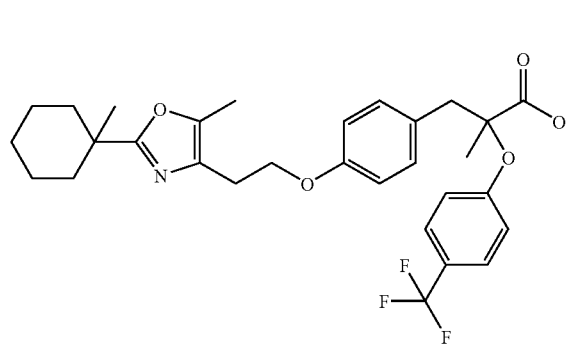

The title compound was prepared from 3-(4-hydroxyphenyl)-2-methyl-2-(4-trifluoromethyl-phenoxy)-propionic acid ethyl ester and toluene-4-sulfonic acid 2-[5-methyl-2-(1-methylcyclohexyl)oxazol-4-yl]-ethyl ester using the procedure of Example 50. $^1$H NMR (400 MHz, CDCl$_3$) δ 7.49 (d, 2H, J=8.60 Hz), 7.15 (d, 2H, J=8.60 Hz), 6.94 (d, 2H, J=8.60 Hz), 6.78 (d, 2H, J=8.60 Hz), 4.13 (t, 2H, J=6.25 Hz), 3.25 (d, 1H, J=14.08 Hz), 3.15 (d, 1H, J=14.08 Hz), 2.99 (t, 2H, J=6.25 Hz), 2.33 (s, 3H), 2.14-2.06 (m, 2H), 1.61-1.41 (m, 8H), 1.49 (s, 3H), 1.30 (s, 3H); MS (ES$^+$) calcd for $C_{30}H_{35}NO_5F_3$: Found m/e 546.3 (M+1, 100%).

Example 54

(S)-3-{4-[2-(2-Cyclohexyl-5-methyl-oxazol-4-yl)-ethoxy]-phenyl}-2-methyl-2-(4-trifluoromethyl-phenoxy)-propionic acid

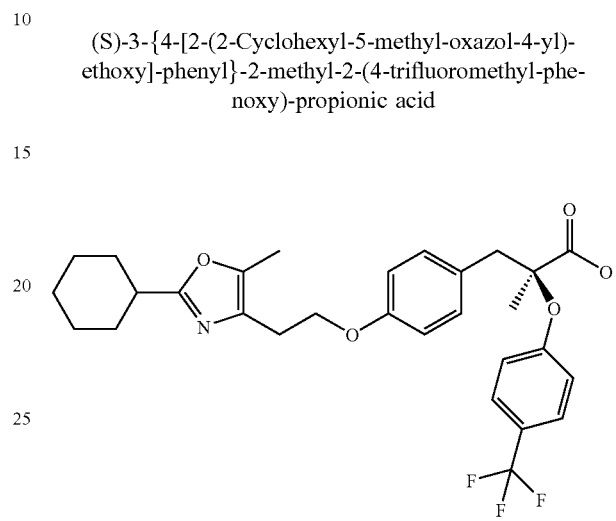

The title compound was prepared from (S)-3-(4-hydroxyphenyl)-2-methyl-2-(4-trifluoromethyl-phenoxy)-propionic acid ethyl ester (95% ee; Chiralpak AD separation, 8×27 cm, 10% IPA/heptane, 275 nm) and toluene-4-sulfonic acid 2-(2-cyclohexyl-5-methyl-oxazol-4-yl)-ethyl ester by the procedure described in Example 1.

Example 55

(S)-2-Methyl-3-{4-[2-(5-methyl-2-thiophen-2-yl-oxazol-4-yl)-ethoxy]-phenyl}-2-(4-trifluoromethyl-phenoxy)-propionic acid

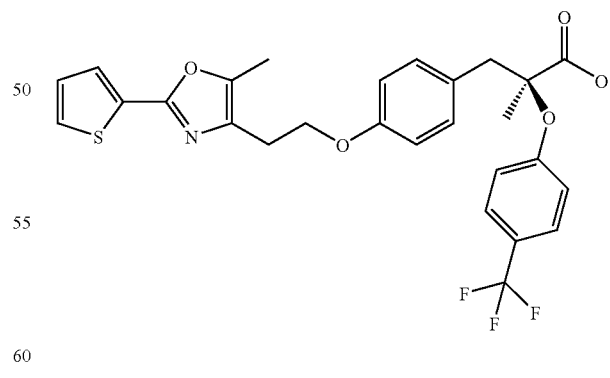

The title compound was prepared from (S)-3-(4-hydroxyphenyl)-2-methyl-2-(4-trifluoromethyl-phenoxy)-propionic acid ethyl ester (95% ee; Chiralpak AD separation, 8×27 cm, 10% IPA/heptane, 275 nm) and toluene-4-sulfonic acid 2-(5-methyl-2-thiophen-2-yl-oxazol-4-yl)-ethyl ester by the procedure described in Example 1.

Example 56

2-(3,4-Difluoro-phenoxy)-2-methyl-3-{4-[2-(5-methyl-2-phenyl-oxazol-4-yl)-ethoxy]-phenyl}-propionic acid

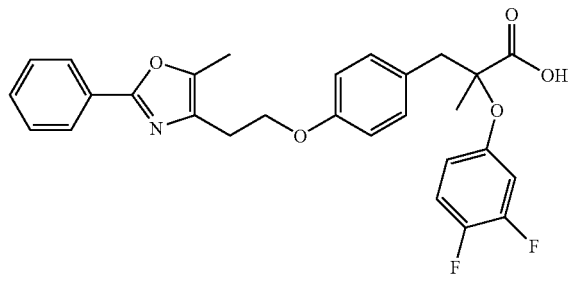

Standard Procedure (B) was utilized to prepare 2-(3,4-difluoro-phenoxy)-2-methyl-3-{4-[2-(5-methyl-2-phenyl-oxazol-4-yl)-ethoxy]-phenyl}-propionic acid from 2-(3,4-difluoro-phenoxy)-3-(4-hydroxy-phenyl)-2-methyl-propionic acid ethyl ester. $^1$H NMR (400 MHz, CDCl$_3$) δ 9.13 (bs, 1H), 7.99-7.95 (m, 2H), 7.48-7.41 (m, 3H), 7.17 (d, 2H, J=8.4 Hz), 6.99 (q, 1H, J=9.5 Hz), 6.82 (d, 2H, J=8.4 Hz), 6.75 (ddd, 1H, J=11.6, 6.4, 2.8 Hz), 6.63-6.56 (m, 1H), 4.20 (t, 2H, J=6.4 Hz), 3.22 and 3.10 (d of ABq, 2H, J=13.8 Hz), 3.04 (t, 2H, J=6.4 Hz), 2.41 (s, 3H), 1.38 (s, 3H).

Example 57

2-(3,4-Difluoro-phenoxy)-2-methyl-3-{4-[2-(5-methyl-2-thiophen-2-yl-oxazol-4-yl)-ethoxy]-phenyl}-propionic acid

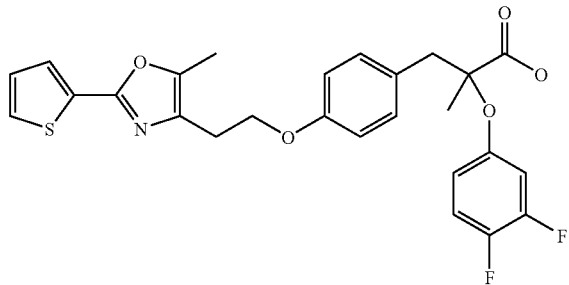

The title compound was prepared from 2-(3,4-difluoro-phenoxy)-3-(4-hydroxy-phenyl)-2-methyl-propionic acid ethyl ester and toluene-4-sulfonic acid 2-(5-methyl-2-thiophen-2-yl-oxazol-4-yl)-ethyl ester using the method of Example 56.

$^1$H NMR (400 MHz, CDCl$_3$) δ 7.61 (d, d, 1H, J=3.6 Hz), 7.39 (d, 1H, J=5.2 Hz), 7.17 (d, 2H, J=8.4 Hz), 7.08 (dd, 1H, J=5.2, 3.6 Hz), 7.00 (q, 1H, J=9.5 Hz), 6.82 (d, 2H, J=8.4 Hz), 6.78 (ddd, 1H, J=11.6, 6.4, 2.8 Hz), 6.65-6.60 (m, 1H), 4.18 (t, 2H, J=6.4 Hz), 3.22 and 3.12 (d of ABq, 2H, J=13.6 Hz), 2.98 (t, 2H, J=6.4 Hz), 2.37 (s, 3H), 1.40 (s, 3H).

Example 58

3-{4-[2-(2-Cyclohexyl-5-methyl-oxazol-4-yl)-ethoxy]-phenyl}-2-(3,4-difluoro-phenoxy)-2-methyl-propionic acid

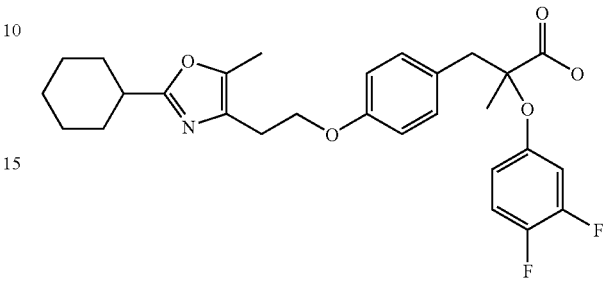

The title compound was prepared from 2-(3,4-difluoro-phenoxy)-3-(4-hydroxy-phenyl)-2-methyl-propionic acid ethyl ester and toluene-4-sulfonic acid 2-(2-cyclohexyl-5-methyl-oxazol-4-yl)-ethyl ester using the method of Example 56. $^1$H NMR (400 MHz, CDCl$_3$) δ 9.37 (bs, 1H), 7.16 (d, 2H, J=8.4 Hz), 6.99 (dd, 1H, J=9.5 Hz), 6.78 (d, 2H, J=8.4 Hz), 6.77-6.72 (m, 1H), 6.63-6.58 (m, 1H), 4.12 (t, 2H, J=6.4 Hz), 3.21 and 3.08 (d of ABq, 2H, J=14.0 Hz), 2.97 (t, 2H, J=6.4 Hz), 2.91 (tt, 1H, J=12.0, 3.6 Hz), 2.32 (s, 3H), 2.04-1.98 (m, 2H), 1.85-1.78 (m, 2H), 1.76-1.68 (m, 1H), 1.62-1.49 (m, 2H), 1.41-1.19 (m, 3H), 1.37 (s, 3H).

Example 59

2-(3,4-Difluoro-phenoxy)-2-methyl-3-(4-{2-[5-methyl-2-(1-methyl-cyclohexyl)-oxazol-4-yl]-ethoxy}-phenyl)-propionic acid

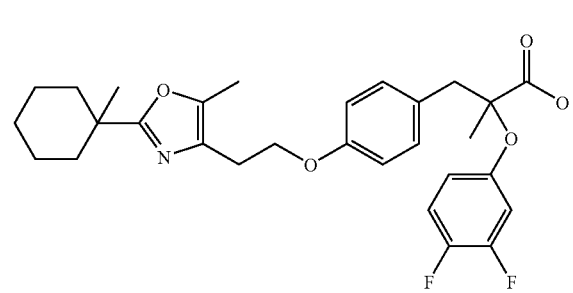

The title compound was prepared from 2-(3,4-difluoro-phenoxy)-3-(4-hydroxy-phenyl)-2-methyl-propionic acid ethyl ester and toluene-4-sulfonic acid 2-[5-methyl-2-(1-methylcyclohexyl)oxazol-4-yl)-ethyl ester using the method of Example 56. $^1$H NMR (400 MHz, CDCl$_3$) δ 7.15 (d, 2H, J=8.60 Hz), 7.00 (q, 1H, J=8.99 Hz), 6.79 (d, 2H, J=8.60 Hz), 6.77-6.74 (m, 1H), 6.63-6.61 (m, 1H), 4.12 (t, 2H, J=6.25 Hz), 3.19 (d, 1H, J=14.08 Hz), 3.09 (d, 1H, J=14.08 Hz), 2.97 (t, 2H, J=6.25 Hz), 2.31 (s, 3H), 2.16-2.08 (m, 2H), 1.61-1.35 (m, 8H), 1.39 (s, 3H), 1.29 (s, 3H); MS (ES$^+$) calcd for C$_{29}$H$_{34}$NO$_5$F$_2$: Found m/e 514.3 (M+1, 100%).

Example 60

2-Methyl-3-{4-[2-(5-methyl-2-phenyl-oxazol-4-yl)-ethoxy]-phenyl}-2-m-tolyloxy-propionic acid

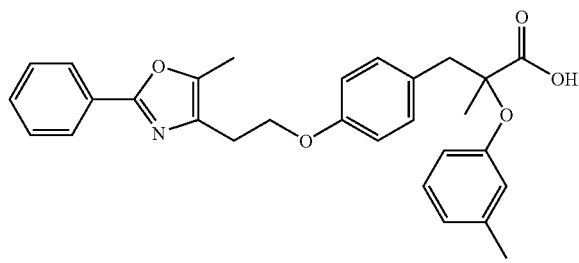

The title compound was prepared from 3-(4-hydroxyphenyl)-2-methyl-2-m-tolyloxy-propionic acid ethyl ester and toluene-4-sulfonic acid 2-(2-phenyl-5-methyl-oxazol-4-yl)-ethyl ester using Standard Procedure (B). $^1$H NMR (400 MHz, CDCl$_3$) δ 8.04-8.01 (m, 2H), 7.47-7.45 (m, 3H), 7.18 (d, 2H, J=8.60 Hz), 7.13 (t, 1H, J=7.82 Hz), 6.87-6.85 (m, 1H), 6.82 (d, 2H, J=8.60 Hz), 6.74-6.67 (m, 2H), 4.23 (t, 2H, J=6.26 Hz), 3.24 (d, 1H, J=13.69 Hz), 3.12 (d, 1H, J=13.69 Hz), 3.06 (t, 2H, J=6.26 Hz), 2.41 (s, 3H), 2.29 (s, 3H), 1.42 (s, 3H); HRMS (ES$^+$) m/z exact mass calcd for C$_{29}$H$_{30}$O$_5$ 472.2124, found 472.2098.

Example 61

2-Methyl-3-{4-[2-(5-methyl-2-thiophen-2-yl-oxazol-4-yl)-ethoxy]-phenyl}-2-m-tolyloxy-propionic acid

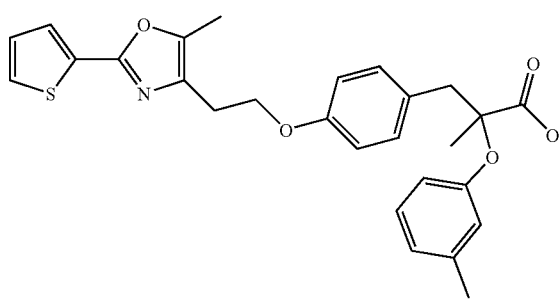

The title compound was prepared from 3-(4-hydroxyphenyl)-2-methyl-2-m-tolyloxy-propionic acid ethyl ester and toluene-4-sulfonic acid 2-(5-methyl-2-thiophen-2-yl-oxazol-4-yl)-ethyl ester using the procedure of Example 60. $^1$H NMR (400 MHz, CDCl$_3$) δ 7.76 (d, 1H, J=3.52 Hz), 7.46 (d, 1H, J=4.69 Hz), 7.17 (d, 2H, J=8.21 Hz), 7.16-7.10 (m, 2H), 6.87-6.86 (m, 1H), 6.81 (d, 2H, J=8.60 Hz), 6.72-6.69 (m, 2H), 4.21 (t, 2H, J=6.26 Hz), 3.24 (d, 1H, J=14.08 Hz), 3.12 (d, 1H, J=14.08 Hz), 3.01 (t, 2H, J=6.26 Hz), 2.38 (s, 3H), 2.30 (s, 3H), 1.41 (s, 3H); HRMS (ES$^+$) m/z exact mass calcd for C$_{27}$H$_{28}$NO$_5$S 478.1688, found 478.1692.

Example 62

3-{4-[2-(2-Cyclohexyl-5-methyl-oxazol-4-yl)-ethoxy]-phenyl}-2-methyl-2-m-tolyloxy-propionic acid

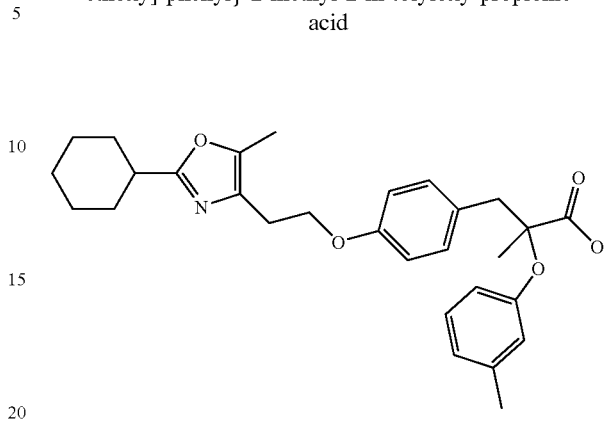

The title compound was prepared from 3-(4-hydroxyphenyl)-2-methyl-2-m-tolyloxy-propionic acid ethyl ester and toluene-4-sulfonic acid 2-(2-cyclohexyl-5-methyl-oxazol-4-yl)-ethyl ester using the procedure of Example 60.

$^1$H NMR (400 MHz, CDCl$_3$) δ 7.17 (d, 2H, J=8.60 Hz), 7.13 (t, 1H, J=7.82 Hz), 6.85 (d, 1H, J=7.43 Hz), 6.78 (d, 2H, J=8.60 Hz), 6.69-6.68 (m, 2H), 4.16 (t, 2H, J=5.86 Hz), 3.20 (d, 1H, J=14.08 Hz), 3.14 (d, 1H, J=14.08 Hz), 3.09-2.96 (m, 3H), 2.33 (s, 3H), 2.30 (s, 3H), 2.06-2.02 (m, 2H), 1.83-1.80 (m, 2H), 1.73-1.70 (m, 1H), 1.59-1.56 (m, 2H), 1.41 (s, 3H), 1.38-1.26 (m, 3H); HRMS (ES$^+$) m/z exact mass calcd for C$_{29}$H$_{36}$NO$_5$ 478.2593, found 478.2592.

Example 63

2-(4-Fluoro-phenoxy)-2-methyl-3-{4-[2-(5-methyl-2-phenyl-oxazol-4-yl)-ethoxy]-phenyl}-propionic acid

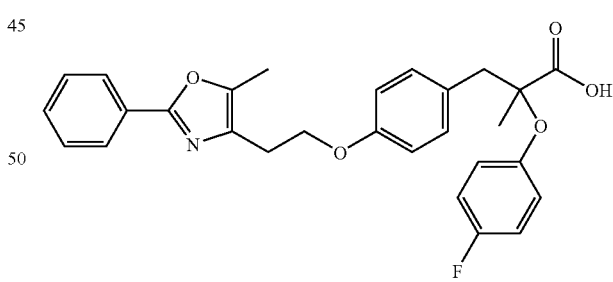

Standard Procedure (B) was utilized to prepare the title compound from 2-(4-fluorophenoxy)-3-(4-hydroxy-phenyl)-2-methyl-propionic acid ethyl ester and toluene-4-sulfonic acid 2-(2-phenyl-5-methyl-oxazol-4-yl)-ethyl ester.

$^1$H NMR (400 MHz, CDCl$_3$) δ 8.00-7.97 (m, 2H), 7.43-7.41 (m, 3H), 7.18 (d, 2H, J=8.99 Hz), 6.93-6.82 (m, 6H), 4.21 (t, 2H, J=6.65 Hz), 3.21 (d, 1H, J=14.08 Hz), 3.13 (d, 1H, J=14.08 Hz), 3.01 (t, 2H, J=6.65 Hz) 2.39 (s, 3H), 1.36 (s, 3H); HRMS (ES$^+$) m/z exact mass calcd for C$_{28}$H$_{27}$NO$_5$F 476.1873, found 476.1871.

Example 64

2-(4-Fluoro-phenoxy)-2-methyl-3-{4-[2-(5-methyl-2-thiophen-2-yl-oxazol-4-yl)-ethoxy]-phenyl}-propionic acid

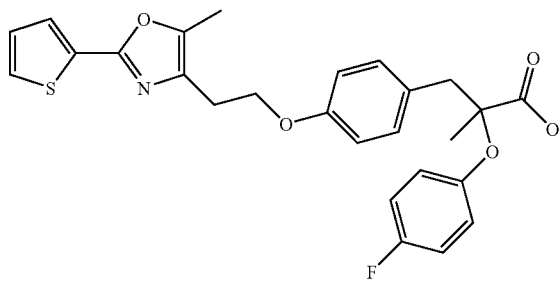

The title compound was prepared from 2-(4-fluorophenoxy)-3-(4-hydroxy-phenyl)-2-methyl-propionic acid ethyl ester and toluene-4-sulfonic acid 2-(5-methyl-2-thiophen-2-yl-oxazol-4-yl)-ethyl ester using the procedure of Example 63. $^1$H NMR (400 MHz, CDCl$_3$) δ 7.58 (dd, 1H, J=3.52 Hz, J=1.17 Hz), 7.36 (dd, 1H, J=5.08 Hz, J=1.17 Hz), 7.18 (d, 2H, J=8.60 Hz), 7.06 (dd, 1H, J=5.08 Hz, J=3.91 Hz), 6.93-6.85 (m, 4H), 6.82 (d, 2H, J=8.60 Hz), 4.18 (t, 2H, J=6.65 Hz), 3.21 (d, 1H, J=13.69 Hz), 3.13 (d, 1H, J=13.69 Hz), 2.96 (t, 2H, J=6.65 Hz), 2.35 (s, 3H), 1.36 (s, 3H); HRMS (ES$^+$) m/z exact mass calcd for C$_{26}$H$_{25}$NO$_5$FS 482.1437, found 482.1451.

Example 65

3-{4-[2-(2-Cyclohexyl-5-methyl-oxazol-4-yl)-ethoxy]-phenyl}-2-(4-fluoro-phenoxy)-2-methyl-propionic acid

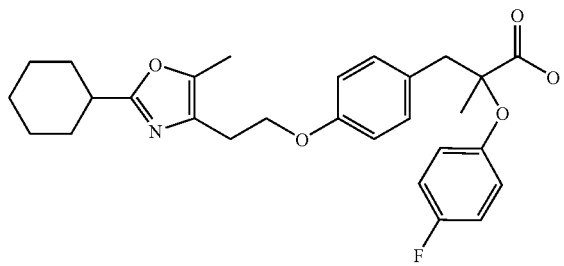

The title compound was prepared from 2-(4-fluorophenoxy)-3-(4-hydroxy-phenyl)-2-methyl-propionic acid ethyl ester and toluene-4-sulfonic acid 2-(2-phenyl-5-methyl-oxazol-4-yl)-ethyl ester using the procedure of Example 63. $^1$H NMR (400 MHz, CDCl$_3$) δ 7.17 (d, 2H, J=8.60 Hz), 6.95-6.85 (m, 4H), 6.79 (d, 2H, J=8.60 Hz), 4.12 (t, 2H, J=6.26 Hz), 3.20 (d, 1H, J=14.08 Hz), 3.11 (d, 1H, J=14.08 Hz), 2.95 (t, 2H, J=6.26 Hz) 2.85 (tt, 1H, J=11.73 Hz, J=3.52 Hz), 2.30 (s, 3H), 2.02-1.99 (m, 2H), 1.83-1.78 (m, 2H), 1.72-1.69 (m, 1H), 1.58-1.49 (m, 2H), 1.36 (s, 3H), 1.33-1.22 (m, 3H); HRMS (ES$^+$) m/z exact mass calcd for C$_{28}$H$_{33}$NO$_5$F 482.2343, found 482.2347.

Example 66

2-(4-Fluoro-phenoxy)-2-methyl-3-(4-{2-[5-methyl-2-(1-methyl-cyclohexyl)-oxazol-4-yl]-ethoxy}-phenyl)-propionic acid

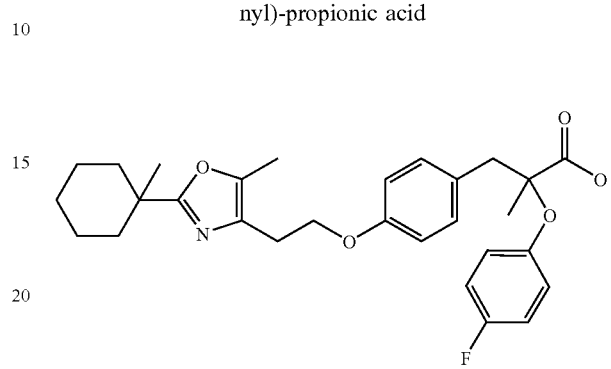

The title compound was prepared from 2-(4-fluorophenoxy)-3-(4-hydroxy-phenyl)-2-methyl-propionic acid ethyl ester and toluene-4-sulfonic acid 2-[5-methyl-2-(1-methyl-cyclohexyl)oxazol-4-yl]-ethyl ester using the procedure of Example 63. $^1$H NMR (400 MHz, CDCl$_3$) δ 7.17 (d, 2H, J=8.60 Hz), 6.93-6.84 (m, 4H), 6.69 (d, 2H, J=8.60 Hz), 4.13 (t, 2H, J=6.06 Hz), 3.22 (d, 1H, J=13.68 Hz), 3.09 (d, 1H, J=13.68 Hz), 2.98 (t, 2H, J=6.06 Hz), 2.31 (s, 3H), 2.17-2.09 (m, 2H), 1.57-1.50 (m, 4H), 1.45-1.37 (m, 4H), 1.35 (s, 3H), 1.31 (s, 3H); MS (ES$^+$) calcd for C$_{29}$H$_{35}$NO$_5$F: Found m/e 496.3 (M+1, 100%).

Example 67

(S)-2-(4-Fluoro-phenoxy)-2-methyl-3-(4-{2-[5-methyl-2-(1-methyl-cyclohexyl)-oxazol-4-yl]-ethoxy}-phenyl)-propionic acid

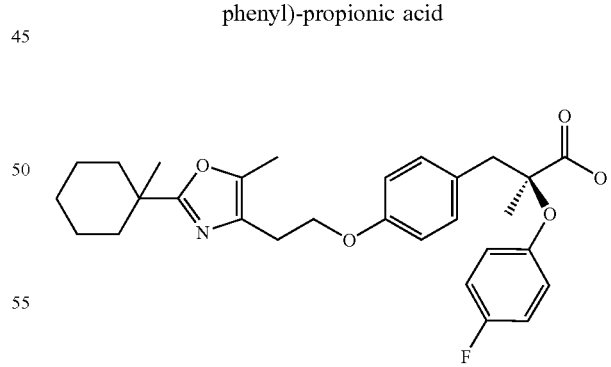

The title compound was prepared from (S)-2-(4-fluorophenoxy)-3-(4-hydroxy-phenyl)-2-methyl-propionic acid ethyl ester and toluene-4-sulfonic acid 2-[5-methyl-2-(1-methylcyclohexyl)-oxazol-4-yl]-ethyl ester (95% ee; Chiralpak AD separation, 8×28 cm, 10% IPA/heptane, 275 nm) by the procedure described in Example 1.

Example 68

(S)-2-(4-Methanesulfonyl-phenoxy)-2-methyl-3-{4-[2-(5-methyl-2-phenyl-oxazol-4-yl)-ethoxy]-phenyl}-propionic acid

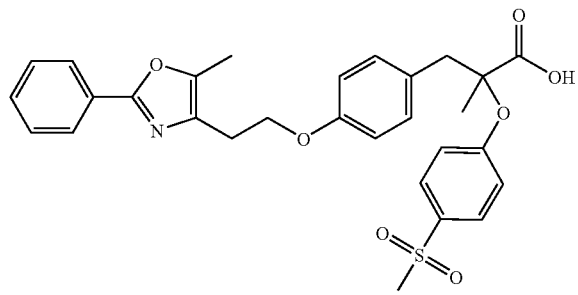

Standard Procedure (B) was utilized to prepare the title compound from 3-(4-hydroxyphenyl)-2-(4-methanesulfonyl-phenoxy)-2-methyl-propionic acid ethyl ester and toluene-4-sulfonic acid 2-(2-phenyl-5-methyl-oxazol-4-yl)-ethyl ester.

$^1$H NMR (400 MHz, CDCl$_3$) δ 8.00 (d, 2H, J=7.04 Hz), 7.80 (d, 2H, J=9.00 Hz), 7.55-7.50 (m, 3H), 7.14 (d, 2H, J=8.60 Hz), 6.97 (d, 2H, J=9.00 Hz), 6.80 (d, 2H, J=8.21 Hz), 4.20 (t, 2H, J=5.87 Hz), 3.29 (d, 1H, J=14.08 Hz), 3.17 (d, 1H, J=14.08 Hz), 3.10 (t, 2H, J=5.87 Hz) 3.01 (s, 3H), 2.46 (s, 3H), 1.54 (s, 3H); HRMS (ES$^+$) m/z exact mass calcd for C$_{29}$H$_{30}$NO$_7$S 536.1743, found 536.1771.

Example 69

2-Methyl-3-{4-[2-(5-methyl-2-phenyl-oxazol-4-yl)-ethoxy]-phenyl}-2-(4-nitro-phenoxy)-propionic acid

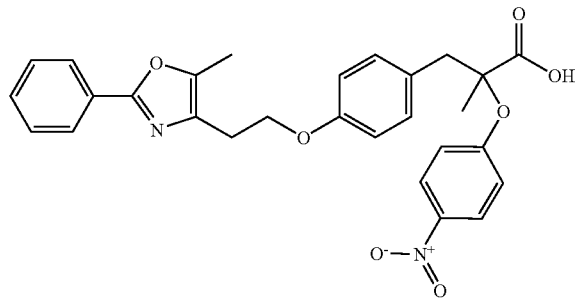

Standard Procedure (B) was utilized to prepare the title compound from toluene-4-sulfonic acid 2-(2-phenyl-5-methyl-oxazol-4-yl)-ethyl ester. $^1$H NMR (400 MHz, CDCl$_3$) δ 8.12 (d, 2H, J=9.00 Hz), 8.05-7.96 (m, 2H), 7.52-7.45 (m, 3H), 7.14 (d, 2H, J=8.60 Hz), 6.90 (d, 2H, J=9.00 Hz), 6.80 (d, 2H, J=8.60 Hz), 4.20 (t, 2H, J=5.87 Hz), 3.29 (d, 1H, J=14.08 Hz), 3.18 (d, 1H, J=14.08 Hz), 3.08 (t, 2H, J=5.87 Hz), 2.45 (s, 3H), 1.55 (s, 3H); HRMS (ES$^+$) m/z exact mass calcd for C$_{28}$H$_{27}$N$_2$O$_7$ 503.1818, found 503.1850.

Example 70

2-Methyl-3-{4-[2-(5-methyl-2-phenyl-oxazol-4-yl)-ethoxy]-phenyl}-2-(3-trifluoromethyl-phenoxy)-propionic acid

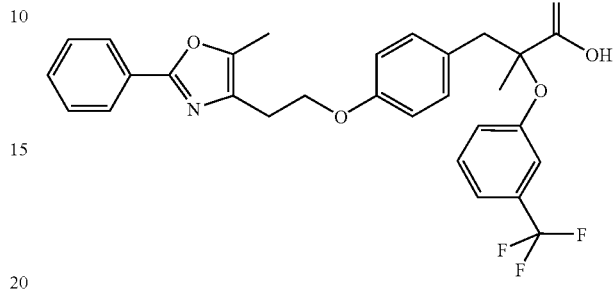

Standard Procedure (B) was utilized to prepare the title compound from 3-(4-hydroxy-phenyl)-2-methyl-2-(3-trifluoromethyl-phenoxy)-propionic acid ethyl ester and toluene-4-sulfonic acid 2-(2-phenyl-5-methyl-oxazol-4-yl)-ethyl ester. $^1$H NMR (400 MHz, CDCl$_3$) δ 7.99-7.97 (m, 2H), 7.50-7.46 (m, 3H), 7.33 (t, 1H, J=8.21 Hz), 7.26-7.24 (m, 1H), 7.17 (d, 2H, J=8.60 Hz), 7.14-7.12 (m, 1H), 7.04-7.01 (m, 1H), 6.81 (d, 2H, J=8.60 Hz), 4.20 (t, 2H, J=5.87 Hz), 3.27 (d, 1H, J=14.08 Hz), 3.14 (d, 1H, J=14.08 Hz), 3.07 (t, 2H, J=5.87 Hz), 2.42 (s, 3H), 1.44 (s, 3H); HRMS (ES$^+$) m/z exact mass calcd for C$_{29}$H$_{27}$NO$_5$F$_3$ 526.1841, found 526.1845.

Example 71

2-Methyl-3-{4-[2-(5-methyl-2-thiophen-2-yl-oxazol-4-yl)-ethoxy]-phenyl}-2-(3-trifluoromethyl-phenoxy)-propionic acid

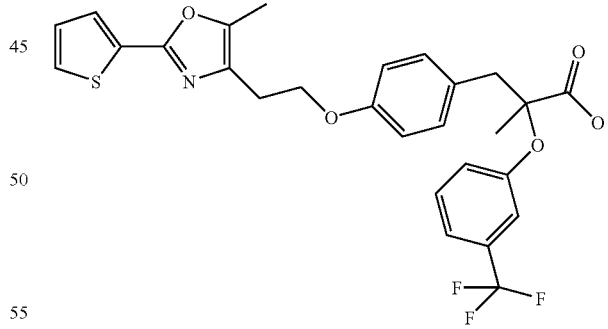

The title compound was prepared from 3-(4-hydroxy-phenyl)-2-methyl-2-(3-trifluoromethyl-phenoxy)-propionic acid ethyl ester using the procedure of Example 70.

$^1$H NMR (400 MHz, CDCl$_3$) δ 7.77 (d, 1H, J=3.51 Hz), 7.47 (d, 1H, J=5.08 Hz), 7.35 (t, 1H, J=8.01 Hz), 7.29-7.27 (m, 1H), 7.19-7.11 (m, 4H), 7.08-7.03 (m, 1H), 6.82 (d, 2H, J=8.60 Hz), 4.18 (t, 2H, J=6.26 Hz), 3.27 (d, 1H, J=14.08 Hz), 3.15 (d, 1H, J=14.08 Hz), 3.02 (t, 2H, J=6.26 Hz), 2.39 (s, 3H), 1.46 (s, 3H); HRMS (ES$^+$) m/z exact mass calcd for C$_{27}$H$_{25}$NO$_5$F$_3$S 532.1405, found 532.1423.

Example 72

3-{4-[2-(2-Cyclohexyl-5-methyl-oxazol-4-yl)-ethoxy]-phenyl}-2-methyl-2-(3-trifluoromethyl-phenoxy)-propionic acid

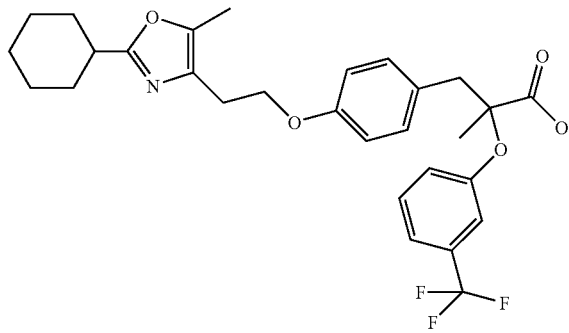

The title compound was prepared from 3-(4-hydroxy-phenyl)-2-methyl-2-(3-trifluoromethyl-phenoxy)-propionic acid ethyl ester using the procedure of Example 70.

$^1$H NMR (400 MHz, CDCl$_3$) δ 7.35 (t, 1H, J=7.82 Hz), 7.28-7.26 (m, 1H), 7.16 (d, 2H, J=8.60 Hz), 7.13-7.12 (m, 1H), 7.05-7.02 (m, 1H), 6.78 (d, 2H, J=8.60 Hz), 4.14 (t, 2H, J=5.67 Hz), 3.26 (d, 1H, J=14.08 Hz), 3.13 (d, 1H, J=14.08 Hz), 3.01-2.93 (m, 3H) 2.35 (s, 3H), 2.05-2.01 (m, 2H), 1.83-1.78 (m, 2H), 1.73-1.69 (m, 1H), 1.58-1.49 (m, 2H), 1.45 (s, 3H), 1.37-1.18 (m, 3H); HRMS (ES$^+$) m/z exact mass calcd for C$_{29}$H$_{33}$NO$_5$F$_3$ 532.2311, found 532.2305.

Example 73

2-Methyl-3-(4-{2-[5-methyl-2-(1-methyl-cyclohexyl)-oxazol-4-yl]-ethoxy}-phenyl)-2-(3-trifluoromethyl-phenoxy)-propionic acid

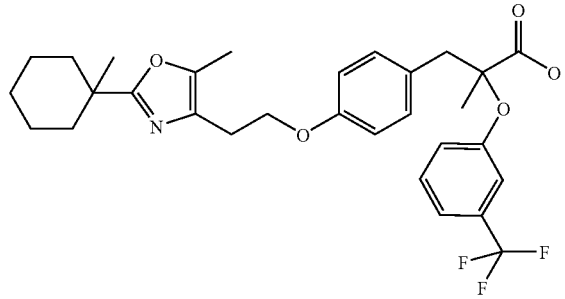

Standard Procedure (B) was utilized to prepare the title compound from toluene-4-sulfonic acid 2-[5-methyl-2-(1-methylcyclohexyl)oxazol-4-yl)ethyl ester. $^1$H NMR (400 MHz, CDCl$_3$) δ 7.34 (t, 1H, J=8.01 Hz), 7.28-7.26 (m, 1H), 7.16 (d, 2H, J=8.60 Hz), 7.13-7.13 (m, 1H), 7.06-7.01 (m, 1H), 6.79 (d, 2H, J=8.60 Hz), 4.14 (t, 2H, J=6.25 Hz), 3.24 (d, 1H, J=14.08 Hz), 3.13 (d, 1H, J=14.08 Hz), 2.99 (t, 2H, J=6.25 Hz), 2.34 (s, 3H), 2.14-2.08 (m, 2H), 1.62-1.32 (m, 8H), 1.45 (s, 3H), 1.31 (s, 3H); MS (ES$^+$) calcd for C$_{30}$H$_{35}$NO$_5$F$_3$: Found m/e 546.2 (M+1, 100%).

Example 74

2-(3-Methoxy-phenoxy)-2-methyl-3-{4-[2-(5-methyl-2-phenyl-oxazol-4-yl)-ethoxy]-phenyl}-propionic acid

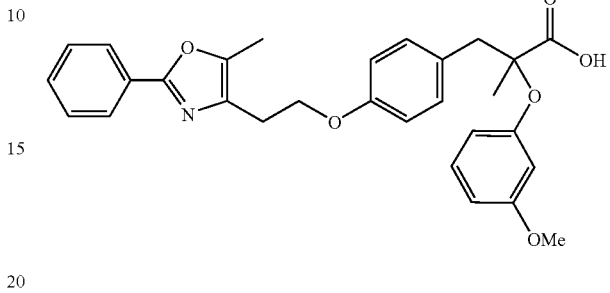

Standard Procedure (B) was utilized to prepare the title compound from 3-(4-hydroxy-phenyl)-2-(3-methoxy-phenoxy)-2-methyl-propionic acid ethyl ester and toluene-4-sulfonic acid 2-(2-phenyl-5-methyl-oxazol-4-yl)-ethyl ester.

$^1$H NMR (400 MHz, CDCl$_3$) δ 7.97-7.95 (m, 2H), 7.42-7.39 (m, 3H), 7.18-7.12 (m, 3H), 6.83 (d, 2H, J=8.99 Hz), 6.61-6.58 (m, 1H), 6.52-6.46 (m, 2H), 4.21 (t, 2H, J=6.65 Hz), 3.74 (s, 3H), 3.25 (d, 1H, J=13.69 Hz), 3.15 (d, 1H, J=13.69 Hz), 2.98 (t, 2H, J=6.65 Hz), 2.37 (s, 3H), 1.45 (s, 3H); HRMS (ES$^+$) m/z exact mass calcd for C$_{29}$H$_{30}$NO$_6$ 488.2073, found 488.2083.

Example 75

2-(3-Methoxy-phenoxy)-2-methyl-3-{4-[2-(5-methyl-2-thiophen-2-yl-oxazol-4-yl)-ethoxy]-phenyl}-propionic acid

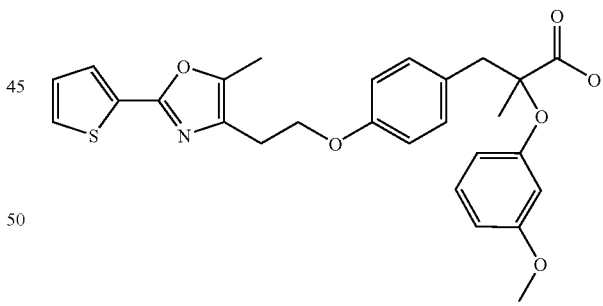

The title compound was prepared from 3-(4-hydroxy-phenyl)-2-(3-methoxy-phenoxy)-2-methyl-propionic acid ethyl ester and toluene-4-sulfonic acid 2-(5-methyl-2-thiophen-2-yl-oxazol-4-yl)-ethyl ester using the procedure of Example 74. $^1$H NMR (400 MHz, CDCl$_3$) δ 7.58 (d, 1H, J=3.52 Hz), 7.36 (d, 1H, J=5.08 Hz), 7.17-7.13 (m, 3H), 7.08-6.99 (m, 1H), 6.82 (d, 2H, J=8.60 Hz), 6.62-6.59 (m, 1H), 6.52-6.46 (m, 2H), 4.19 (t, 2H, J=6.65 Hz), 3.75 (s, 3H), 3.24 (d, 1H, J=14.08 Hz), 3.16 (d, 1H, J=14.08 Hz), 2.95 (t, 2H, J=6.65 Hz), 2.35 (s, 3H), 1.45 (s, 3H); HRMS (ES$^+$) m/z exact mass calcd for C$_{27}$H$_{28}$NO$_6$S 494.1637, found 494.1642.

Example 76

3-{4-[2-(2-Cyclohexyl-5-methyl-oxazol-4-yl)-ethoxy]-phenyl}-2-(3-methoxy-phenoxy)-2-methyl-propionic acid

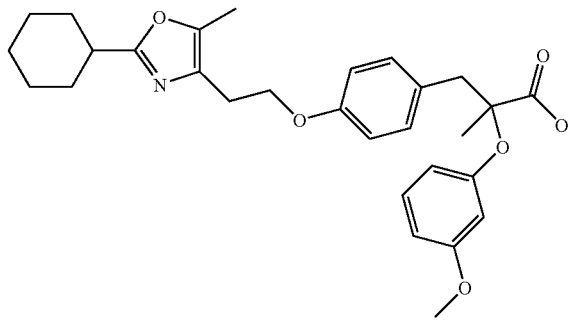

The title compound was prepared from 3-(4-hydroxy-phenyl)-2-(3-methoxy-phenoxy)-2-methyl-propionic acid ethyl ester and toluene-4-sulfonic acid 2-(2-cyclohexyl-5-methyl-oxazol-4-yl)-ethyl ester using the procedure of Example 74.

$^1$H NMR (400 MHz, CDCl$_3$) δ 7.17-7.12 (m, 3H), 6.77 (d, 2H, J=8.99 Hz), 6.61-6.59 (m, 1H), 6.50-6.47 (m, 1H), 6.46 (t, 1H, J=2.35 Hz), 4.14 (t, 2H, J=6.06 Hz), 3.75 (s, 3H), 3.25 (d, 1H, J=14.08 Hz), 3.13 (d, 1H, J=14.08 Hz), 3.00-2.94 (m, 3H), 2.33 (s, 3H), 2.05-2.01 (m, 2H), 1.83-1.80 (m, 2H), 1.75-1.69 (m, 1H), 1.58-1.54 (m, 2H), 1.44 (s, 3H), 1.37-1.26 (m, 3H); HRMS (ES$^+$) m/z exact mass calcd for C$_{29}$H$_{36}$NO$_6$ 494.2543, found 494.2543.

Example 77

2-(3-Methoxy-phenoxy)-2-methyl-3-(4-{2-[5-methyl-2-(1-methyl-cyclohexyl)-oxazol-4-yl]-ethoxy}-phenyl)-propionic acid

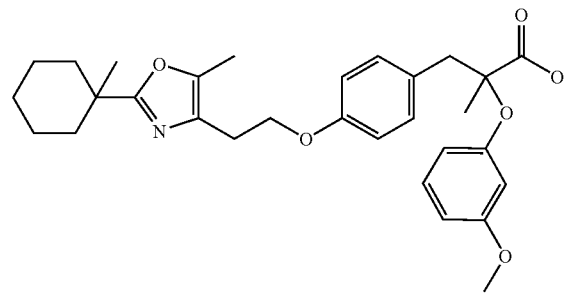

The title compound was prepared from 3-(4-hydroxy-phenyl)-2-(3-methoxy-phenoxy)-2-methyl-propionic acid ethyl ester and toluene-4-sulfonic acid 2-[5-methyl-2-(1-methylcyclohexyl)oxazol-4-yl]-ethyl ester using the procedure of Example 74. $^1$H NMR (400 MHz, CDCl$_3$) δ 7.16-7.13 (m, 3H), 6.79 (d, 2H, J=8.60 Hz), 6.61-6.59 (m, 1H), 6.51-6.48 (m, 1H), 6.46 (t, 1H, J=2.35 Hz), 4.13 (t, 2H, J=6.25 Hz), 3.75 (s, 3H), 3.24 (d, 1H, J=13.68 Hz), 3.12 (d, 1H, J=13.68 Hz), 2.96 (t, 2H, J=6.25 Hz), 2.30 (s, 3H), 2.15-2.08 (m, 2H), 1.61-1.45 (m, 5H), 1.44 (s, 3H), 1.43-1.36 (m, 3H), 1.30 (s, 3H); MS (ES$^+$) calcd for C$_{30}$H$_{38}$NO$_6$: Found m/e 508.3 (M+1, 100%).

Example 78

2-(Benzo[1,3]dioxol-5-yloxy)-2-methyl-3-{4-[2-(5-methyl-2-phenyl-oxazol-4-yl)-ethoxy]-phenyl}-propionic acid

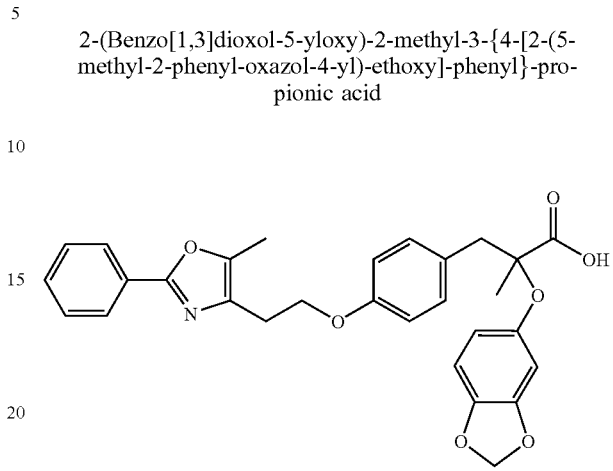

Standard Procedure (B) was utilized to prepare the title compound from 2-(benzo[1,3]dioxol-5-yloxy)-3-(4-hydroxy-phenyl)-2-methyl-propionic acid ethyl ester and toluene-4-sulfonic acid 2-(2-phenyl-5-methyl-oxazol-4-yl)-ethyl ester. $^1$H NMR (400 MHz, CDCl$_3$) δ 7.96-7.93 (m, 2H), 7.44-7.41 (m, 3H), 7.13 (d, 2H, J=8.79 Hz), 6.78 (d, 2H, J=8.79 Hz), 6.60 (d, 1H, J=8.79 Hz), 6.41 (d, 1H, J=2.44 Hz), 6.32 (dd, 1H, J=8.79 Hz, J=2.44 Hz), 5.88 (d, 2H, J=0.98 Hz), 4.17 (t, 2H, J=6.35 Hz), 3.15 (d, 1H, J=14.16 Hz), 3.04-3.00 (m, 3H), 2.38 (s, 3H), 1.30 (s, 3H); HRMS (ES$^+$) m/z exact mass calcd for C$_{29}$H$_{28}$NO$_7$ 502.1866, found 502.1881.

Example 79

2-(Benzo[1,3]dioxol-5-yloxy)-2-methyl-3-{4-[2-(5-methyl-2-thiophen-2-yl-oxazol-4-yl)-ethoxy]-phenyl}-propionic acid

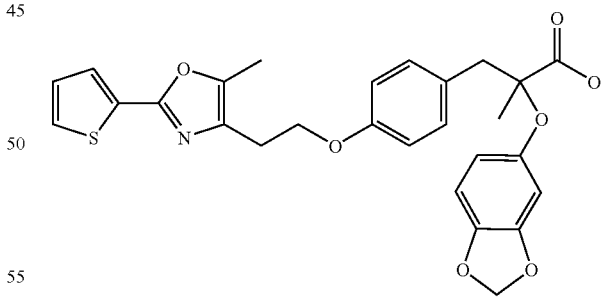

The title compound was prepared from 2-(benzo[1,3] dioxol-5-yloxy)-3-(4-hydroxy-phenyl)-2-methyl-propionic acid ethyl ester and toluene-4-sulfonic acid 2-(5-methyl-2-thiophen-2-yl-oxazol-4-yl)-ethyl ester using the procedure of Example 78. $^1$H NMR (400 MHz, CDCl$_3$) δ 7.57 (dd, 1H, J=3.90 Hz, J=1.47 Hz), 7.35 (dd, 1H, J=5.37 Hz, J=1.47 Hz), 7.13 (d, 2H, J=8.31 Hz), 7.04 (dd, 1H, J=5.37 Hz, J=3.90 Hz), 6.78 (d, 2H, J=8.79 Hz), 6.60 (d, 1H, J=8.30 Hz), 6.42 (d, 1H, J=2.44 Hz), 6.33 (dd, 1H, J=8.31 Hz, J=2.44 Hz), 5.88 (d, 2H, J=0.98 Hz), 4.15 (t, 2H, J=6.35 Hz), 3.16 (d, 1H, J=13.92 Hz), 3.04 (d, 1H, J=13.92 Hz), 2.93 (t, 2H, J=6.35 Hz), 2.31 (s, 3H), 1.30 (s, 3H); HRMS (ES$^+$) m/z exact mass calcd for $C_{27}H_{26}NO_7S$ 508.1430, found 508.1425.

Example 80

2-(Benzo[1,3]dioxol-5-yloxy)-3-{4-[2-(2-cyclohexyl-5-methyl-oxazol-4-yl)-ethoxy]-phenyl}-2-methyl-propionic acid

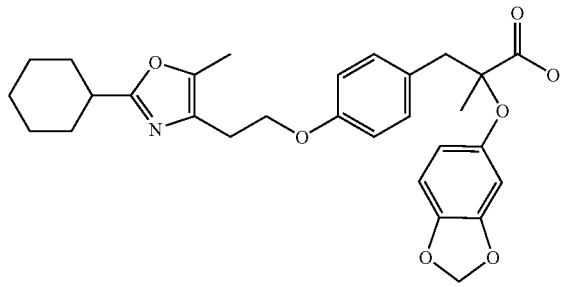

The title compound was prepared from 2-(benzo[1,3] dioxol-5-yloxy)-3-(4-hydroxy-phenyl)-2-methyl-propionic acid ethyl ester and toluene-4-sulfonic acid 2-(2-cyclohexyl-5-methyl-oxazol-4-yl)-ethyl ester using the procedure of Example 78. $^1$H NMR (400 MHz, CDCl$_3$) δ 7.13 (d, 2H, J=8.30 Hz), 6.75 (d, 2H, J=8.79 Hz), 6.61 (d, 2H, J=8.30 Hz), 6.42 (d, 2H, J=2.44 Hz), 6.33 (dd, 1H, J=8.30, J=2.44 Hz), 5.88 (d, 2H, J=0.98 Hz), 4.11 (t, 2H, J=5.86 Hz), 3.15 (d, 1H, J=13.68 Hz), 3.03 (d, 1H, J=13.68 Hz), 2.93 (t, 2H, J=5.86 Hz), 2.86 (tt, 1H, J=11.72 Hz, J=3.42 Hz), 2.27 (s, 3H), 1.99-1.96 (m, 2H), 1.80-1.75 (m, 2H), 1.71-1.65 (m, 1H), 1.57-1.46 (m, 2H), 1.37-1.33 (m, 1H), 1.32 (s, 3H), 1.29-1.19 (m, 2H); HRMS (ES$^+$) m/z exact mass calcd for $C_{29}H_{34}NO_7$ 508.2335, found 508.2351.

Example 81

2-(Benzo[1,3]dioxol-5-yloxy)-2-methyl-3-(4-{2-[5-methyl-2-(1-methyl-cyclohexyl)-oxazol-4-yl]-ethoxy}-phenyl)-propionic acid

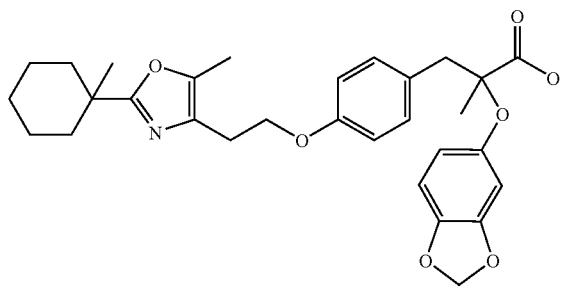

The title compound was prepared from 2-(benzo[1,3] dioxol-5-yloxy)-3-(4-hydroxy-phenyl)-2-methyl-propionic acid ethyl ester and toluene-4-sulfonic acid 2-[5-methyl-2-(1-methylcyclohexyl)oxazol-4-yl]-ethyl ester using the procedure of Example 78. $^1$H NMR (400 MHz, CDCl$_3$) δ 7.17 (d, 2H, J=8.60 Hz), 6.79 (d, 2H, J=8.60 Hz), 6.65 (d, 1H, J=8.21 Hz), 6.47 (d, 1H, J=2.35 Hz), 6.37 (dd, 1H, J=8.21 Hz, J=2.35 Hz), 5.92 (d, 2H, J=0.78 Hz), 4.14 (t, 2H, J=6.25 Hz), 3.19 (d, 1H, J=14.08 Hz), 3.07 (d, 1H, J=14.08 Hz), 2.98 (t, 2H, J=6.25 Hz), 2.31 (s, 3H), 2.17-2.08 (m, 2H), 1.62-1.35 (m, 8H), 1.34 (s, 3H), 1.31 (s, 3H); MS (ES$^+$) calcd for $C_{30}H_{35}NO_7$: Found m/e 522.3 (M+1, 100%).

Example 82

2-{4-[2-(5-Methyl-2-phenyl-oxazol-4-yl)-ethoxy]-benzyl}-2-phenoxy-hexanoic acid

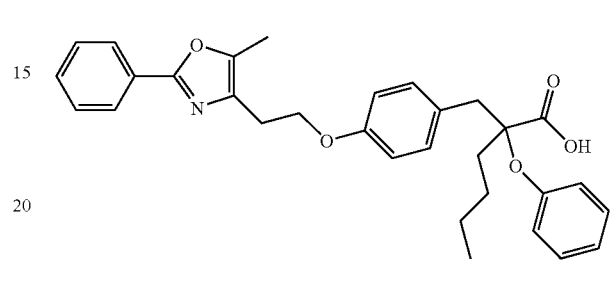

Standard Procedure (B) was utilized to prepare the title compound from 2-(4-hydroxybenzyl)-2-phenoxy-hexanoic acid ethyl ester and toluene-4-sulfonic acid 2-(2-phenyl-5-methyl-oxazol-4-yl)-ethyl ester. $^1$H NMR (400 MHz, CDCl$_3$) δ 7.97-7.94 (m, 2H), 7.42-7.40 (m, 3H), 7.31-7.27 (m, 2H), 7.06 (t, 1H, J=7.43 Hz), 6.98 (t, 4H, J=8.99 Hz), 6.75 (d, 2H, J=8.60 Hz), 4.17 (t, 2H, J=6.65 Hz), 3.29 (s, 2H), 2.96 (t, 2H, J=6.65 Hz), 2.36 (s, 3H), 2.10-1.98 (m, 2H), 1.42-1.16 (m, 4H), 0.79 (t, 3H, J=7.04 Hz); MS (ES$^+$) calcd for $C_{31}H_{34}NO_5$: Found m/e 500.2 (M+1, 100%).

Example 83

2-{4-[2-(5-Methyl-2-thiophen-2-yl-oxazol-4-yl)-ethoxy]-benzyl}-2-phenoxy-hexanoic acid

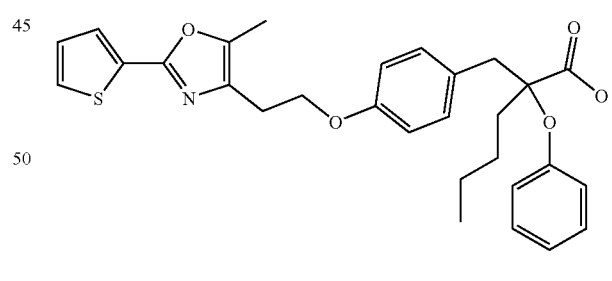

The title compound was prepared from from 2-(4-hydroxybenzyl)-2-phenoxy-hexanoic acid ethyl ester and what following the procedure of Example 84. $^1$H NMR (400 MHz, CDCl$_3$) δ 7.49 (dd, 1H, J=3.91 Hz, J=1.17 Hz), 7.28 (dd, 1H, J=5.08 Hz, J=1.17 Hz), 7.21 (dd, 2H, J=8.60 Hz, J=7.43), 6.99-6.95 (m, 2H), 6.92-6.87 (m, 4H), 6.66 (d, 2H, J=8.60 Hz), 4.07 (t, 2H, J=6.65 Hz), 3.21 (s, 2H), 2.85 (t, 2H, J=6.65 Hz), 2.26 (s, 3H), 2.02-1.88 (m, 2H), 1.32-1.09 (m, 4H), 0.71 (t, 3H, J=7.04 Hz); MS (ES$^+$) calcd for $C_{29}H_{32}NO_5S$: Found m/e 506.2 (M+1, 100%).

Example 84

2-{4-[2-(2-Cyclohexyl-5-methyl-oxazol-4-yl)-ethoxy]-benzyl}-2-phenoxy-hexanoic acid

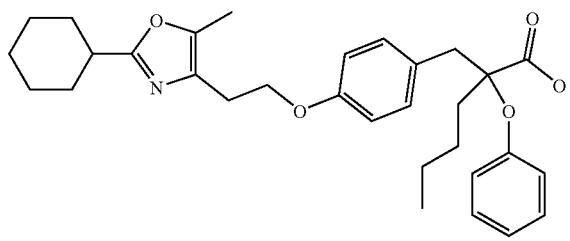

The title compound was prepared from from 2-(4-hydroxybenzyl)-2-phenoxy-hexanoic acid ethyl ester and what following the procedure of Example 82. $^1$H NMR (400 MHz, CDCl$_3$) δ 7.29 (dd, 2H, J=8.60 Hz, J=7.43 Hz), 7.06-6.94 (m, 5H), 6.70 (d, 2H, J=8.60 Hz), 4.09 (t, 2H, J=5.86 Hz), 3.30 (d, 1H, J=14.65 Hz), 3.27 (d, 1H, J=14.65 Hz), 2.95-2.86 (m, 3H), 2.30 (s, 3H), 2.08-1.92 (m, 4H), 1.83-1.79 (m, 2H), 1.72-1.69 (m, 1H), 1.60-1.50 (m, 2H), 1.42-1.18 (m, 7H), 0.71 (t, 3H, J=7.04 Hz); MS (ES$^+$) calcd for C$_{31}$H$_{40}$NO$_5$: Found m/e 506.3 (M+1, 100%).

Example 85

2-(4-{2-[5-Methyl-2-(1-methyl-cyclohexyl)-oxazol-4-yl]-ethoxy}-benzyl)-2-phenoxy-hexanoic acid

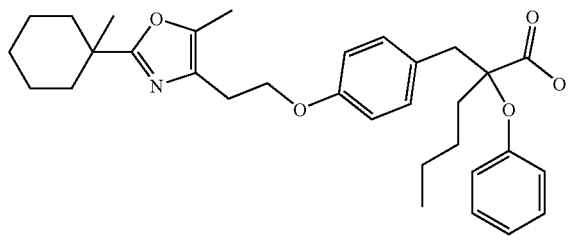

The title compound was prepared from from 2-(4-hydroxybenzyl)-2-phenoxy-hexanoic acid ethyl ester and what following the procedure of Example 82. $^1$H NMR (400 MHz, CDCl$_3$) δ 7.29 (t, 2H, J=8.01 Hz), 7.06 (t, 1H, J=7.43 Hz), 7.00-6.95 (m, 4H), 6.71 (d, 2H, J=8.60 Hz), 4.10 (t, 2H, J=5.86 Hz), 3.28 (s, 2H), 2.96 (t, 2H, J=5.86 Hz), 2.30 (s, 3H), 2.13-1.95 (m, 4H), 1.62-1.15 (m, 12H), 1.31 (s, 3H), 0.79 (t, 3H, J=7.04 Hz); MS (ES$^+$) calcd for C$_{32}$H$_{42}$NO$_5$: Found m/e 520.3 (M+1, 100%).

Example 86

(S)-2-Methyl-3-{4-[2-(5-methyl-2-phenethyl-oxazol-4-yl)-ethoxy]-phenyl}-2-phenoxy-propionic acid

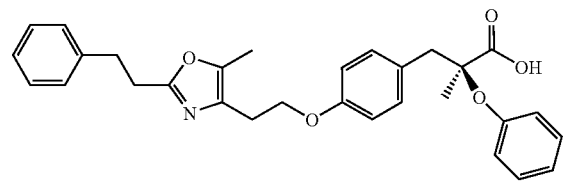

Step A 2-(3-Phenyl-propionylamino)-succinic acid 4-methyl ester

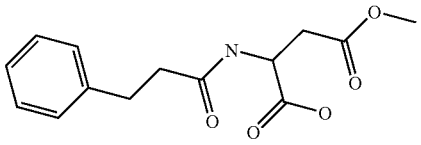

Methyl L-aspartate (15.0 g, 0.082 mol), DI water (245 mL), acetone (20 mL), and Na$_2$CO$_3$ (30.8 g, 0.286 mol) were combined and cooled the solution to 5° C. 3-Phenyl-propionyl chloride (13.3 mL, 0.089 mol) was added dropwise via addition funnel over 10 min. The reaction was allowed to warm to ambient temperature and stir for 2 h. The reaction became very thick during this time. Added conc. HCl (50 mL) to the slurry until the pH was ≦4.0. The reaction mixture was extracted with CH$_2$Cl$_2$ (3×). The organic phase was washed with water and then dried (MgSO$_4$), filtered and concentrated under reduced pressure. The clear, colorless oil was used without further purification. $^1$H NMR (400 MHz, CDCl$_3$) δ 7.92 (br s, 1H), 7.28-7.17 (m, 5H), 6.57 (d, J=7.6 Hz, 1H), 4.87 (m, 1H), 3.67 (s, 3H), 2.96 (t, J=7.6 Hz, 2H), 2.89 (A of ABX, J$_{AB}$=17.6 Hz, J$_{AX}$=4.8 Hz, 1H), 2.88 (B of ABX, J$_{BA}$=17.6 Hz, J$_{BX}$=4.0 Hz, 1H), 2.69 (t, J=7.6 Hz, 2H); MS (EI+) 280 (M+H), 302 (M+H+Na).

Step B

4-Oxo-3-(3-phenyl-propionylamino)-pentanoic acid methyl ester

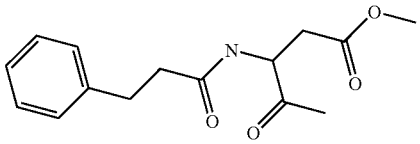

2-(3-Phenyl-propionylamino)-succinic acid 4-methyl ester (10 g, 36 mmol), pyridine (50 mL) and acetic anhydride (45 mL) were combined in a 500 mL flask. The reaction mixture was heated at 90° C. for 2 h and then cooled to ambient temperature. After concentrating the reaction mixture under reduced pressure, DI water was added (100 mL). (Potential exotherm!). The reaction mixture was partitioned between water and CH$_2$Cl$_2$. The organic phase was washed with 1N HCl and then dried (MgSO$_4$), filtered and concentrated under reduced pressure. The material was used without further purification. $^1$H NMR (400 MHz, CDCl$_3$) δ 7.31-7.20 (m, 5H), 6.79 (br d, J=7.6 Hz, 1H), 4.72 (X of ABX, 1H), 3.65 (s, 3H), 3.01-2.93 (m, 3H), 2.71-2.62 (m, 3H), 2.11 (s, 3H); MS (EI) 278.1 (M+H).

Step C (5-Methyl-2-phenethyl-oxazol-4-yl)-acetic acid methyl ester

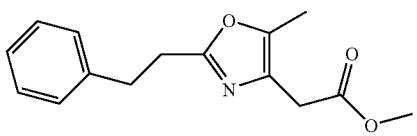

In a 100 mL flask, 4-oxo-3-(3-phenyl-propionylamino)-pentanoic acid methyl ester (10 g, 36 mmol), and acetic anhydride (28 mL) were combined. Following addition of concentrated $H_2SO_4$ (1 mL), the solution was heated to 90° C. for 30 min and then cooled to ambient temperature. The reaction was slowly diluted with DI water (30 mL, potential exotherm). The reaction mixture was partitioned between $CH_2Cl_2$ and water. The organic phase was washed with DI water, 10% $NaHCO_3$ (aq), brine (150 mL), and then dried over $MgSO_4$ and concentrated to obtain a brown oil. The residue was purified by column chromatography (600 mL $SiO_2$, 35% EtOAc/hexanes) to provide the desired product (3.25 g) as a pale yellow oil. $^1$H NMR (400 MHz, $CDCl_3$) δ 7.33-7.20 (m, 5H), 3.72 (s, 3H), 3.47 (s, 2H), 3.08-2.96 (m, 4H), 2.24 (s, 3H); MS (EI+) 260 (M+H).

Step D (5-Methyl-2-phenethyl-oxazol-4-yl)-acetic acid

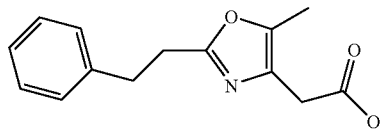

(5-Methyl-2-phenethyl-oxazol-4-yl)-acetic acid methyl ester (8.75 g, 33.8 mmol), in MeOH (120 mL) was treated with 5N NaOH (40 mL) and then the solution was warmed to 40° C. After 40 min, the reaction mixture was concentrated under reduced pressure, suspended in water, and then acidified to pH=1 with 5N HCl. The mixture was extracted with EtOAc (2×), dried ($MgSO_4$), and concentrated to provide 5.25 g (63%) of the product as an off-white solid. $^1$H NMR (400 MHz, $CDCl_3$) ••$^1$H NMR (400 MHz, $CDCl_3$) δ 7.33-7.20 (m, 5H), 3.52 (s, 2H), 3.06-3.03 (m, 4H), 2.24 (s, 3H).

Step E 2-(5-Methyl-2-phenethyl-oxazol-4-yl)-ethanol

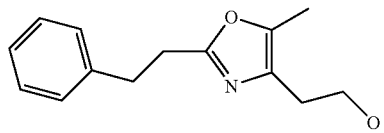

$BH_3$-THF complex (49 mL of a 1.0 M solution in THF) was added dropwise via addition funnel over 50 min to a solution of (5-methyl-2-phenethyl-oxazol-4-yl)-acetic acid (5.05 g, 20.6 mmol) in THF (35 mL). The reaction mixture was stirred at ambient temperature for 3 h, and then quenched with MeOH (12 mL). After heating at 50° C. for 2 h, the reaction mixture was cooled to ambient temperature, and then partitioned between $CH_2Cl_2$ and 1N NaOH. The organic phase was washed with brine (1×50 mL), dried over $MgSO_4$ and concentrated to obtain a residue which was purified by column chromatography (500 mL $SiO_2$, 35% EtOAc/hexanes) to provide 3.99 g (84%) of the desired product as a clear, colorless oil. $^1$H NMR (400 MHz, $CDCl_3$) δ 7.33-7.20 (m, 5H), 3.84 (q, J=5.6 Hz, 2H), 3.06-2.67 (m, 4H), 2.62 (t, J=5.6 Hz, 2H), 2.22 (s, 3H); MS (EI+) 232.19 (M+H); 254.15 (M+H+Na).

Step F

Toluene-4-sulfonic acid 2-(5-methyl-2-phenethyl-oxazol-4-yl)-ethyl ester

A solution of 2-(5-methyl-2-phenethyl-oxazol-4-yl)-ethanol (1.2 g, 5.19 mmol) in $CH_2Cl_2$ at 0° C. was treated with pyridine (1.64 g, 20.7 mmol, 1.68 mL), DMAP (190 mg, 1.56 mmol), and tosyl anhyride (2.2 g, 6.75 mmol). The reaction was warmed to ambient temperature and, after 90 min, the solution was filtered through a pad of silica gel (rinsed with $CH_2Cl_2$). The product was used without further purification. $^1$H NMR (400 MHz, $CDCl_3$) δ 7.73 (d, J=8.4 Hz, 2H), 7.31-7.17 (m, 7H), 4.21 (t, J=6.8 Hz, 2H), 3.01-2.88 (m, 4H), 2.75 (t, J=6.8 Hz, 2H), 2.43 (s, 3H), 2.19 (s, 3H).

Step G (S)-2-Methyl-3-{4-[2-(5-methyl-2-phenethyl-oxazol-4-yl)-ethoxy]-phenyl}-2-phenoxy-propionic acid ethyl ester

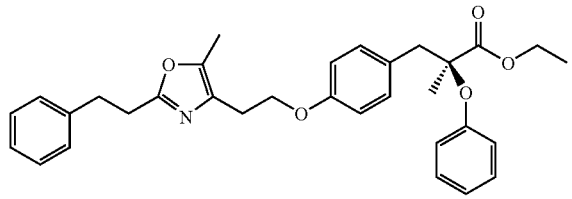

(S)-3-(4-Hydroxyphenyl)-2-methyl-2-phenoxypropionic acid ethyl ester (298 mg, 1.0 mmol), toluene-4-sulfonic acid 2-(5-methyl-2-phenethyl-oxazol-4-yl)-ethyl ester (460 mg, 1.19 mmol) and $Cs_2CO_3$ (388 mg, 1.19 mmol) are combined in anhydrous DMF (8 mL) and stirred for 16 h at 55° C. under an atmosphere of nitrogen. The mixture was then cooled and diluted with ethyl acetate (50 mL), and washed with water then brine. The organic layer was dried with $MgSO_4$ and concentrated in vacuo to a viscous tan oil. The residue was purified by flash column chromatography (200 g silica, hexanes to 25% EtOAc/hexanes) to provide unreacted phenol (80 mg) and the title compound as a colorless oil (340 mg, 67% (91% based on recovered phenol)). $^1$H NMR (400 MHz, $CDCl_3$) δ 7.31-7.17 (m, 9H), 6.98 (tt, J=7.2, 1.2 Hz, 1H), 6.87-6.83 (m, 4H), 4.22 (q, J=7.2 Hz, 2H), 4.17 (t, J=6.8 Hz, 2H), 3.29 (A of Abq, J=14.0 Hz, 1H), 3.13 (B of Abq, J=14.0 Hz, 1H), 3.01-2.97 (m, 4H), 2.89 (t, J=6.8 Hz, 2H), 2.26 (s, 3H), 1.42 (s, 3H), 1.23 (t, J=7.2 Hz, 3H); MS (EI+) 514.27 (M+H).

Step H

(S)-2-Methyl-3-{4-[2-(5-methyl-2-phenethyl-oxazol-4-yl)-ethoxy]-phenyl}-2-phenoxy-propionic acid

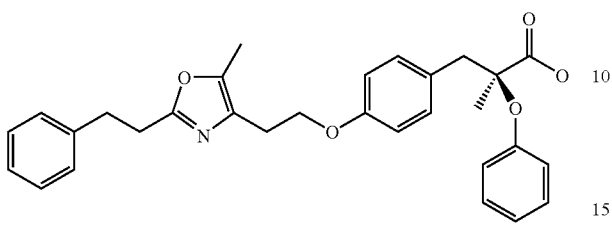

(S)-2-Methyl-3-{4-[2-(5-methyl-2-phenethyl-oxazol-4-yl)-ethoxy]-phenyl}-2-phenoxy-propionic acid ethyl ester (340 mg, 0.66 mmol) in MeOH (10 mL) was treated with 2N NaOH (10 mL) and warmed to 55° C. After 18 h, the mixture was concentrated under reduced pressure and then acidified with 5N HCl to pH=1. The solution was extracted with EtOAc and then the organic phases dried (MgSO$_4$), filtered and concentrated to a white foam (273 mg, 85%): $^1$H NMR (400 MHz, CDCl$_3$) δ 9.00 (br s, 1H), 7.27-7.15 (m, 9H), 6.95 (t, J=7.3 Hz, 1H), 6.91 (d, J=7.7 Hz, 2H), 6.78 (d, J=7.7 Hz, 2H), 4.10 (t, J=6.2 Hz, 2H), 3.27 (A of ABq, J=13.9 Hz, 1H), 3.13 (B of ABq, J=13.9 Hz, 1H), 3.04 (s, 4H), 2.89 (t, J=6.2 Hz, 2H), 2.26 (s, 3H), 1.41 (s, 3H); MS (EI+) 486.1 (M+H), (EI−) 484.1 (M−H).

Example 87

2-Methyl-3-{4-[2-(5-methyl-2-phenethyl-oxazol-4-yl)-ethoxy]-phenyl}-2-phenoxy-propionic acid

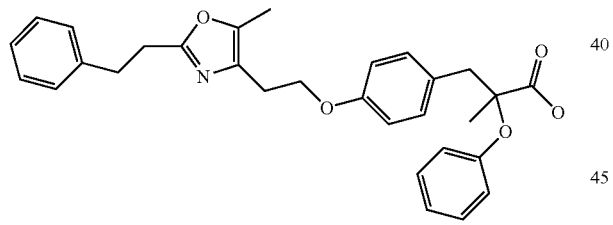

Step A

2-Methyl-3-{4-[2-(5-methyl-2-phenethyl-oxazol-4-yl)-ethoxy]-phenyl}-2-phenoxy-propionic acid ethyl ester

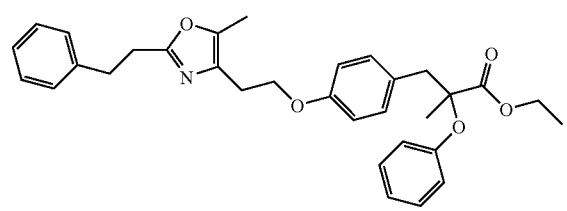

Racemic 3-(4-hydroxyphenyl)-2-methyl-2-phenoxypropionic acid ethyl ester was coupled by the procedure of Example 88, Step G, to provide the title compound. $^1$H NMR (400 MHz, CDCl$_3$) δ 7.29-7.19 (m, 7H), 7.15 (d, J=8.4 Hz, 2H), 6.97 (t, J=7.2, 1H), 6.84-6.81 (m, 4 H), 4.21 (q, J=7.2 Hz, 2H), 4.16 (t, J=6.8 Hz, 2H), 3.27 (A of Abq, J=14.0 Hz, 1H), 3.11 (B of Abq, J=14.0 Hz, 1H), 3.07-2.95 (m, 4H), 2.88 (t, J=6.8 Hz, 2H), 2.26 (s, 3H), 1.40 (s, 3H), 1.22 (t, J=7.2 Hz, 3H).

Step B

2-Methyl-3-{4-[2-(5-methyl-2-phenethyl-oxazol-4-yl)-ethoxy]-phenyl}-2-phenoxy-propionic acid

The title compound was mage according to the procedure of Example 88, Step H. $^1$H NMR (400 MHz, CDCl$_3$) δ 9.15 (br s, 1H), 7.27-7.08 (m, 9H), 6.89 (t, J=7.3 Hz, 1H), 6.82 (d, J=7.7 Hz, 2H), 6.74 (d, J=7.7 Hz, 2H), 4.07 (t, J=6.2 Hz, 2H), 3.19 (A of ABq, J=13.9 Hz, 1H), 3.03 (B of ABq, J=13.9 Hz, 1H), 3.04-2.96 (m, 4H), 2.84 (t, J=6.2 Hz, 2H), 2.23 (s, 3H), 1.27 (s, 3H).

Example 88

(S)-2-(4-{2-[5-Methyl-2-(5-methyl-thiophen-2-yl)-oxazol-4-yl]-ethoxy}-benzyl)-2-phenoxy-butyric acid

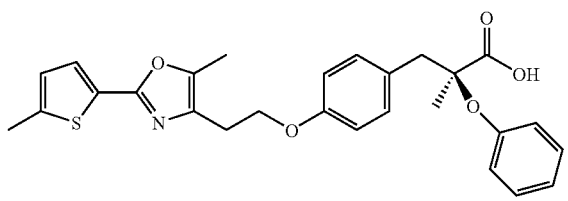

Step A

2-[(5-Methyl-thiophene-2-carbonyl)-amino]-succinic acid 4-methyl ester

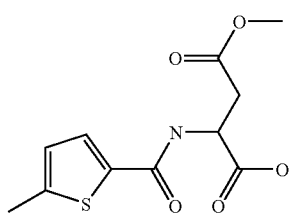

A mixture of 5-methyl-2-thiophenecarboxylic acid (6.44 g, 45.4 mmol), N-methyl-morpholine (4.82 g, 47.7 mmol), and 2-chloro-4,6-dimethyl-1,3,5-triazine (8.2 g, 46.7 mmol) in THF (100 mL) was stirred at ambient temperature for 90 min. β-Methyl L-aspartate (8.6 g, 46.7 mmol), N-methyl-morpholine (9.64 g, 95.3 mmol), and distilled water (10 mL) were added and the mixture was stirred 3 h. The reaction was partitioned between CH$_2$Cl$_2$ and 1N HCl. The organic phase was dried (MgSO$_4$), filtered and concentrated under reduced pressure. The clear, colorless oil was used without further purification. $^1$H NMR (400 MHz, CDCl$_3$) δ 7.39 (d, J=3.6 Hz, 1H), 7.09 (br d, J=7.6 Hz, 1H), 6.74 (dd, J=3.6, 0.8 Hz, 1H), 5.00 (m, 1H), 4.07 (s, 3H), 3.06 (A of ABX, $J_{AB}$=17.6 Hz, $J_{AX}$=4.4 Hz, 1H), 3.05 (B of ABX, $J_{BA}$=17.6 Hz, $J_{BX}$=4.8 Hz, 1H), 2.51 (s, 3H).

Step B

3-[(5-Methyl-thiophene-2-carbonyl)-amino]-4-oxo-pentanoic acid methyl ester

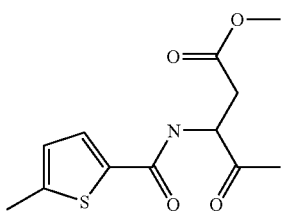

2-[(5-Methyl-thiophene-2-carbonyl)-amino]-succinic acid 4-methyl ester (12 g, 45 mmol), pyridine (60 mL) and acetic anhydride (50 mL) were combined in a 500 mL flask. The reaction mixture was heated at 90° C. for 2 h and then cooled to ambient temperature. After concentrating the reaction mixture under reduced pressure, DI water was added (100 mL). (Potential exotherm!). The reaction mixture was partitioned between water and $CH_2Cl_2$. The organic phase was washed with 1N HCl and then dried ($MgSO_4$), filtered and concentrated under reduced pressure. The material was used without further purification. MS (EI) 270.1 (M+H).

Step C

[5-Methyl-2-(5-methyl-thiophen-2-yl)-oxazol-4-yl]-acetic acid methyl ester

In a 100 mL flask, 3-[(5-methyl-thiophene-2-carbonyl)-amino]-4-oxo-pentanoic acid methyl ester (12 g, 45 mmol), and acetic anhydride (30 mL) were combined. Following addition of concentrated $H_2SO_4$ (1 mL), the solution was heated to 90° C. for 30 min and then cooled to ambient temperature. The reaction was slowly diluted with DI water (30 mL, potential exotherm). The reaction mixture was partitioned between $CH_2Cl_2$ and water. The organic phase was washed with DI water and brine (150 mL), and then dried over $MgSO_4$ and concentrated to obtain a brown oil. The residue was purified by column chromatography (700 mL $SiO_2$, 30% EtOAc/hexanes) to provide the desired product (3.44 g) as a pale yellow oil. Rf=0.39 (50% EtOAc/hexanes); $^1$H NMR (400 MHz, $CDCl_3$) δ 7.40 (d, J=3.6 Hz, 1H), 6.73 (dd, J=3.6, 0.8 Hz, 1H), 3.71 (s, 3H), 3.55 (s, 2H), 2.51 (s, 3H), 2.32 (s, 3H).

Step D

[5-Methyl-2-(5-methyl-thiophen-2-yl)-oxazol-4-yl]-acetic acid

[5-Methyl-2-(5-methyl-thiophen-2-yl)-oxazol-4-yl]-acetic acid methyl ester (3.44 g, 13.7 mmol), in MeOH (45 mL) was treated with 5N NaOH (16 mL) and then the solution was warmed to 40° C. After 30 min, the reaction mixture was concentrated under reduced pressure, suspended in water, and then acidified to pH=1 with 5N HCl. The mixture was extracted with EtOAc (2×), dried ($MgSO_4$), and concentrated to provide 2.47 g (76%) of the product as an off-white solid. $^1$H NMR (400 MHz, $CDCl_3$) δ 7.43 (d, J=3.6 Hz, 1H), 6.73 (dd, J=3.6, 0.8 Hz, 1H), 3.59 (s, 2H), 2.51 (s, 3H), 2.32 (s, 3H).

Step E

2-[5-Methyl-2-(5-methyl-thiophen-2-yl)-oxazol-4-yl]-ethanol $BH_3$-THF complex (15 mL of a 1.0 M solution in THF) was added dropwise via addition funnel over 50 min to a solution of [5-methyl-2-(5-methyl-thiophen-2-yl)-oxazol-4-yl]-acetic acid (1.5 g, 6.33 mmol) in THF (10 mL). The reaction mixture was stirred at ambient temperature for 3 h, and then quenched with MeOH (4 mL). After heating at 50° C. for 2 h, the reaction mixture was cooled to ambient temperature, and then partitioned between $CH_2Cl_2$ and 1N NaOH. The organic phase was washed with brine (1×50 mL), dried over $MgSO_4$ and concentrated to obtain a colorless oil (1.4 g, 99%) which was used without further purification. $^1$H NMR (400 MHz, $CDCl_3$) δ 7.38 (d, J=3.6 Hz, 1H), 6.73 (dd, J=3.6, 0.8 Hz, 1H), 3.89 (q, J=5.6 Hz, 2H), 3.04 (t, J=5.9 Hz, 1H), 2.68 (t, J=5.6 Hz, 2H), 2.51 (s, 3H), 2.30 (s, 3H); MS (EI+) 224.04 (M+H); 246.06 (M+H+Na).

Step F

Toluene-4-sulfonic acid 2-[5-methyl-2-(5-methyl-thiophen-2-yl)-oxazol-4-yl]-ethyl ester A solution of 2-[5-methyl-2-(5-methyl-thiophen-2-yl)-oxazol-4-yl]-ethanol (1.42 g, 6.37 mmol) in $CH_2Cl_2$ (25 mL) at 0° C. was treated with pyridine (2.0 g, 25.5 mmol, 2.0 mL), DMAP (233 mg, 1.91 mmol), and tosyl anhydride (2.70 g, 8.28 mmol). The reaction was warmed to ambient temperature and, after 90 min, the solution was filtered through a pad of silica gel (rinsed with $CH_2Cl_2$). The product was used without further purification. MS (EI+) 378.1 (M+H).

Step G (S)-2-(4-{2-[5-Methyl-2-(5-methyl-thiophen-2-yl)-oxazol-4-yl]-ethoxy}-benzyl)-2-phenoxy-butyric acid ethyl ester

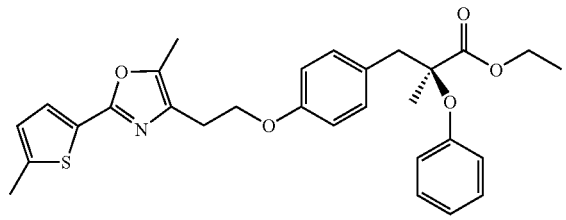

(S)-3-(4-Hydroxyphenyl)-2-methyl-2-phenoxypropionic acid ethyl ester (255 mg, 0.85 mmol), toluene-4-sulfonic acid 2-[5-methyl-2-(5-methyl-thiophen-2-yl)-oxazol-4-yl]-ethyl ester (383 mg, 1.02 mmol) and $Cs_2CO_3$ (335 mg, 1.02 mmol) are combined in anhydrous DMF (6 mL) and stirred for 16 h at 55° C. under an atmosphere of nitrogen. The mixture was then cooled and diluted with ethyl acetate (50 mL), and washed with water then brine. The organic layer was dried with $MgSO_4$ and concentrated in vacuo to a viscous tan oil. The residue was purified by flash column chromatography (200 g silica, hexanes to 25% EtOAc/hexanes) to provide the title compound as a colorless oil (201 mg, 47%). ¹H NMR (400 MHz, CDCl₃) δ 7.39 (d, J=3.4 Hz, 1H), 7.22-7.13 (m, 4H), 6.97 (t, J=7.2 Hz, 1H), 6.85-6.80 (m, 4H), 6.72 (dd, J=3.6, 1.2 Hz, 1H), 4.23-4.17 (m, 4H), 3.26 (A of Abq, J=13.6 Hz, 1H), 3.11 (B of Abq, J=13.6 Hz, 1H), 2.94 (t, J=5.6 Hz, 2H), 2.50 (s, 3H), 2.34 (s, 3H), 1.39 (s, 3H), 1.22 (t, J=7.2 Hz, 3H); MS (EI+) 505.9 (M+H); 637.8 (M+H+Cs).

Step H (S)-2-(4-{2-[5-Methyl-2-(5-methyl-thiophen-2-yl)-oxazol-4-yl]-ethoxy}-benzyl)-2-phenoxy-butyric acid

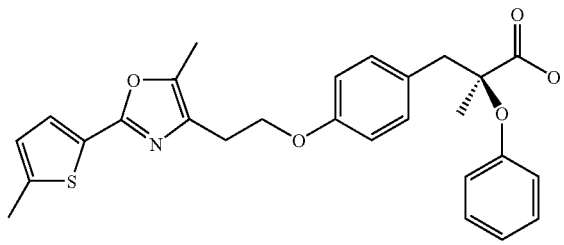

(S)-2-(4-{2-[5-Methyl-2-(5-methyl-thiophen-2-yl)-oxazol-4-yl]-ethoxy}-benzyl)-2-phenoxy-butyric acid ethyl ester (201 mg, 0.40 mmol) in MeOH (8 mL) was treated with 2N NaOH (8 mL) and warmed to 55° C. After 18 h, the mixture was concentrated under reduced pressure and then acidified with 5N HCl to pH=1. The solution was extracted with EtOAc and then the organic phases dried (MgSO₄), filtered and concentrated to a white foam (158 mg, 81%) that was dried in a vacuum oven at 50° C. for 24 h: ¹H NMR (400 MHz, CDCl₃) δ 7.36 (d, J=3.6 Hz, 1H), 7.16 (t, J=8.0 Hz, 2H), 7.10 (d, J=8.4 Hz, 2H), 6.96 (t, J=7.2 Hz, 1H), 6.83 (d, J=7.6 Hz, 2H), 6.75 (d, J=8.8 Hz, 2H), 6.71 (dd, J=3.6, 0.8 Hz, 1H), 4.13 (t, J=6.8 Hz, 2H), 3.18 (A of Abq, J=13.6 Hz, 1H), 3.00 (B of Abq, J=13.6 Hz, 1H), 2.90 (t, J=6.8 Hz, 2H), 2.49 (s, 3H), 2.31 (s, 3H), 1.31 (s, 3H).

Example 89

2-(4-{2-[5-Methyl-2-(5-methyl-thiophen-2-yl)-oxazol-4-yl]-ethoxy}-benzyl)-2-phenoxy butyric acid

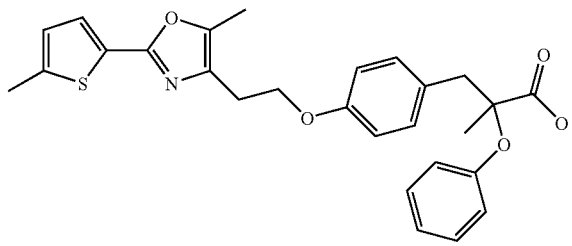

The title compound was prepared in the manner of Example 86 from racemic 3-(4-hydroxyphenyl)-2-methyl-2-phenoxypropionic acid ethyl ester and toluene-4-sulfonic acid 2-[5-methyl-2-5-methyl-thiophen-2-yl)-oxazol-4-yl)-ethyl ester. ¹H NMR (400 MHz, CDCl₃) δ 7.35 (d, J=3.2 Hz, 1H), 7.03-6.99 (m, 4H), 6.83 (t, J=7.2 Hz, 1H), 6.75-6.70 (m, 5H), 4.08 (t, J=6.4 Hz, 2H), 3.12 (A of Abq, J=13.6 Hz, 1H), 2.86 (t, J=6.4 Hz, 2H), 2.81 (B of Abq, J=13.6 Hz, 1H), 2.48 (s, 3H), 2.27 (s, 3H), 1.12 (s, 3H).

Example 90

2-Methyl-3-{5-[3-(5-methyl-2-phenyl-oxazol-4-yl)-propionyl]-thiophen-2-yl}-2-phenoxy-propionic acid

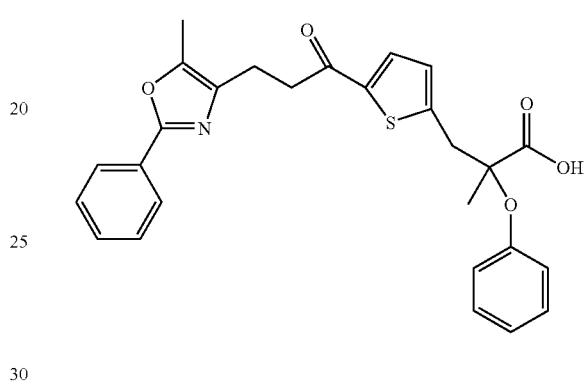

Step A

3-Hydroxy-2-methyl-2-phenoxy-3-thiophen-2-yl-propionic acid

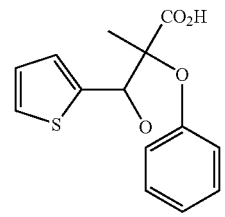

To a 2.0 M solution of LDA in THF/heptane/ethyl benzene (200 mL, 408 mmol) cooled by an ice/acetone bath, a 0.75 M solution of 2-phenoxypropionic acid (30.8 g, 185 mmol) in THF (250 mL) was added dropwise over 30 min, keeping the reaction temperature below −10° C. After allowing the reaction mixture to stir for 15 min, a 0.75 M solution of 2-thiophenecarboxaldehyde (20.8 g, 185 mmol) in THF (250 mL) was added dropwise over the course of 1 h, maintaining the reaction temperature below −5° C. After stirring for 5 min at 0° C., HPLC analysis showed the reaction to be complete. The reaction was poured into ice water (600 mL) and ether (500 mL) was added. Hexane (1.0 L) was added and the layers were separated. The aqueous layer was further extracted with Et₂O:hexane (1:2) (750 mL). The organic layers were checked for product then discarded. Ethyl acetate (500 mL) was added to the aqueous layer, acidified to pH=2 with conc. HCl (18 mL), and the layers were separated. The aqueous layer was extracted with ethyl acetate (2×200 mL). The organic layer was dried over NaCl and solvent removed in vacuo to provide 50.0 g of crude product. The product was used in the next step without further purification: $^1$H NMR (400 MHz, CDCl$_3$) δ 7.33 (dd, 1 H), 7.26 (m, 2 H), 7.12 (m, 1 H), 7.04 (d, 1 H), 6.97 (m, 2 H), 6.87 (dd, 1 H), 5.37 (s, 1 H), 1.40 (s, 3 H); MS (EI–) 277.1 (M–1)⁻.

Step B

2-Methyl-2-phenoxy-3-thiophen-2-yl-propionic acid

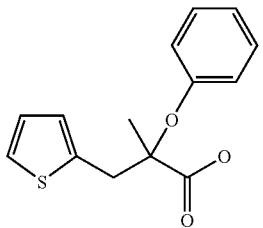

To a solution of triethylsilane (56.4 g, 77.4 mL, 485 mmol) in 100 mL of CH$_2$Cl$_2$ at –20° C., boron trifluoride diethyl etherate (68.8 g, 61.5 mL, 485 mmol) was added. A solution of 3-hydroxy-2-methyl-2-phenoxy-3-thiophen-2-yl-propionic acid (45.0 g, 162 mmol) in CH$_2$Cl$_2$ (600 mL) was then added dropwise to the BF$_3$ solution over 1 h, keeping the temperature at –15° C. The reaction was stirred at 0° C. for 2 h. The reaction was quenched with 1 N NaOH (approx. 360 mL) diluted with 180 mL of water and the pH was adjusted to pH=4.0 using 1 N HCl and 1 N NaOH. The organic layer was separated and the aqueous layer was further extracted with CH$_2$Cl$_2$ (2×300 mL). The combined organic layers were then washed with 0.1 N HCl (300 mL) and water (2×300 mL). Xylene (150 mL) and NaCl were added and the organics were concentrated to dryness to yield 40.0 g of crude product. The product was used in the next step without further purification: $^1$H NMR (400 MHz, CDCl$_3$) δ 6.86-7.29 (m, 8 H), 3.53 (d, 2 H), 3.37 (d, 2 H), 1.44 (s, 3 H); MS (EI) 263.1 (M+H)⁺.

Step C

2-Methyl-2-phenoxy-3-thiophen-2-yl-propionic acid methyl ester

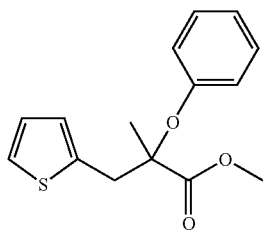

In a 100 mL beaker, 1.12 g of 1-methyl-3-nitro-1-nitrosoguanidine (MNNG) was added to a solution of ether (30 mL) and 5 N KOH (2.3 mL) and stirred until N$_2$ evolution ceased. In another beaker, crude 2-methyl-2-phenoxy-3-thiophen-2-yl-propionic acid (1.00 g) was dissolved in CH2Cl$_2$ (20 mL). The beaker containing the ether/base mixture was then placed in a Dewar flask containing dry ice/acetone, the aqueous layer was frozen and the ether layer decanted into the other beaker containing the crude acid solution. This mixture was then stirred for an additional 5 min, which by HPLC showed the reaction to be complete. The solvent was removed in vacuo to provide a crude oil. Purification by flash chromatography EtOAc:hexane (1:10) provided 533 mg of desired product (28%): $^1$H NMR (400 MHz, CDCl$_3$) • 7.16-7.22 (m, 4 H), 6.96 (m, 1 H), 6.91 (m, 1 H), 6.84 (m, 2 H), 3.73 (s, 3 H), 3.49 (d, 1 H), 3.38 (d, 1 H), 1.42 (s, 3 H); MS (EI) 277.1 (M+H)⁺.

Step D 3-(5-Methyl-2-phenyl-oxazol-4-yl)-propionitrile

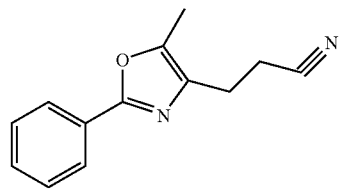

Toluene-4-sulfonic acid 2-(5-methyl-2-phenyloxazol-4-yl)ethyl ester (5.00 g, 14.0 mmol), sodium cyanide (852 mg, 16.8 mmol), and potassium bicarbonate (1.70 g, 16.8 mmol) were combined and vigorously stirred in DMSO (50 mL) at 50° C. for 2 h, then overnight at 25° C. The mixture was then poured into H$_2$O (50 mL) and extracted with Et$_2$O (2×50ML). The organic layer were combined then washed with H$_2$O (50 mL), sat. NaCl (50 mL), dried over NaCl. The solvent was removed in vacuo to provide 2.90 g (98%) of product as a white powder: $^1$H NMR (400 MHz, CDCl$_3$) δ 7.93 (m, 2 H), 7.39 (m, 3 H), 2.81 (t, 2 H), 2.71 (t, 2 H), 2.35 (s, 3 H); MS (EI) 213.1 (M+H)⁺.

Step E 3-(5-Methyl-2-phenyl-oxazol-4-yl)-propionic acid

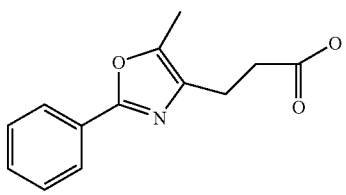

A mixture of 3-(5-methyl-2-phenyl-oxazol-4-yl)-propionitrile (3.4 g, 16.0 mmol) and HCl (10 mL) was stirred at 95° C. for 4.5 h. The reaction mixture was cooled to room temperature, poured into ice water (50 mL). The product was extracted with a 1:1 mixture of Et$_2$O and EtOAc (2×50 mL). The combined organic layers were washed with sat. NaCl (50 mL), dried over NaCl, and solvent removed in vacuo to afford 2.27 g (61%) of acid as a white solid: $^1$H NMR (400 MHz, CDCl$_3$) δ 7.93 (m, 2 H), 7.40 (m, 3 H), 2.78 (t, 2 H), 2.76 (t, 2 H), 2.32 (s, 3 H); MS (EI) 232.0 (M+H)$^+$.

Step F

2-Methyl-3-{5-[3-(5-methyl-2-phenyl-oxazol-4-yl)-propionyl]-thiophen-2-yl}-2-phenoxy-propionic acid methyl ester

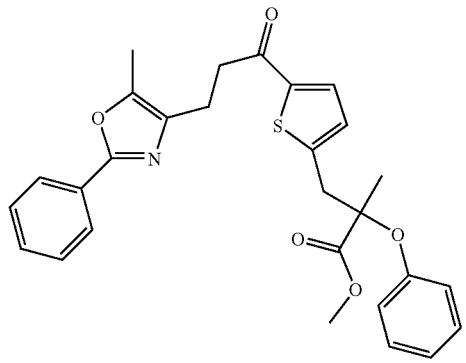

A sample of 3-(5-methyl-2-phenyl-oxazol-4-yl)-propionic acid (2.27 g, 9.82 mmol) was dissolved in anhydrous CH$_2$Cl$_2$ (20 mL) followed by addition of a catalytic amount of DMF (0.72 mL) and slow addition of a 2 M solution of oxalyl chloride (7.36 mL). The reaction mixture was stirred at room temperature for 24 h under N$_2$. The solvent was removed in vacuo to provide crude acid chloride which was then dissolved in 10 mL anhydrous CH$_2$Cl$_2$ and then added to a flask containing 2-methyl-2-phenoxy-3-thiophen-2-yl-propionic acid methyl ester (527167) (2.51 g, 9.11 mmol) in anhydrous CH$_2$Cl$_2$ (10 mL) at 0° C. under N$_2$. Anhydrous 1.0 M SnCl$_4$ solution (5.6 mL) was then added dropwise at 0° C. After 1 h, the reaction was checked by HPLC, it appeared that little product had formed. Another 3.3 mL of SnCl$_4$ solution was added and allowed to stir for 24 h at room temperature. When the starting materials were consumed, the reaction was quenched by adding 6 M HCl dropwise at 0° C. until solid forms (20 mL) and the aqueous phase was extracted with CH$_2$Cl$_2$ (2×50 mL). The organic layer was washed with water (50 mL) and solvent removed to give an oil. Following column chromatography (gradient 5% to 20% EtOAc in hexane), 1.31 g (30%) of product was obtained: $^1$H NMR (400 MHz, CDCl$_3$) δ 7.95 (d, 2 H), 7.56 (d, 1 H), 7.38 (m, 3 H), 7.20 (m, 2 H), 6.84 (t, 1 H), 6.81 (m, 3 H), 3.72 (s, 3 H), 3.50 (d, 1 H), 3.33 (d, 1 H), 3.28 (t, 2 H), 2.89 (t, 2 H), 2.33 (s, 3 H), 1.41 (s, 3 H); MS (EI) 490.2 (M+H)$^+$.

Step G

2-Methyl-3-{5-[3-(5-methyl-2-phenyl-oxazol-4-yl)-propionyl]-thiophen-2-yl}-2-phenoxy-propionic acid (515337)

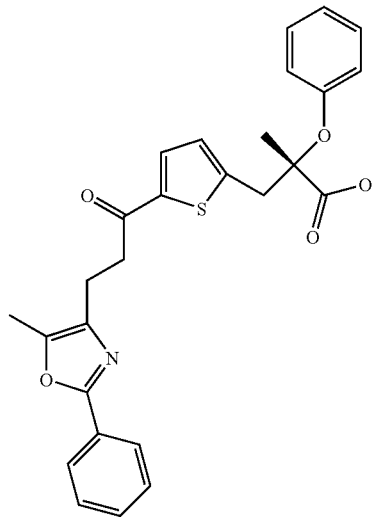

Hydrolysis, using the procedure of Example 1, Step E, provided 275 mg (94%) of product from 300 mg of 2-methyl-3-{5-[3-(5-methyl-2-phenyl-oxazol-4-yl)-propionyl]-thiophen-2-yl}-2-phenoxy-propionic acid methyl ester: $^1$H NMR (400 MHz, CDCl$_3$) δ 8.05 (d, 2 H), 7.60 (d, 1 H), 7.42 (m, 3 H), 7.20 (m, 2 H), 6.84 (t, 1 H), 6.81 (m, 3 H), 3.50 (d, 1 H), 3.35 (t, 2 H), 3.33 (d, 1 H), 2.95 (t, 2 H), 2.40 (s, 3 H), 1.41 (s, 3 H); MS (EI) 476.0 (M+H)$^+$.

Example 91

2-Methyl-3-{5-[3-(5-methyl-2-phenyl-oxazol-4-yl)-propyl]-thiophen-2-yl}-2-phenoxy-propionic acid

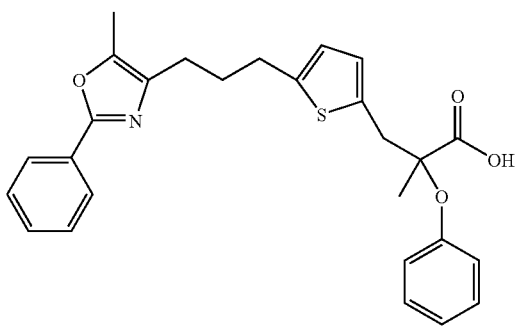

Step A

3-{5-[1-Hydroxy-3-(5-methyl-2-phenyl-oxazol-4-yl)-propyl]-thiophen-2-yl}-2-methyl-2-phenoxy-propionic acid methyl ester

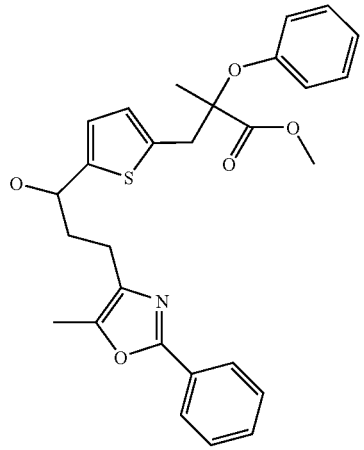

A sample of 2-methyl-3-{5-[3-(5-methyl-2-phenyl-oxazol-4-yl)-propionyl]-thiophen-2-yl}-2-phenoxy-propionic acid methyl ester (1.00 g, 2.04 mmol) was dissolved in THF (40 mL) and MeOH (20 mL) and cooled to 0° C. Sodium borohydride (115 mg, 3.06 mmol) was added and allowed to stir at 0° C. for 45 min. The reaction was monitored by HPLC. Upon the completion of the reaction, the bulk of the solvent was removed in vacuo and water (40 mL) was added. The mixture was acidified with 6 N HCl (20 mL) and stirred for 30 min. This aqueous mixture was then extracted with $CH_2Cl_2$ (2×50 mL). The organic fractions were combined, dried over NaCl, and solvent removed in vacuo to give a crude oil. Flash chromatography (gradient 20% to 40% EtOAc in hexane) provided 650 mg (65%) of desired product: $^1$H NMR (400 MHz, $CDCl_3$) δ 8.02 (d, 2 H), 7.47 (m, 3 H), 7.19 (m, 2 H), 6.96 (t, 1 H), 6.79 (m, 3 H), 6.68 (d, 2 H), 4.96 (m, 1 H), 3.72 (s, 3 H), 3.43 (d, 1 H), 3.29 (d, 1 H), 2.71 (m, 2 H), 2.30 (s, 3 H), 2.17 (m, 2 H), 1.42 (s, 3 H); MS (EI) 492.2 (M+H)$^+$.

Step B

2-Methyl-3-{5-[3-(5-methyl-2-phenyl-oxazol-4-yl)-propyl]-thiophen-2-yl}-2-phenoxy-propionic acid methyl ester

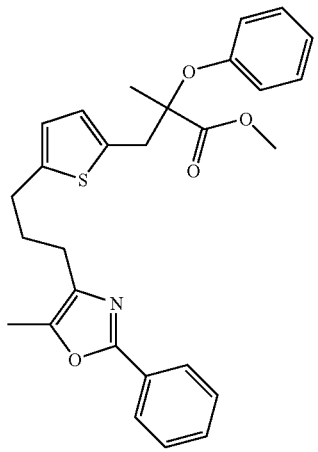

To a solution of triethylsilane (0.62 mL, 3.89 mmol) in $CH_2Cl_2$ (4 mL) at −20° C., boron trifluoride diethyl etherate (0.49 mL, 3.89 mmol) was added. A solution of 3-{5-[1-hydroxy-3-(5-methyl-2-phenyl-oxazol-4-yl)-propyl]-thiophen-2-yl}-2-methyl-2-phenoxy-propionic acid methyl ester (650 mg, 1.30 mmol) in $CH_2Cl_2$ (4 mL) was then added dropwise to the $BF_3$ solution over 1 h, keeping the temperature at −15° C. The reaction was stirred at 0° C. for 2 h. The reaction was quenched with 1 N NaOH (approx. 3.6 mL) diluted with 1.8 mL of water and the pH was adjusted to pH 4.0 using 1 N HCl and 1 N NaOH. The organic layer was separated and the aqueous layer was further extracted with $CH_2Cl_2$ (2×30 mL). The combined organic layers were then washed with 0.1 N HCl (30 mL) and water (2×30 mL). Xylene (15 mL) and NaCl were added and the organics were concentrated to dryness to yield a yellow oil. The product was used in the next step without further purification: $^1$H NMR (400 MHz, $CDCl_3$) δ 7.95 (d, 2 H), 7.37 (m, 4H), 7.20 (m, 1 H), 6.96 (t, 1 H), 6.84 (d, 2 H), 6.60 (dd, 2 H), 3.72 (s, 3 H), 3.41 (d, 1 H), 3.30 (d, 1 H), 2.78 (t, 2 H), 2.50 (t, 2 H), 2.24 (s, 3 H), 2.00 (m, 2 H), 1.43 (s, 3 H); MS (EI) 476.2 (M+H)$^+$.

Step C

2-Methyl-3-{5-[3-(5-methyl-2-phenyl-oxazol-4-yl)-propyl]-thiophen-2-yl}-2-phenoxy-propionic acid

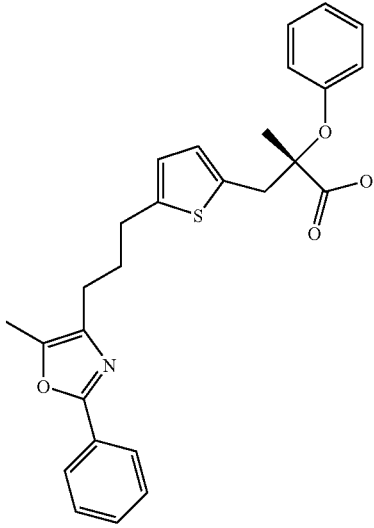

2-Methyl-3-{5-[3-(5-methyl-2-phenyl-oxazol-4-yl)-propyl]-thiophen-2-yl}-2-phenoxy-propionic acid methyl ester 400 mg) was dissolved in EtOH (10 mL), and then 5 N NaOH (3 mL) was added. This mixture was allowed to stir at 60° C. for 1 h. The mixture was cooled to room temperature and then acidified to pH=2 by the dropwise addition of 5 N HCl. This acidic mixture was diluted with $H_2O$ (10 mL) and then extracted with $CH_2Cl_2$ (2×25 mL). The organic layers were combined, dried over NaCl, and solvent removed in vacuo which provided 354 mg (92%) of desired acid: $^1$H NMR (400 MHz, $CDCl_3$) δ 8.05 (d, 2 H), 7.39 (m, 4 H), 7.23 (m, 1 H), 7.03 (t, 1 H), 6.95 (d, 2 H), 6.70 (d, 1 H), 6.62 (d, 1 H), 3.40 (d, 1 H), 3.30 (d, 1 H), 2.80 (t, 2 H), 2.52 (t, 2 H), 2.27 (s, 3 H), 2.02 (m, 2 H), 1.44 (s, 3 H); MS (EI) 462.2 (M+H)$^+$.

Example 92

2-(2-Methoxy-phenoxy)-2-methyl-3-{4-[2-(5-methyl-2-phenyl-oxazol-4-yl)-ethoxy]-phenyl}-propionic acid

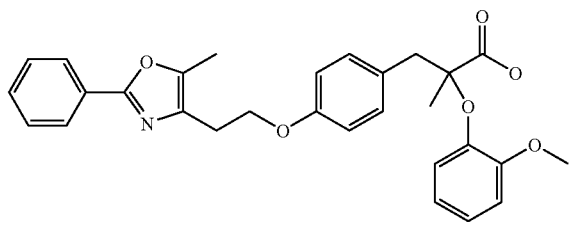

The title compound was prepared using the representative Standard Procedure (E) from 3-(4-Hydroxy-phenyl)-2-(2-methoxy-phenoxy)-2-methyl-propionic acid ethyl ester and toluene-4-sulfonic acid 2-(5-methyl-2-phenyl-oxazol-4-yl)-ethyl ester. $^1$H NMR (400 MHz, CDCl$_3$): • 7.99-7.97 (m, 2H), 7.47 (dd, 3H, J=5.08 Hz, 1.96 Hz), 7.18 (d, 2H, J=8.60), 7.07 (td, 1H, J=6.65 Hz, 1.56 Hz), 6.89-6.80 (m, 4H), 6.63 (dd, 1H, J=7.82 Hz, 1.56 Hz), 4.21 (t, 2H, J=6.26 Hz), 3.82 (s, 3H), 3.30 (d, 1H, J=14.1 Hz), 3.10-3.04 (m, 3H), 2.41 (s, 3H), 1.30 (s, 3H). MS [ES+] m/z exact mass calcd for C$_{29}$H$_{30}$NO$_6$ 488.2073, found 488.2086.

Example 93

2-(2-Methoxy-phenoxy)-2-methyl-3-{4-[2-(5-methyl-2-thiophen-2-yl-oxazol-4-yl)-ethoxy]-phenyl}-propionic acid

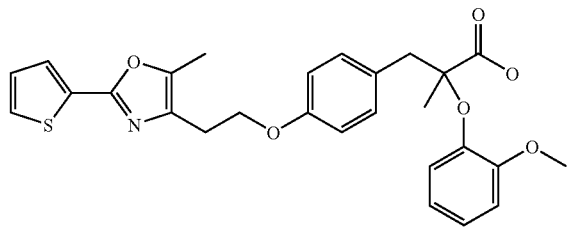

The title compound was prepared using the representative Standard Procedure (E) from 3-(4-Hydroxy-phenyl)-2-(2-methoxy-phenoxy)-2-methyl-propionic acid ethyl ester and toluene-4-sulfonic acid 2-(5-methyl-2-thiophen-2-yl-oxazol-4-yl)-ethyl ester. $^1$H NMR (400 MHz, CDCl$_3$): • 7.72 (d, 1H, J=3.52 Hz), 7.45 (d, 1H, J=3.52 Hz), 7.18 (d, 2H, J=8.60 Hz), 7.12-7.05 (m, 2H), 6.88 (d, 1H, J=7.82 Hz), 6.84-6.79 (m, 3H), 6.62 (d, 1H, J=6.65 Hz), 4.19 (t, 2H, J=6.26 Hz), 3.82 (s, 3H), 3.30 (d, 1H, J=14.08 Hz), 3.08 (d, 1H, J=14.08 Hz), 3.00 (t, 2H, J=6.26 Hz), 2.37 (s, 3H), 1.30 (s, 3H). MS [ES+] m/z exact mass calcd for C$_{27}$H$_{28}$NO$_6$S 494.1637, found 494.1640.

Example 94

3-{4-[2-(2-Cyclohexyl-5-methyl-oxazol-4-yl)-ethoxy]-phenyl}-2-(2-methoxy-phenoxy)-2-methyl-propionic acid

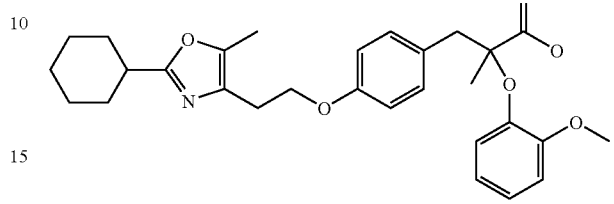

The title compound was prepared using the representative Standard Procedure (E) from 3-(4-Hydroxy-phenyl)-2-(2-methoxy-phenoxy)-2-methyl-propionic acid ethyl ester and toluene-4-sulfonic acid 2-(2-cyclohexyl-5-methyl-oxazol-4-yl)-ethyl ester. $^1$H NMR (400 MHz, CDCl$_3$): δ 7.18 (d, 2H, J=8.21 Hz), 7.06 (t, 1H, J=7.82 Hz), 6.88 (d, 1H, J=8.21 Hz), 6.83-6.79 (m, 3H), 6.62 (d, 1H, J=7.82 Hz), 4.12 (t, 2H, J=6.65 Hz), 3.82 (s, 3H), 3.29 (d, 1H, J=14.08 Hz), 3.09 (d, 1H, J=14.08 Hz). 2.85 (t, 2H, J=6.65 Hz), 2.70-2.63 (m, 1H), 2.21 (s, 3H), 1.99 (d, 2H, J=12.51 Hz), 1.77 (d, 2H, J=12.90 Hz), 1.67 (d, 1H, J=11.73 Hz, 1.50 (q, 2H, J=12.51 Hz), 1.37-1.21 (m, 5H). MS [ES+] m/z exact mass calcd for C$_{29}$H$_{36}$NO$_6$ 494.2543, found 494.2562.

Example 95

2-Methyl-3-{4-[2-(5-methyl-2-phenyl-oxazol-4-yl)-ethoxy]-phenyl}-2-o-tolyloxy-propionic acid

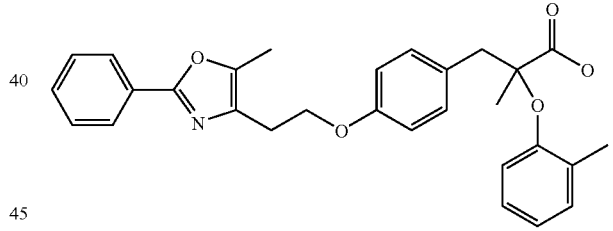

Step A 2-o-Tolyloxy-propionic acid ethyl ester

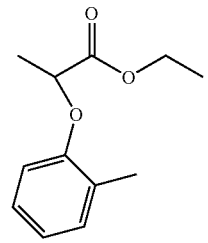

Cesium carbonate (53.86 g, 165.3 mmol) was added to a solution of 2-cresol (10.0 g, 92.5 mmol) in anhydrous DMF (500 mL) at room temperature under an atmosphere of nitrogen. After five minutes, ethyl 2-bromopropionate (16.7 mL, 92.5 mmol, d=1.394) was added rapidly dropwise and the resultant mixture was allowed to stir at 90° C. for 18 h.

The reaction mixture was diluted with diethyl ether, then extracted twice with 1N HCl and twice with water. The organic layer was dried over MgSO₄ and concentrated in vacuo to provide the title compound (19.7 g, 100%). ¹H NMR (400 MHz, CDCl₃): δ7.16 (d, 1H, J=7.43 Hz), 7.11 (t, 1H, J=7.43 Hz), 6.89 (t, 1H, J=7.48 Hz), 6.70 (d, 1H, J=7.43 Hz), 4.75 (q, 1H, J=6.65 Hz), 4.23 (q, 2H, J=6.65 Hz), 2.30 (s, 3H), 1.64 (dd, 3H, J=7.04 Hz, 0.78 Hz,), 1.26 (td, 3H, J=7.04 Hz, 0.78 Hz). R$_f$=0.37 in 25% ether in hexanes.

Step B 3-(4-Benzyloxy-phenyl)-3-hydroxy-2-methyl-2-o-tolyloxy-propionic acid ethyl ester

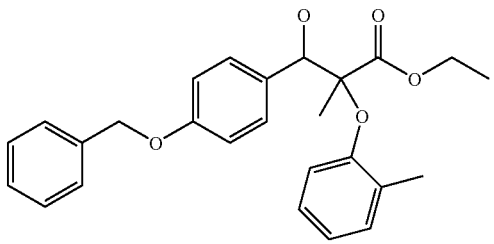

A solution of LDA (34.9 mL, 52.4 mmol, 1.5M in cyclohexane) in anhydrous THF (60 mL) was cooled to −78° C. in a dry ice/acetone bath and added to a solution of 2-o-Tolyloxy-propionic acid ethyl ester in anhydrous THF (60 mL) also cooled to −78° C. under an atmosphere of nitrogen. After five minutes, 4-benzyloxybenzaldehyde (5.56 g, 26.2 mmol) was added in one portion. After stirring for one minute, the reaction mixture was quenched with acetic acid (5 mL, 87.4 mmol, d=1.049) and a saturated solution of aqueous NH₄Cl (50 mL). The biphasic mixture was allowed to warm to room temperature and diluted with diethyl ether (1 L). The organic layer was washed with water, dried over MgSO₄, and concentrated in vacuo. The residue was purified by flash column chromatography (13% ethyl acetate in hexanes) to provide a mixture of diastereomers of the titled compound (6.36 g, 54%). ¹H NMR (400 MHz, CDCl₃): • 7.44-7.32 (m, 6H), 7.16-6.82 (m, 5H), 69.74-6.66 (m, 2H), 5.16 (d, 1H, J=3.52 Hz), 5.07 (s, 2H), 4.26-4.15 (m, 2H), 2.28 (s, 3H), 1.43 (s, 3H), 1.22-1.17 (m, 3H). R$_f$=0.25 in 25% ethyl acetate in hexanes.

Step C 3-(4-Benzyloxy-phenyl)-3-hydroxy-2-methyl-2-o-tolyloxy-propionic acid ethyl ester

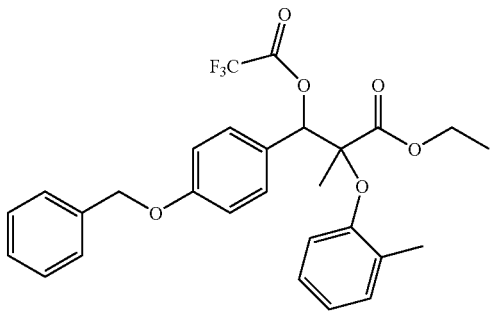

3-(4-Benzyloxy-phenyl)-3-hydroxy-2-methyl-2-o-tolyloxy-propionic acid ethyl ester (6.36 g, 15.7 mmol) in anhydrous CH₂Cl₂ (140 mL) was cooled to 0° C. and treated with pyridine (13 mL, 157.2 mmol, d=0.987). Trifluoroacetic anhydride (6.7 mL, 47.2 mmol, d=1.487) was added dropwise and the mixture was stirred for 2 h, gradually warming to ambient temperature. The reaction mixture was diluted with diethyl ether and washed with 1N HCl, then water. The organic layer was dried over Na₂SO₄ and concentrated in vacuo to produce the titled compound (7.4 g, 91%) which was used without purification. ¹H NMR (400 MHz, CDCl₃): δ 7.43-7.31 (m, 7H), 7.11 (d, 1H, J=7.43 Hz), 7.03-6.98 (m, 3H), 6.91 (t, 1H, J=7.43), 6.69 (d, 1H, J=8.21 Hz), 6.34 (s, 1H), 5.08 (s, 2H), 4.28-4.16 (m, 2H), 2.12 (s, 3H), 1.50 (s, 3H), 1.21 (td, 3H, J=7.04 Hz, 0.78 Hz). R$_f$=0.55 in 25% ethyl acetate in hexanes.

Step D 3-(4-Hydroxy-phenyl)-2-methyl-2-o-tolyloxy-propionic acid ethyl ester

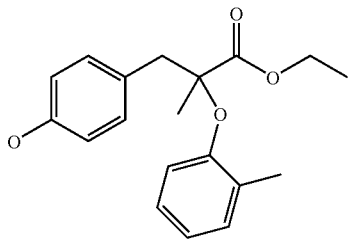

3-(4-Benzyloxy-phenyl)-2-methyl-2-o-tolyloxy-3-(2,2,2-trifluoro-acetoxy)-propionic acid ethyl ester (7.4 g, 14.3 mmol) was dissolved in ethyl acetate (300 mL), treated with 5% palladium on carbon (7.4 g), and stirred under an atmosphere of hydrogen for 96 h. The suspension was filtered through celite and concentrated in vacuo to provide the titled compound (4.8 g, 100%) as an opaque yellow oil.

¹H NMR (400 MHz, CDCl₃): • 7.14 (d, 1H, J=7.82 Hz), 7.07 t, 1H, J=8.60 Hz), 7.01 (t, 1H, J=7.82 Hz), 6.84 (t, 1H, J=7.82 Hz), 6.72 (d, 2H, J=8.60 Hz), 6.60 (d, 1H, J=7.82 Hz), 5.96 (s, 1H), 4.19-4.15 (m, 2H), 3.26 (d, 1H, J=13.69 Hz), 3.12 (d, 1H, J=13.69), 2.17 (s, 3H), 1.44 (s, 3H), 1.18 (t, 3H, J=7.04 Hz). MS [ES+] m/z exact mass calcd for C₁₉H₂₆NO₄ 332.1862, found 332.1860.

Step E

3-{4-[2-(2-Biphenyl-4-yl-5-methyl-oxazol-4-yl)-ethoxy]-phenyl}-2-(2-methoxy-phenoxy)-2-methyl-propionic acid

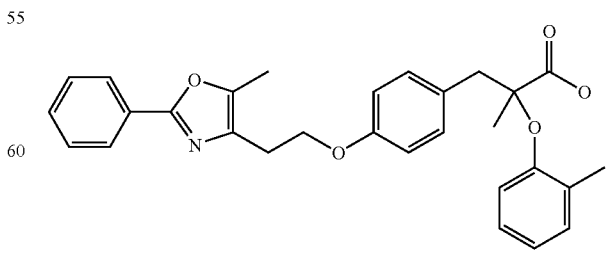

Potassium carbonate (0.078 g, 0.56 mmol) was added to a solution of 3-(4-Hydroxy-phenyl)-2-methyl-2-o-tolyloxypropionic acid ethyl ester and toluene-4-sulfonic acid 2-(2-biphenyl-4-yl-5-methyl-oxazol-4-yl)-ethyl ester in 4A sieve-dried ethanol (2 mL). The resultant mixture was stirred at 80° C. under an atmosphere of nitrogen for 18 h, then diluted with ethanol (2 mL). 5N NaOH (0.5 mL) was added, then the reaction mixture was refluxed for 2 h. The reaction mixture was concentrated in vacuo, diluted with 1N HCl, and extracted with $CH_2Cl_2$. The organic layer was dried through a Varian ChemElut cartridge, concentrated in vacuo, and purified by LCMS. $^1$H NMR (400 MHz, CDCl$_3$): • 7.96-7.92 (m, 2H), 7.40 (t, 3H, J=3.13 Hz), 7.12 (d, 2H, J=6.65 Hz), 7.06 (t, 1H, J=7.82 Hz), 6.91 (t, 1H, J=7.82 Hz), 6.80 (t, 4H, J=6.65 Hz), 4.17 (t, 2H, J=6.65 Hz), 3.25 (d, 1H, J=14.08 Hz), 3.19 (d, 1H, J=14.08 Hz), 2.98 (t, 2H, J=6.65 Hz), 2.17 (s, 3H), 1.48 (s, 3H), 1.24 (s, 3H). MS [ES+] m/z exact mass calcd for $C_{29}H_{30}NO_5$ 472.2124, found 472.2129.

Example 96

2-Methyl-3-{4-[2-(5-methyl-2-thiophen-2-yl-oxazol-4-yl)-ethoxy]-phenyl}-2-o-tolyloxy-propionic acid

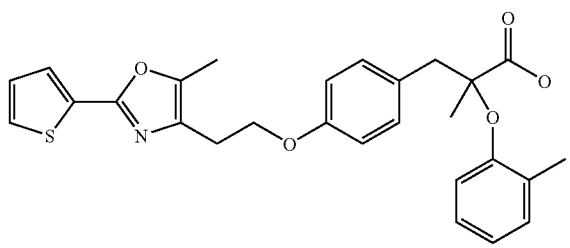

The title compound was prepared using the representative Standard Procedure (E) from 3-(4-Hydroxy-phenyl)-2-methyl-2-o-tolyloxy-propionic acid ethyl ester and toluene-4-sulfonic acid 2-(5-methyl-2-thiophen-2-yl-oxazol-4-yl)-ethyl ester. $^1$H NMR (400 MHz, CDCl$_3$): • 7.59 (dd, 1H, J=3.91 Hz, 1.17 Hz), 7.36 (dd, 1H, J=3.91 Hz, 1.17 Hz), 7.14-7.11 (m, 3H), 7.08-7.04 (m, 2H), 6.91 (t, 1H, J=7.43 Hz), 6.82-6.77 (m, 3H), 4.15 (t, 2H, J=6.65 Hz), 3.25 (d, 1H, J=14.08 Hz), 3.19 (d, 1H, J=14.08 Hz), 2.94 (t, 2H, J=6.65 Hz), 2.33 (s, 3H), 2.17 (s, 3H), 1.48 (s, 3H). MS [ES+] m/z exact mass calcd for $C_{27}H_{28}NO_5S$ 478.1688, found 478.1676.

Example 97

3-{4-[2-(2-Cyclohexyl-5-methyl-oxazol-4-yl)-ethoxy]-phenyl}-2-methyl-2-o-tolyloxy-propionic acid

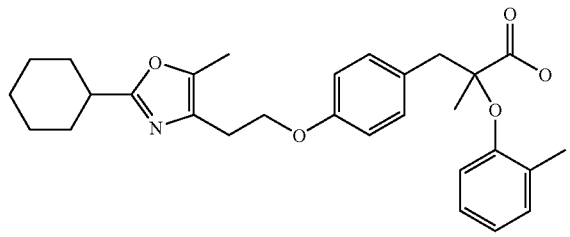

The title compound was prepared using the representative Standard Procedure (E) from 3-(4-Hydroxy-phenyl)-2-methyl-2-o-tolyloxy-propionic acid ethyl ester and toluene-4-sulfonic acid 2-(2-cyclohexyl-5-methyl-oxazol-4-yl)-ethyl ester. $^1$H NMR (400 MHz, CDCl$_3$): δ 7.14-7.11 (m, 3H), 7.06 (t, 1H, J=7.82 Hz), 6.91 (t, 1H, J=7.82 Hz), 6.79 (d, 1H, J=8.60 Hz), 6.75 (d, 2H, J=8.60 Hz), 4.11 (t, 2H, J=6.26 Hz), 3.24 (d, 1H, J=14.08 Hz), 3.18 (d, 1H, J=14.08 Hz), 2.95 (t, 2H, J=6.26 Hz), 2.90-2.87 (m, 1H), 2.29 (s, 3H), 2.17 (s, 3H), 2.02-1.99 (m, 2H), 1.81-1.78 (m, 2H), 1.71-1.68 (m, 1H), 1.58-1.52 (m, 2H), 1.47 (s, 3H), 1.38-1.21 (m, 5H). MS [ES+] m/z exact mass calcd for $C_{29}H_{36}NO_5$ 478.2593, found 478.2611.

Example 98

2-Methyl-3-(4-{2-[5-methyl-2-(1-methyl-cyclohexyl)-oxazol-4-yl]-ethoxy}-phenyl)-2-o-tolyloxy-propionic acid

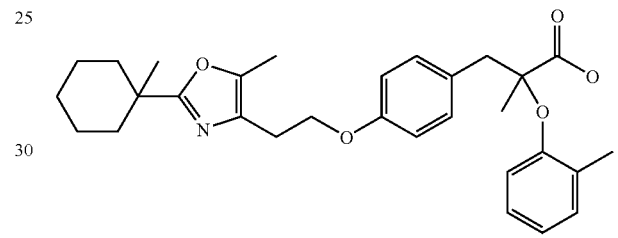

The title compound was prepared using the representative Standard Procedure (E) from 3-(4-Hydroxy-phenyl)-2-methyl-2-o-tolyloxy-propionic acid ethyl ester and Toluene-4-sulfonic acid 2-[5-methyl-2-(1-methyl-cyclohexyl)-oxazol-4-yl]-ethyl ester. $^1$H NMR (400 MHz, CDCl$_3$): δ 7.14-7.11 (m, 3H), 7.08-7.04 (m, 1H), 6.91 (t, 1H, J=7.82 Hz), 6.81 (d, 1H, J=8.60 Hz), 6.76 (d, 2H, J=8.60 Hz), 4.10 (t, 2H, J=6.26 Hz), 3.24 (d, 1H, J=14.08 Hz), 3.18 (d, 1H, J=14.08 Hz), 2.93 (t, 2H, J=6.26 Hz), 2.27 (s, 3H), 2.17 (s, 3H), 2.13-2.06 (m, 2H), 1.54-1.48 (m, 8H), 1.40-1.34 (m, 3H), 1.27 (s, 3H). MS [EI+] 492 (M+H)$^+$, [EI−] 490 (M−H)$^+$.

Example 99

2-(3-Bromo-phenoxy)-3-{4-[2-(2-cyclohexyl-5-methyl-oxazol-4-yl)-ethoxy]-phenyl}-2-methyl-propionic acid

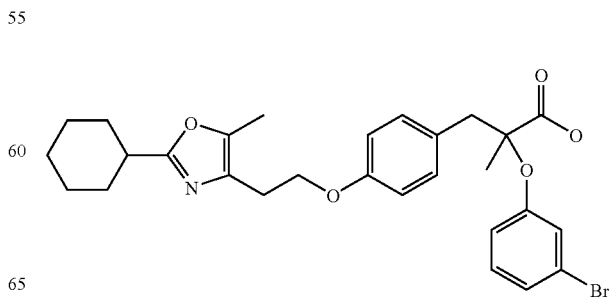

Step A

2-(3-Bromo-phenoxy)-propionic acid ethyl ester

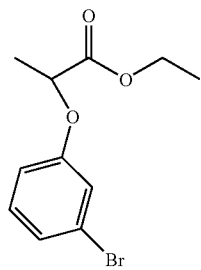

Cesium carbonate (57.8 g, 177.4 mmol) was added to a solution of 3-bromophenol (10.23 g, 59.1 mmol) in anhydrous DMF (500 mL) at room temperature under an atmosphere of nitrogen. After five minutes, ethyl 2-bromopropionate (7.7 mL, 59.1 mmol, d=1.394) was added rapidly dropwise and the resultant mixture was allowed to stir at 90° C. for 18 h. The reaction mixture was diluted with diethyl ether and extracted twice with 1N HCl and three times with water. The organic layer was dried over $Na_2SO_4$ and concentrated in vacuo. The residue was purified by flash chromatography (25% ether in hexanes) to provide the titled compound (14.8 g, 97%) as a light yellow oil. $^1$H NMR (400 MHz, CDCl$_3$): δ 7.13-7.07 (m, 3H), 7.02-7.13 (m, 1H), 6.79 (dt, 1H, J=7.63 Hz, 2.35 Hz), 4.70 (q, 1H, J=6.75 Hz), 4.23 (q, 2H, J=3.52 Hz), 1.60 (d, 3H, J=7.04 Hz), 1.24 (t, 3H, J=7.04 Hz). R$_f$=0.36 in 25% ether in hexanes.

Step B

3-(4-Benzyloxy-phenyl)-2-(3-bromo-phenoxy)-3-hydroxy-2-methyl-propionic acid ethyl ester

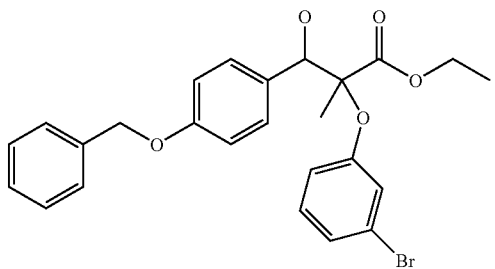

A solution of LDA (39.7 mL, 59.5 mmol, 1.5M in cyclohexane) in anhydrous THF (90 mL) was cooled to −78° C. in a dry ice/acetone bath and added to a solution of 2-(3-Bromo-phenoxy)-propionic acid ethyl ester in anhydrous THF (90 mL) also cooled to −78° C. under an atmosphere of nitrogen. After five minutes, 4-benzyloxy-benzaldehyde (6.3 g, 29.8 mmol) was added in one portion. After stirring for one minute, the reaction mixture was quenched with acetic acid (5.7 mL, 99.2 mmol, d=1.049) and a saturated solution of aqueous NH$_4$Cl (80 mL). The biphasic mixture was allowed to warm to room temperature and diluted with diethyl ether (1 L). The organic layer was washed with water, dried over MgSO$_4$, and concentrated in vacuo. The residue was purified by flash column chromatography (17% ethyl acetate in hexanes) to provide a mixture of diastereomers of 3-(4-Benzyloxy-phenyl)-2-(3-bromo-phenoxy)-3-hydroxy-2-methyl-propionic acid ethyl ester (10.0 g, 62%). $^1$H NMR (400 MHz, CDCl$_3$): • 7.42-7.28 (m, 6H), 7.19-7.00 (m, 3H), 6.95 (dd, 2H, J=6.75 Hz, 1.76 Hz), 6.73 (dd, 1H, J=6.45 Hz, 1.47 Hz), 5.21-5.02 (m, 3H), 4.24-4.14 (m, 2H), 4.08 (q, 2H, J=7.04 Hz), 3.39 (s, 1H), 1.23 (t, 3H, J=7.04 Hz). R$_f$=0.22 in 25% ethyl acetate in hexanes.

Step C

3-(4-Benzyloxy-phenyl)-2-(3-bromo-phenoxy)-2-methyl-propionic acid ethyl ester

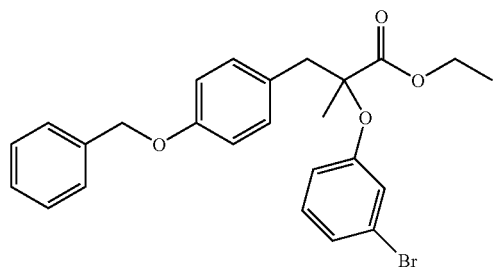

3-(4-Benzyloxy-phenyl)-2-(3-bromo-phenoxy)-3-hydroxy-2-methyl-propionic acid ethyl ester (10.0 g, 20.7 mmol) was added slowly to a −20° C. solution of triethylsilane (9.9 mL, 62.0 mmol, d=0.728) and boron trifluoride etherate (15.3 mL, 124.0 mmol, d=1.154) in anhydrous CH$_2$Cl$_2$ (370 mL). The mixture was stirred for 6 h, gradually warming to 0° C. The reaction mixture was quenched with a saturated solution of aqueous sodium carbonate and extracted with CH2Cl2. The organic layer was dried over Na$_2$SO$_4$, concentrated in vacuo, and purified by flash column chromatography to provide the titled compound (3.7 g, 38%). $^1$H NMR (400 MHz, CDCl$_3$): δ 7.46-7.33 (m, 5H), 7.18 (d, 2H, J=8.60 Hz), 7.15-7.05 (m, 3H), 6.94 (dt, 2H, J=8.60 Hz), 6.78 (dt, 1H, J=7.82 Hz, 2.35 Hz), 4.23 (q, 2H, J=7.04 Hz), 3.28 (d, 1H, J=13.69 Hz), 3.19 (d, 1H, J=13.69 Hz), 1.45 (s, 3H), 1.23 (t, 3H, J=7.04 Hz). R$_f$=0.46 in 25% ethyl acetate in hexanes.

Step D

2-(3-Bromo-phenoxy)-3-(4-hydroxy-phenyl)-2-methyl-propionic acid ethyl ester

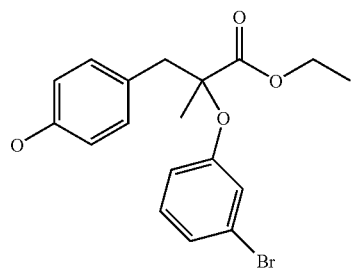

3-(4-Benzyloxy-phenyl)-2-(3-bromo-phenoxy)-2-methyl-propionic acid ethyl ester (3.7 g, 7.8 mmol) was dissolved in ethanol (140 mL), treated with 5% palladium on carbon (0.37 g), and stirred under an atmosphere of hydrogen for 2 h. The suspension was filtered through celite and concentrated in vacuo. The residue was purified by flash column chromatography (25% ethyl acetate in hexanes) to provide a mixture of the title compound and 3-(4-Hydroxy-phenyl)-2-methyl-2-phenoxy-propionic acid ethyl ester as a light yellow oil (2.8 g, 94%). $^1$H NMR (400 MHz, CDCl$_3$): δ 7.24-6.94 (m, 4H), 6.836.80 (m, 1H), 6.75-6.71 (m, 3H), 5.12 (s, 1H), 4.19 (q, 2H, J=7.04 Hz), 3.24 (d, 1H, J=13.69 Hz), 3.06 (d, 1H, J=13.69 Hz), 1.40 (s, 3H), 1.26-1.17 (m, 3H). MS [EI−] 377 (M−H)$^+$. R$_f$=0.24 in 25% ethyl acetate in hexanes.

Step E 2-(3-Bromo-phenoxy)-3-{4-[2-(2-cyclohexyl-5-methyl-oxazol-4-yl)-ethoxy]-phenyl}-2-methyl-propionic acid ethyl ester

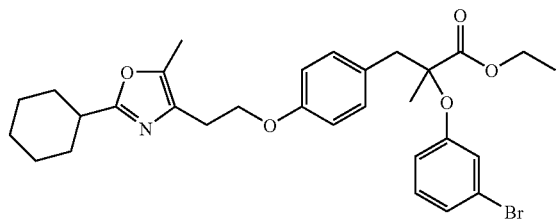

Cesium carbonate (2.98 g, 9.2 mmol) was added to a solution of 2-(3-Bromo-phenoxy)-3-(4-hydroxy-phenyl)-2-methyl-propionic acid ethyl ester, 3-(4-Hydroxy-phenyl)-2-methyl-2-phenoxy-propionic acid ethyl ester, and toluene-4-sulfonic acid 2-(2-cyclohexyl-5-methyl-oxazol-4-yl)-ethyl ester in DMF (60 mL). The resultant mixture was stirred at 65° C. under an atmosphere of nitrogen for 18 h, then diluted with diethyl ether. The organic layer was washed with 1N HCl and water, dried over MgSO$_4$, concentrated in vacuo, and purified by flash column chromatography (9% acetone in hexanes) to provide an unseparated mixture of 2-(3-Bromo-phenoxy)-3-{4-[2-(2-cyclohexyl-5-methyl-oxazol-4-yl)-ethoxy]-phenyl}-2-methyl-propionic acid ethyl ester and 3-{4-[2-(2-Cyclohexyl-5-methyl-oxazol-4-yl)-ethoxy]-phenyl}-2-methyl-2-phenoxy-propionic acid ethyl ester (3.3 g, 80%). $^1$H NMR (400 MHz, CDCl$_3$): δ 7.24-6.92 (m, 5H), 6.81-6.69 (m, 3H), 4.20-4.10 (m, 5H), 3.22 (d, 1H, J=13.69 Hz), 3.10 (d, 1H, J=13.69 Hz), 2.84 (t, 2H, J=6.65 Hz), 2.66 (tt, 1H, J=11.73 Hz, 3.52 Hz), 2.21 (s, 3H), 2.01 (d, 2H, J=13.30 Hz), 1.79-1.75 (m, 2H), 1.66 (d, 1H, J=11.73 Hz), 1.55-1.17 (m, 6H). MS [EI+] 571 (M+H)$^+$.

Step F 2-(3-Bromo-phenoxy)-3-{4-[2-(2-cyclohexyl-5-methyl-oxazol-4-yl)-ethoxy]-phenyl}-2-methyl-propionic acid

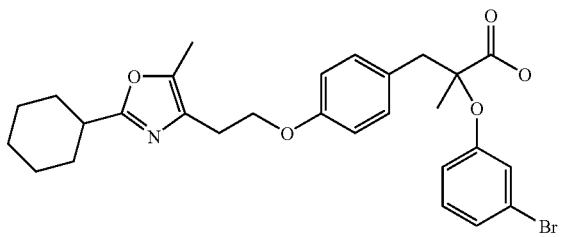

5N NaOH (0.5 mL) was added to a solution of 2-(3-Bromo-phenoxy)-3-{4-[2-(2-cyclohexyl-5-methyl-oxazol-4-yl)-ethoxy]-phenyl}-2-methyl-propionic acid ethyl ester and 3-{4-[2-(2-Cyclohexyl-5-methyl-oxazol-4-yl)-ethoxy]-phenyl}-2-methyl-2-phenoxy-propionic acid ethyl ester in ethanol (4 mL). The resultant mixture was refluxed under an atmosphere of nitrogen for 2 h, then cooled to ambient temperature. The reaction mixture was concentrated in vacuo, diluted with 1N HCl, and extracted with CH2Cl2. The organic layer was dried through a Varian ChemElut cartridge, concentrated in vacuo, and purified by LCMS. $^1$H NMR (400 MHz, CDCl$_3$): δ 7.17 (m, 5H), 6.90-6.76 (m, 3H), 4.12 (t, 2H, J=6.26 Hz), 3.22 (d, 1H, J=13.69 Hz), 3.10 (d, 1H, J=13.69 Hz), 2.95 (t, 2H, J=6.26 Hz), 2.90-2.68 (m, 1H), 2.30 (s, 3H), 2.01 (d, 2H, J=13.30 Hz), 1.79 (d, 2H, J=12.90 Hz), 1.69 (d, 1H, J=13.30 Hz), 1.40 (s, 3H), 1.58-1.21 (m, 4H). MS [EI+] 543 (M+H)$^+$.

Example 100

3-{4-[2-(2-Cyclohexyl-5-methyl-oxazol-4-yl)-ethoxy]-phenyl}-2-methyl-2-(3-thiophen-3-yl-phenoxy)-propionic acid

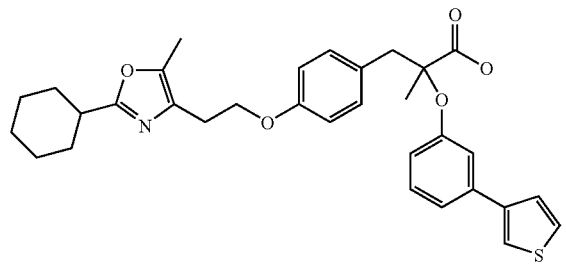

Step A

3-{4-[2-(2-Cyclohexyl-5-methyl-oxazol-4-yl)-ethoxy]-phenyl}-2-methyl-2-(3-thiophen-3-yl-phenoxy)-propionic acid ethyl ester

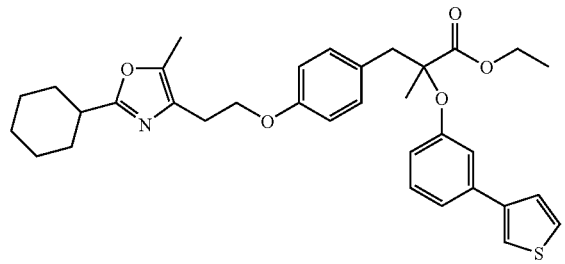

Add palladium acetate (8 mg, 0.04 mmol) to a solution of 2-(3-Bromo-phenoxy)-3-{4-[2-(2-cyclohexyl-5-methyl-oxazol-4-yl)-ethoxy]-phenyl}-2-methyl-propionic acid (0.204 g, 0.36 mmol), thiophene-3-boronic acid (91 mg, 0.71 mmol), triphenylphosphine (19 mg, 0.07 mmol), and potassium fluoride (51 mg, 1.07 mmol) in anhydrous THF (3 mL). Reflux the reaction mixture for 18 h under an atmosphere of nitrogen. Dilute the cooled reaction mixture with ethyl acetate and wash with water and brine. The organic layer was dried over Na$_2$SO$_4$, concentrated in vacuo, and purified by flash column chromatography (9% acetone in hexanes) to provide a mixture of the titled compound and 3-{4-[2-(2-Cyclohexyl-5-methyl-oxazol-4-yl)-phenyl}-2-methyl-2-phenoxy-propionic acid ethyl ester (70 mg, 34%). $^1$H NMR (400 MHz, CDCl$_3$): δ 7.38-7.19 (m, 5H), 7.13 (d, 2H, J=8.60 Hz), 7.07 (m, 1H), 6.80 (2H, J=8.60 Hz), 6.73-6.70 (m, 1H), 4.19 (q, 2H, J=7.04 Hz), 4.12 (t, 2H, J=6.65 Hz), 3.27 (d, 1H, J=13.69 Hz), 3.11 (d, 1H, J=13.69 Hz), 2.85 (t, 2H, J=6.65 Hz), 2.70-2.63 (m, 1H,), 2.22 (s, 3H), 2.01 (d, 2H, J=11.73 Hz), 1.79-1.76 (m, 2H), 1.67 (h, 1H, J=11.73 Hz), 1.59 (s, 3H), 1.56-1.46 (m, 2H), 1.41 (s, 3H), 1.37-1.23 (m, 2H), 1.20 (t, 3H, J=7.04 Hz). MS [EI+] 574 (M+H)$^+$. R$_f$=0.08 in 9% ethyl acetate in hexanes.

Step B

3-{4-[2-(2-Cyclohexyl-5-methyl-oxazol-4-yl)-ethoxy]-phenyl}-2-methyl-2-(3-thiophen-3-yl-phenoxy)-propionic acid

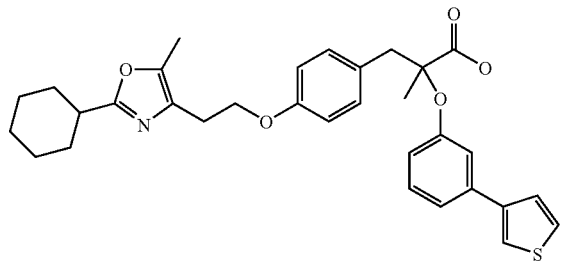

5N NaOH (0.5 mL) was added to a solution of 3-{4-[2-(2-Cyclohexyl-5-methyl-oxazol-4-yl)-ethoxy]-phenyl}-2-methyl-2-(3-thiophen-3-yl-phenoxy)-propionic acid ethyl ester and 3-{4-[2-(2-Cyclohexyl-5-methyl-oxazol-4-yl)-ethoxy]-phenyl}-2-methyl-2-phenoxy-propionic acid ethyl ester in ethanol (4 mL). The resultant mixture was refluxed under an atmosphere of nitrogen for 2 h, then cooled to ambient temperature. The reaction mixture was concentrated in vacuo, diluted with 1N HCl, and extracted with CH$_2$Cl$_2$. The organic layer was dried through a Varian ChemElut cartridge, concentrated in vacuo, and purified by LCMS. $^1$H NMR (400 MHz, CDCl$_3$): δ 7.39-7.26 (m, 5H), 7.17 (d, 2H, J=8.60 Hz), 7.11-7.10 (m, 1H), 6.82-6.80 (m, 1H), 6.78 (d, 2H, J=8.60 Hz), 4.11 (t, 2H, J=6.26 Hz), 3.25 (d, 1H, J=14.08 Hz), 3.13 (d, 1H, J=14.08 Hz), 2.93 (t, 2H, J=6.26 Hz), 2.87-2.81 (m, 1H), 2.28 (s, 3H), 1.99 (d, 2H, J=12.51 Hz), 1.77 (d, 2H, J=12.51 Hz), 1.67 (d, 2H, J=12.51 Hz), 1.57-1.46 (m, 2H), 1.45 (s, 3H), 1.37-1.19 (m, 2H). MS [ES+] m/z exact mass calcd for C$_{32}$H$_{36}$NO$_5$S 546.2314, found 546.2308.

Example 101

2-(Biphenyl-3-yloxy)-3-{4-[2-(2-cyclohexyl-5-methyl-oxazol-4-yl)-ethoxy]-phenyl}-2-methyl-propionic acid ethyl ester

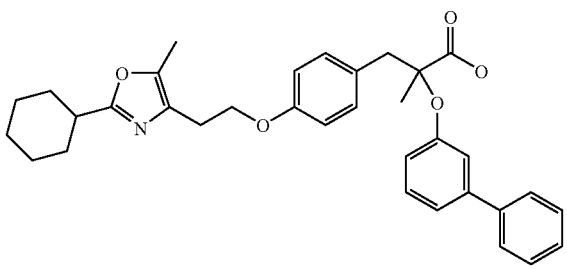

Step A 2-(Biphenyl-3-yloxy)-3-{4-[2-(2-cyclohexyl-5-methyl-oxazol-4-yl)-ethoxy]-phenyl}-2-methyl-propionic acid ethyl ester

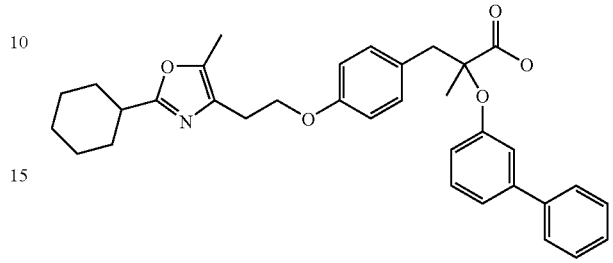

Add palladium acetate (8 mg, 0.04 mmol) to a solution of 2-(3-Bromo-phenoxy)-3-{4-[2-(2-cyclohexyl-5-methyl-oxazol-4-yl)-ethoxy]-phenyl}-2-methyl-propionic acid (0.204 g, 0.36 mmol), thiophene-3-boronic acid (91 mg, 0.71 mmol), triphenylphosphine (19 mg, 0.07 mmol), and potassium fluoride (51 mg, 1.07 mmol) in anhydrous THF (3 mL). Reflux the reaction mixture for 18 h under an atmosphere of nitrogen. Dilute the cooled reaction mixture with ethyl acetate and wash with water and brine. Dry the organic layer over Na$_2$SO$_4$, concentrate in vacuo, and purify by flash column chromatography (9% acetone in hexanes) to provide a mixture of the titled compound and 3-{4-[2-(2-Cyclohexyl-5-methyl-oxazol-4-yl)-ethoxy]-phenyl}-2-methyl-2-phenoxy-propionic acid ethyl ester. $^1$H NMR (400 MHz, CDCl$_3$): δ 7.53 (d, 1H, J=7.04 Hz), 7.41 (t, 1H, J=7.82 Hz), 7.35-7.13 (m, 6H), 7.08-6.95 (m, 1H), 6.81 (s, 4H), 4.22-4.13 (m, 4H), 3.26 (d, 1H, J=14.08 Hz), 3.14 (d, 1H, J=14.08 Hz), 2.87-2.66 (m, 3H), 2.23 (s, 3H), 2.02 (d, 2H, J=11.23 Hz), 1.80 (m, 10H), 1.21 (t, 3H, J=7.04 Hz). MS [EI+] 568 (M+H)$^+$. R$_f$=0.14 in 25% acetone in hexanes.

Step B 2-(Biphenyl-3-yloxy)-3-{4-[2-(2-cyclohexyl-5-methyl-oxazol-4-yl)-ethoxy]-phenyl}-2-methyl-propionic acid

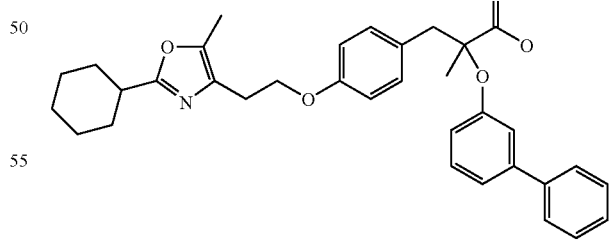

5N NaOH (0.5 mL) was added to a solution of 2-(Biphenyl-3-yloxy)-3-{4-[2-(2-cyclohexyl-5-methyl-oxazol-4-yl)-ethoxy]-phenyl}-2-methyl-propionic acid ethyl ester and 3-{4-[2-(2-Cyclohexyl-5-methyl-oxazol-4-yl)-ethoxy]-phenyl}-2-methyl-2-phenoxy-propionic acid ethyl ester in ethanol (4 mL). The resultant mixture was refluxed under an atmosphere of nitrogen for 2 h, then cooled to ambient temperature. The reaction mixture was concentrated in vacuo, diluted with 1N HCl, and extracted with CH$_2$Cl$_2$. The organic layer was dried through a Varian ChemElut cartridge, concentrated in vacuo, and purified by LCMS. $^1$H NMR (400 MHz, CDCl$_3$): δ 7.51 (d, 2H, J=7.82 Hz), 7.41 (t, 2H, J=7.04 Hz), 7.35-7.24 (m, 2H), 7.18 (d, 3H, J=8.21 Hz), 7.12-7.11 (m, 1H), 6.86 (d, 1H, J=8.60 Hz), 7.82 (d, 2H, J=8.60 Hz), 4.13 (t, 2H, J=5.47 Hz), 3.26 (d, 1H, J=14.08 Hz), 3.14 (d, 1H, J=14.08 Hz), 2.95 (t, 3H, J=5.47 Hz), 2.29 (s, 3H), 2.00 (d, 2H, J=12.51 Hz), 1.79 (d, 2H, J=13.30 Hz), 1.70-1.21 (m, 8H). MS [EI+] 540 (M+H)$^+$.

Example 104

2-Methyl-3-{4-[2-(5-methyl-2-phenyl-oxazol-4-yl)-ethoxy]-phenyl}-2-(quinolin-6-yloxy)-propionic acid Step A 2-(Quinolin-6-yloxy)-propionic acid ethyl ester

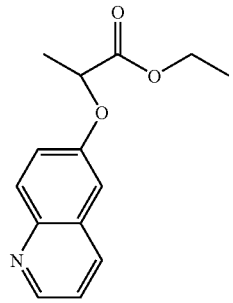

A mixture of 2-bromo-propionic acid ethyl ester (14.6 mL, 0.112 mol), quinolin-6-ol (16.3 g, 0.112 mol) and Cs$_2$CO$_3$ (44 g, 0.135 mol) in 500 mL of DMF was heated to 90° C. for overnight. The mixture was filtered and diluted with Et$_2$O (500 mL). Organic layer was washed with water and brine. The combined aqueous layer was then extracted with EtOAc. Combined organic layer was washed with water and brine, dried over Na$_2$SO$_4$, filtered and concentrated. Crude material was purified by chromatography (R$_f$=0.3 in hexanes/acetone=1:1) to give 22 g of title compound as light yellow oil. $^1$H NMR (400 MHz, CDCl$_3$) δδ8.78 (dd, 1H, J=4.0, 0.8 Hz), 8.02 (d, 1H, J=8.8 Hz), 8.01 (d, 1H, J=8.0 Hz), 7.42 (dd, 1H, J=9.4, 3.0 Hz), 7.35 (dd, 1H, J=8.6, 4.2 Hz), 7.26 (d, 1H, J=1.2 Hz), 6.99 (d, 1H, J=2.8 Hz), 4.89 (q, 1H, J=6.8 Hz), 4.27-4.20 (m, 2H), 1.69 (d, 3H, J=6.8 Hz), 1.24 (t, 3H, J=6.8 Hz).

Step B 3-(4-Benzyloxy-phenyl)-2-methyl-2-(quinolin-6-yloxy)-propionic acid ethyl ester

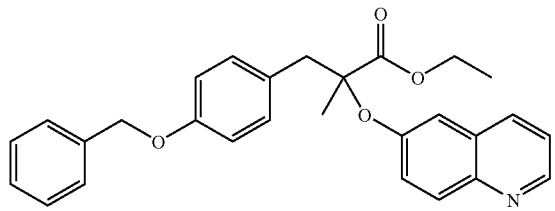

To a LDA solution (42 mL, 1.5 M solution in THF) in 65 mL of dry THF at −78° C., a solution of 2-(quinolin-6-yloxy)-propionic acid ethyl ester (8.61 g, 0.035 mol) in 65 mL of dry THF was cannulated in. The resulting solution is allowed to stand at −78° C. for 3 min. Solid 4-benzyloxy-benzaldehyde (6.71 g, 0.032 mol) was added and resulting mixture was allowed to stand at −78° C. for 5 min until all solid dissovled in the solution. Reaction was then quenched with AcOH (6.03 mL, 0.105 mol) in 60 mL of THF at −78° C. The mixture was then diluted with Et$_2$O and washed with sat'NH4Cl, water and brine, dried over Na$_2$SO$_4$, filtered and concentrated. The crude material was purified by chromatography to give 3-(4-benzyloxy-phenyl)-3-hydroxy-2-methyl-2-(quinolin-6-yloxy)-propionic acid ethyl ester in 86% yield. A of solution of 2.75 g of give 3-(4-benzyloxy-phenyl)-3-hydroxy-2-methyl-2-(quinolin-6-yloxy)-propionic acid ethyl ester (6.01 mmol), trifluoroacetic acid (2.8 mL, 36.1 mmol), triethylsilane (5.8 mL, 36.1 mmol) in 80 mL of dichloroethane was heated to reflux for 50 h. The mixture was cooled to r.t. and diluted with Et$_2$O and washed with sat' NaHCO$_3$, water and brine. Organic layer was dried over Mg SO$_4$, filtered and concentrated. Residue was purified by chromatography (5% MeOH in CH$_2$Cl$_2$) to give 86% of title compound as light yellow oil. $^1$H NMR (400 MHz, CDCl$_3$) δδ8.78 (dd, 1H, J=4.4, 1.6 Hz), 8.00 (d, 1H, J=9.2 Hz), 7.98 (d, 1H, J=8.8 Hz), 7.45-7.32 (m, 7H), 7.19 (d, 2H, J=8.8 Hz), 7.04 (d, 1H, J=3.2 Hz), 6.93 (d, 2H, J=8.8 Hz), 5.06 (s, 2H), 4.23 (q, 2H, J=7.1 Hz), 3.38, 3.18 (ABq, 2H, J=13.8 Hz), 1.53 (s, 3H), 1.19 (t, 3H, J=7.1 Hz). MS (ES$^+$) m/z mass calcd for C$_{28}$H$_{28}$O$_4$ (m+1) 442, found 442.

Step C 3-(4-Hydroxy-phenyl)-2-methyl-2-(quinolin-6-yloxy)-propionic acid ethyl ester

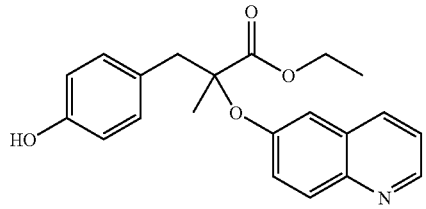

A solution of 3-(4-Benzyloxy-phenyl)-2-methyl-2-(quinolin-6-yloxy)-propionic acid ethyl ester (2.65 g, 6.0 mmol) in 100 mL of EtOH with 5% Pd/C (530 mg, 20 w %) was allowed to stand under 1 atm H2 for 6 h. Catalyst was filtered off and organic solvent was removed under vacuum. Residue was then dissolved in 200 mL of toluene. 530 mg of 10% Pd/C was added. The mixture was heated to reflux under air for overnight. Reaction was cooled to r.t. and catalyst was filtered off. Organic solvent was removed under vacuum and crude material was clean for next step without further purification. $^1$H NMR (400 MHz, CDCl$_3$) δδ8.77 (dd, 1H, J=4.0, 1.4 Hz), 8.04 (d, 1H, J=7.6 Hz), 8.02 (d, 1H, J=9.6 Hz), 7.38 (dd, 1H, J=8.4, 4.4 Hz), 7.32 (dd, 1H, J=9.2, 2.8 Hz), 7.09 (d, 2H, J=8.8 Hz), 7.03 (d, 1H, J=2.8 Hz), 6.83 (d, 2H, J=8.8 Hz), 4.22 (q, 2H, J=7.1 Hz), 3.35, 3.13 (ABq, 2H, J=13.6 Hz), 1.52 (s, 3H), 1.19 (t, 3H, J=7.1 Hz). MS (ES$^+$) m/z mass calcd for C$_{21}$H$_{22}$NO$_4$ (m+1) 352, found 352.

Step D

2-Methyl-3-{4-[2-(5-methyl-2-phenyl-oxazol-4-yl)-ethoxy]-phenyl}-2-(quinolin-6-yloxy)-propionic acid

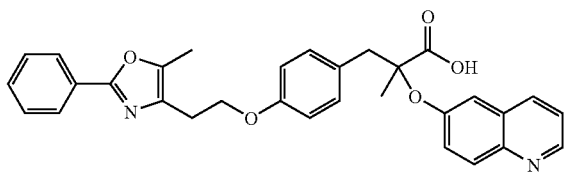

A solution of toluene-4-sulfonic acid 2-(5-methyl-2-phenyl-oxazol-4-yl)-ethyl ester (94 mg, 0.26 mmol), 3-(4-Hydroxy-phenyl)-2-methyl-2-(quinolin-6-yloxy)-propionic acid ethyl ester (77.3 mg, 0.22 mmol) and K2CO3 (61 mg, 0.44 mmol) in 2 mL of EtOH was heated to 80° C. for overnight. Then 5N NaOH (0.26 mL, 1.3 mmol) was added and reaction mixture was stand at same temperature for 2 h. The mixture was cooled off to r.t. and organic solvent was removed under vacuum. Residue was then dissolved in CH2Cl2 and 1N HCl. Aqueous layer was washed with CH2Cl2 (2×). Combined organic layer was washed with brine, dried over Na2SO4, filtered and concentrated. Residue was purified by MS/LC to give title compound as white solid (55.6 mg, 50%). $^1$H NMR (400 MHz, CDCl$_3$) δδ8.76 (d, 1H, J=4.4 Hz), 8.28 (d, 1H, J=8.4 Hz), 7.94 (d, 1H, J=9.2 Hz), 7.89-7.87 (m, 2H), 7.51-7.45 (m, 3H), 7.38-7.32 (m, 2H), 7.25-7.23 (m, 1H), 7.20 (d, 1H, J=2.4 Hz), 7.16 (d, 2H, J=8.8 Hz), 6.85 (d, 2H, J=8.8 Hz), 4.17 (t, 2H, J=6.6 Hz), 3.29, 3.11 (ABq, 2H, J=13.4 Hz), 2.90 (t, 2H, J=6.6 Hz), 2.33 (s, 3H), 1.42 (s, 3H). HRMS (ES$^4$) m/z exact mass calcd for $C_{31}H_{29}N_2O_5$ (m+1) 509.2076, found 509.2095.

Example 105

3-{4-[2-(2-Cyclohexyl-5-methyl-oxazol-4-yl)-ethoxy]-phenyl}-2-methyl-2-(quinolin-6-yloxy)-propionic acid

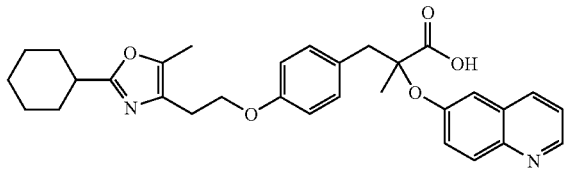

A solution of Toluene-4-sulfonic acid 2-(2-cyclohexyl-5-methyl-oxazol-4-yl)-ethyl ester (96 mg, 0.26 mmol), 3-(4-Hydroxy-phenyl)-2-methyl-2-(quinolin-6-yloxy)-propionic acid ethyl ester (77.3 mg, 0.22 mmol) and K$_2$CO$_3$ (61 mg, 0.44 mmol) in 2 mL of EtOH was heated to 80° C. for overnight. Then 5N NaOH (0.26 mL, 1.3 mmol) was added and reaction mixture was stand at same temperature for 2 h. The mixture was cooled off to r.t. and organic solvent was removed under vacuum. Residue was then dissolved in CH$_2$Cl$_2$ and 1N HCl. Aqueous layer was washed with CH$_2$Cl$_2$ (2×). Combined organic layer was washed with brine, dried over Na$_2$SO$_4$, filtered and concentrated. Residue was purified by MS/LC to give title compound as white solid (54.5 mg, 48%). $^1$H NMR (400 MHz, CDCl$_3$) δδ8.74 (dd, 1H, J=4.0, 1.6 Hz), 8.24 (d, 1H, J=6.8 Hz), 7.92 (d, 1H, J=9.2 Hz), 7.45 (dd, 1H, J=8.2, 4.2 Hz), 7.33 (dd, 1H, J=5.2, 2.8 Hz), 7.19 (d, 1H, J=2.8 Hz), 7.15, 6.82 (ABq, 4H, J=8.6 Hz), 4.08 (t, 2H, J=6.8 Hz), 3.29, 3.11 (ABq, 2H, J=13.8 Hz), 2.76 (t, 2H, J=6.8 Hz), 2.68-2.63 (m, 1H), 2.18 (s, 3H), 1.93-1.87 (m, 2H), 1.71-1.65 (m, 2H), 1.62-1.57 (m, 1H), 1.46-1.14 (m, 5H), 1.42 (s, 3H). HRMS (ES$^+$) m/z exact mass calcd for $C_{31}H_{35}N_2O_5$ (m+1) 515.2546, found 515.2567.

Additional compounds of the present invention, having the structural formula shown below, were synthesized by methods similar to those described in the previous examples.

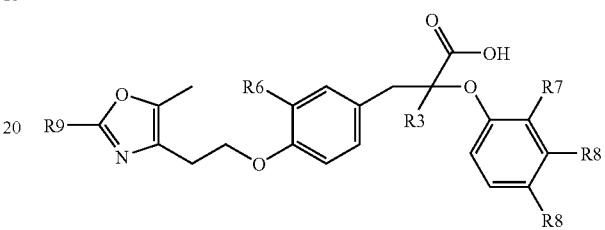

These additional compounds are further exemplified in the following table.

TABLE I

| Example | R9 | R6 | R3 | R7 | meta R8 | para R8 |
|---------|----|----|----|----|---------|---------|
| 92 | phenyl | H | CH3 | H | H | OCH3 |
| 93 | cyclohexyl | H | CH3 | H | t-butyl | H |
| 94 | phen-butyl | H | CH3 | H | H | H |
| 95 | phenyl | OCH3 | CH3 | H | H | H |
| 96 | morpholino | H | CH3 | H | H | H |
| 97 | phenethyl | H | CH3 | H | H | H |
| 98 | phenethyl | H | CH3 | H | H | t-butyl |
| 99 | phenethyl | H | CH3 | H | H | F |
| 100 | phenethyl | H | CH3 | H | OCH3 | H |
| 101 | phenethyl | H | CH3 | H | CH3 | H |
| 102 | phenethyl | H | CH3 | H | CF3 | H |
| 103 | phenethyl | H | CH3 | H | H | CF3 |
| 104 | phenethyl | H | CH3 | H | F | H |
| 105 | phenethyl | H | CH3 | H | H | Cl |
| 106 | phenethyl | H | C2H5 | H | H | H |
| 107 | phenethyl | H | CH3 | H | H | OCF3 |
| 108 | benzyl | H | CH3 | H | H | F |
| 109 | benzyl | H | CH3 | H | OCH3 | H |
| 110 | benzyl | H | CH3 | H | CH3 | H |
| 111 | benzyl | H | CH3 | H | CF3 | H |
| 112 | benzyl | H | CH3 | H | H | CF3 |
| 113 | benzyl | H | CH3 | H | F | H |
| 114 | benzyl | H | CH3 | H | H | Cl |
| 115 | benzyl | H | C2H5 | H | H | H |
| 116 | benzyl | H | CH3 | H | H | OCF3 |
| 117 | ![C2H5-substituted phenyl] | H | CH3 | H | H | H |
| 118 | ![Br-thienyl-methyl] | H | CH3 | H | H | H |
| 119 | 1-methyl-cyclohexyl | H | CH3 | H | H | CF3 |
| 120 | 3-thienyl | H | CH3 | H | H | H |
| 121 | phenyl | H | CH3 | OCH3 | H | H |

TABLE I-continued

| Example | R9 | R6 | R3 | R7 | meta R8 | para R8 |
|---|---|---|---|---|---|---|
| 122 | 2-thienyl | H | CH3 | OCH3 | H | H |
| 123 | cyclohexyl | H | CH3 | OCH3 | H | H |
| 124 | 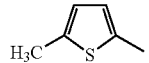 | H | CH3 | H | H | CH3 |
| 125 | phenyl | H | CH3 | CH3 | H | H |
| 126 | 2-thienyl | H | CH3 | CH3 | H | H |
| 127 | cyclohexyl | H | CH3 | CH3 | H | H |
| 128 | 1-methyl-cyclohexyl | H | CH3 | CH3 | H | H |
| 129 | t-butyl | H | CH3 | H | H | H |
| 130 | 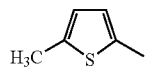 | H | CH3 | H | H | CF3 |
| 131 | cyclohexyl | H | CH3 | H | H | t-butyl |
| 132 | morpholino | H | CH3 | H | H | t-butyl |
| 133 | cyclohexyl | H | CH3 | H | 3-thienyl | H |
| 134 | cyclohexyl | H | CH3 | H | phenyl | H |
| 135 | cyclohexyl | H | CH3 | H | Br | H |
| 136 | cyclohexyl | H | CH3 | H | H | t-butyl |
| 137 | phenyl | H | CH3 | H | Cl | H |
| 138 | 2-thienyl | H | CH3 | H | Cl | H |
| 139 | 1-methyl-cyclohexyl | H | CH3 | H | Cl | H |
| 140 | 1-methyl-cyclohexyl | H | CH3 | F | H | H |

Other compounds of the present invention, having the structural formula shown below, were also synthesized by methods similar to those described in the previous examples.

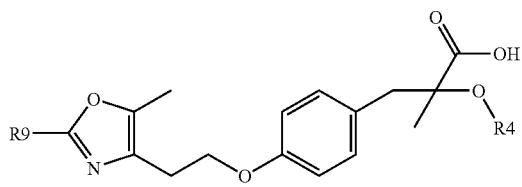

These additional compounds are further exemplified in the following table.

TABLE II

| Example | R9 | R4 |
|---|---|---|
| 141 | phenyl | quinolyl |
| 142 | 2-thienyl | quinolyl |
| 143 | cyclohexyl | quinolyl |
| 144 | phenyl | 1,2,3,4-tetrahydronaphthyl |
| 145 | cyclohexyl | 1,2,3,4-tetrahydronaphthyl |
| 146 | 1-methyl-cyclohexyl | 1,2,3,4-tetrahydronaphthyl |
| 147 | phenyl | pyridyl |

Binding and Cotransfection Studies

The in vitro potency of compounds in modulating PPAR• and PPAR• receptors were determined by the procedures detailed below. DNA-dependent binding (ABCD binding) was carried out using SPA technology with PPAR receptors. Tritium-labeled PPARα and PPARγ agonists were used as radioligands for generating displacement curves and $IC_{50}$ values with compounds of the invention. Cotransfection assays were carried out in CV-1 cells. The reporter plasmid contained an acylCoA oxidase (AOX) PPRE and TK promoter upstream of the luciferase reporter cDNA. Appropriate PPARs and RXRα were constitutively expressed using plasmids containing the CMV promoter. For PPARα and PPARβ, interference by endogenous PPARγ in CV-1 cells was an issue. In order to eliminate such interference, a GAL4 chimeric system was used in which the DNA binding domain of the transfected PPAR was replaced by that of GAL4, and the GAL4 response element was utilized in place of the AOX PPRE. Cotransfection efficacy was determined relative to PPARα agonist and PPARγ agonist reference molecules. Efficacies were determined by computer fit to a concentration-response curve, or in some cases at a single high concentration of agonist (10 μM). For binding or cotransfection studies with receptors other than PPARs, similar assays were carried out using appropriate ligands, receptors, reporter constructs, etc., for that particular receptor.

These studies were carried out to evaluate the ability of compounds of the invention to bind to and/or activate various nuclear transcription factors, particularly huPPARα ("hu" indicates "human") and huPPARγ. These studies provide in vitro data concerning efficacy and selectivity of compounds of the invention. Furthermore, binding and cotransfection data for compounds of the invention were compared with corresponding data for marketed compounds that act on either huPPARα or huPPARγ.

Binding and cotransfection data for representative compounds of the invention are compared with corresponding data for reference compounds in Table III.

TABLE III

Comparison of binding $IC_{50}$ values and cotransfection efficacy data of compounds of the invention to reference compounds.

| | huPPARα | | huPPARγ | |
|---|---|---|---|---|
| Example | $IC_{50}$ (nM) | CTF Efficacy (%) | $IC_{50}$ (nM) | CTF Efficacy (%) |
| 1 | 40 | 70 | 10 | 79 |
| 2 | 1250 | 59 | 476 | 400 |
| 3 | 22 | 70 | 7 | 74 |
| 4 | 39 | 80 | 9 | 63 |
| 5 | 542 | 65 | 170 | 75 |
| 6 | 23 | 72 | 7 | 70 |
| 7 | 27 | 82 | 58 | 72 |
| 8 | 63 | 54 | 24 | 75 |
| 9 | 41 | 61 | 11 | 73 |
| 17 | 68 | 129 | 67 | 105 |
| 18 | 72 | 102 | 60 | 112 |
| 19 | 85 | 64 | 80 | 23 |
| 22 | 70 | 51 | 85 | 12 |
| 23 | 63 | 40 | 81 | 17 |
| 25 | 73 | 95 | 70 | 106 |
| 27 | 75 | 46 | 76 | 15 |
| 29 | 116 | 65 | 48 | 82 |
| 31 | 53 | 63 | 19 | 73 |
| 34 | 91 | 112 | 77 | 76 |
| 35 | 66 | 78 | 79 | 21 |
| 36 | 72 | 70 | 88 | 21 |
| 40 | 50 | 77 | 10 | 110 |
| 41 | 66 | 49 | 109 | 11 |
| 44 | 157 | 54 | 159 | 73 |
| 49 | 175 | 63 | 655 | 58 |
| 51 | 64 | 152 | 80 | 48 |
| 52 | 62 | 108 | 76 | 61 |
| 58 | 60 | 149 | 66 | 41 |
| 61 | 64 | 52 | 84 | 12 |

TABLE III-continued

Comparison of binding IC$_{50}$ values and cotransfection efficacy data of compounds of the invention to reference compounds.

| Example | huPPARα | | huPPARγ | |
| --- | --- | --- | --- | --- |
| | IC$_{50}$ (nM) | CTF Efficacy (%) | IC$_{50}$ (nM) | CTF Efficacy (%) |
| 62 | 58 | 101 | 79 | 35 |
| 64 | 67 | 50 | 112 | 11 |
| 65 | 71 | 46 | 82 | 24 |
| 67 | 61 | 34 | 65 | 11 |
| 71 | 78 | 142 | 81 | 50 |
| 76 | 76 | 63 | 83 | 24 |
| 78 | 75 | 52 | 89 | 17 |
| 80 | 76 | 84 | 80 | 30 |
| 86 | 55 | 24 | 72 | 7 |
| 88 | 58 | 61 | 16 | 78 |
| 91 | 215 | 47 | 51 | 62 |
| Troglitazone | 94,500 | 0 | 1180 | 80 |
| Fenofibric acid | 68,000 | 16 | 125,000 | 0 |

Evaluation of Triglyceride and Cholesterol Level in HuapoAI Transgenic Mice

Five to six week old male mice, transgenic for human apoAI [C57B1/6-tgn(apoa1)1rub, Jackson Laboratory, Bar Harbor, Me.] were housed five per cage (10"×20"×8" with aspen chip bedding) with food (Purina 5001) and water available at all times. After an acclimation period of 2 weeks, animals were individually identified by ear notches, weighed, and assigned to groups based on body weight. Beginning the following morning, mice were dosed daily by oral gavage for 7 days using a 20 gauge, 1½" curved disposable feeding needle (Popper & Sons). Treatments were test compounds (30 mg/kg), a positive control (fenofibrate, 100 mg/kg) or vehicle [1% carboxymethylcellulose (w/v)/0.25% Tween80 (w/v); 0.2 ml/mouse]. Prior to termination on day 7, mice were weighed and dosed. Three hours after dosing, animals were anesthetized by inhalation of isoflurane (2-4%; Abbott Laboratories, Chicago, Ill.) and blood obtained via cardiac puncture (0.7-1.0 ml). Whole blood was transferred to serum separator tubes (Vacutainer SST), chilled on ice, and permitted to clot. Serum was obtained after centrifugation at 4° C. and frozen until analysis for triglycerides, total cholesterol, compound levels, and serum lipoprotein profile by fast protein liquid chromatography (FPLC) coupled to an inline detection system. After sacrifice by cervical dislocation, the liver, heart and epididymal fat pads were excised and weighed.

The animals dosed with vehicle had average triglycerides values of 60-80 mg/dl, which were reduced by the positive control fenofibrate (33-58 mg/dl with a mean reduction of 37%). The animals dosed with vehicle had average total serum cholesterol values of 140-180 mg/dl, which were increased by fenofibrate (190-280 mg/dl, with a mean elevation of 41%). Triglyceride serum levels for animals receiving compounds of the invention are reported in Table IV in mg/dl. When subject to FPLC analysis, pooled sera from vehicle-treated hu apoAI transgenic mice had a high density lipoprotein cholesterol (HDLc) peak area which ranged from 47 v-sec to 62 v-sec. Fenofibrate increased the amount of HDLc (68-96 v-sec with a mean percent increase of 48%). Test compounds are reported in terms of percent increase in the area under the curve as indicated in Table V.

TABLE IV

Triglyceride serum levels in mice receiving a compound of the invention.

| Example | Reduction in Triglyceride Serum Level (Percent) |
| --- | --- |
| 1 | 41.3 |
| 2 | -12.9 |
| 4 | 58.3 |
| 5 | 19.7 |
| 6 | 38.5 |
| 7 | 42.1 |
| 9 | 19.8 |
| 17 | 78.7 |
| 18 | 69.0 |
| 19 | 40.0 |
| 22 | 19.5 |
| 23 | 52.5 |
| 25 | 35.5 |
| 27 | 36.8 |
| 34 | 57.1 |
| 35 | 32.3 |
| 36 | 23.0 |
| 40 | 77.6 |
| 41 | 57.8 |
| 51 | 72.8 |
| 52 | 75.9 |
| 58 | 26.5 |
| 61 | 17.6 |
| 62 | 2.5 |
| 64 | 43.0 |
| 65 | 54.0 |
| 67 | 67.8 |
| 76 | 27.1 |
| 78 | 64.8 |
| 80 | 36.6 |
| 86 | 30.1 |

TABLE V

Percent increase of HDLc serum levels in mice receiving a compound of the invention over mice receiving vehicle

| Example | % HDLc Increase |
| --- | --- |
| 1 | 83 |
| 2 | 25 |
| 3 | 67 |
| 4 | 24 |
| 5 | 30 |
| 6 | 85 |
| 7 | 39 |
| 8 | 34 |
| 9 | 123 |
| 17 | 119 |
| 18 | 141 |
| 19 | 89 |
| 22 | 29 |
| 23 | 54 |
| 25 | 8 |
| 27 | 49 |
| 29 | 78 |
| 31 | 114 |
| 34 | 95 |
| 35 | 77 |
| 36 | 30 |
| 40 | 131 |
| 41 | 96 |
| 44 | 151 |
| 49 | 17 |
| 51 | 122 |
| 52 | 185 |
| 58 | 74 |
| 61 | 72 |

TABLE V-continued

Percent increase of HDLc serum levels in mice receiving a compound of the invention over mice receiving vehicle

| Example | % HDLc Increase |
|---|---|
| 62 | 72 |
| 64 | 66 |
| 65 | 75 |
| 67 | 76 |
| 71 | 34 |
| 76 | 26 |
| 78 | 95 |
| 80 | 123 |
| 86 | 36 |
| 88 | 86 |
| 91 | 46 |

Evaluation of Glucose Levels in db/db Mice

Five week old male diabetic (db/db) mice [C57BlKs/j-m+/+ Lepr(db), Jackson Laboratory, Bar Harbor, Me.] or lean littermates (db+) were housed 6 per cage (10"×20"×8" with aspen chip bedding) with food (Purina 5015) and water available at all times. After an acclimation period of 2 weeks, animals were individually identified by ear notches, weighed, and bled via the tail vein for determination of initial glucose levels. Blood was collected (100 µl) from unfasted animals by wrapping each mouse in a towel, cutting the tip of the tail with a scalpel, and milking blood from the tail into a heparinized capillary tube (Fisher) balanced on the edge of the bench. Sample was discharged into a heparinized microtainer with gel separator (VWR) and retained on ice. Plasma was obtained after centrifugation at 4° C. and glucose measured immediately. Remaining plasma was frozen until the completion of the experiment, when glucose and triglycerides were assayed in all samples. Animals were grouped based on initial glucose levels and body weights. Beginning the following morning, mice were dosed daily by oral gavage for 7 days using a 20 gauge, 1½" curved disposable feeding needle. Treatments were test compounds (30 mg/kg), a positive control agent (30 mg/kg) or vehicle [1% carboxymethylcellulose (w/v)/0.25% Tween80 (w/v); 0.3 ml/mouse]. On day 7, mice were weighed and bled (tail vein) 3 hours after dosing. Twenty-four hours after the $7^{th}$ dose (i.e., day 8), animals were bled again (tail vein). Samples obtained from conscious animals on days 0, 7 and 8 were assayed for glucose. After the 24 hour bleed, animals were weighed and dosed for the final time. Three hours after dosing on day 8, animals were anesthetized by inhalation of isoflurane and blood obtained via cardiac puncture (0.5-0.7 ml). Whole blood was transferred to serum separator tubes, chilled on ice and permitted to clot. Serum was obtained after centrifugation at 4° C. and frozen until analysis for compound levels. After sacrifice by cervical dislocation, the liver, heart and epididymal fat pads were excised and weighed.

The animals dosed with vehicle had average triglycerides values of 170-230 mg/dl, which were reduced by the positive PPARγ control (70-120 mg/dl with a mean reduction of 50%). Male db/db mice were hyperglycemic (average glucose of 680-730 mg/dl on the $7^{th}$ day of treatment), while lean animals had average glucose levels between 190-230 mg/dl. Treatment with the positive control agent reduced glucose significantly (350-550 mg/dl with a mean decrease towards normalization of 56%). Test compounds are reported in Table VI in terms of glucose normalization (i.e., 100% normalization would be glucose levels in treated db/db mice which did not differ from lean values.

Glucose was measured calorimetrically using commercially purchased reagents (Sigma #315-500). According to the manufacturers, the procedures were modified from published work (McGowan, M. W., Artiss, J. D., Strandbergh, D. R. & Zak, B. Clin Chem, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays were further modified in our laboratory for use in a 96 well format. Standards (Sigma #339-11, Sigma #16-11, and Sigma #CC0534 for glucose, triglycerides and total cholesterol, respectively), quality control plasma (Sigma # A2034), and samples (2 or 5 µl/well) were measured in duplicate using 200 µl of reagent. An additional aliquot of sample, pipetted to a third well and diluted in 200 µl water, provided a blank for each specimen. Plates were incubated at room temperature (18, 15, and 10 minutes for glucose, triglycerides and total cholesterol, respectively) on a plate shaker (DPC Micormix 5) and absorbance read at 500 nm (glucose and total cholesterol) or 540 nm (triglycerides) on a plate reader (Wallac Victor 1420). Sample absorbances were compared to a standard curve (100-800, 10-500, and 100-400 mg/dl for glucose, triglycerides and total cholesterol, respectively). Values for the quality control sample were always within the expected range and the coefficient of variation for samples was below 10%. All samples from an experiment were assayed at the same time to minimize inter-assay variability.

Serum lipoproteins were separated and cholesterol quantitated with an in-line detection system. Sample was applied to a Superose® 6 HR 10/30 size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol was monitored in the flow stream at 505 nm and the analog voltage from the monitor was converted to a digital signal for collection and analysis. The change in voltage corresponding to change in cholesterol concentration was plotted vs time and the area under the curve corresponding to the elution of VLDL, LDL and HDL was calculated using Perkin Elmer Turbochrome software.

TABLE VI

Percent glucose normalisation values in db/db mice.

| Example | Glucose Normalisation |
|---|---|
| 1 | 95 |
| 2 | 9 |
| 3 | 85 |
| 4 | 74 |
| 5 | 80 |
| 6 | 86 |
| 7 | 86 |
| 8 | 97 |
| 9 | 95 |

TABLE VI-continued

Percent glucose normalisation values in db/db mice.

| Example | Glucose Normalisation |
|---|---|
| 17 | 112 |
| 18 | 110 |
| 19 | 95 |
| 22 | 85 |
| 23 | 97 |
| 25 | 73 |
| 27 | 86 |
| 29 | 86 |
| 34 | 80 |
| 35 | 84 |
| 36 | 92 |
| 40 | 103 |
| 41 | 101 |
| 44 | 83 |
| 51 | 88 |
| 52 | 98 |
| 58 | 81 |
| 61 | 79 |
| 62 | 79 |
| 64 | 97 |
| 65 | 99 |
| 67 | 96 |
| 71 | 97 |
| 76 | 97 |
| 78 | 86 |
| 80 | 83 |
| 86 | 92 |
| 88 | 92 |
| 91 | 71 |

Equivalents

While this invention has been particularly shown and described with references to preferred embodiments thereof, it will be understood by those skilled in the art that various changes in form and details may be made therein without departing from the scope of the invention encompassed by the appended claims.

We claim:

1. A compound represented by the following structural formula:

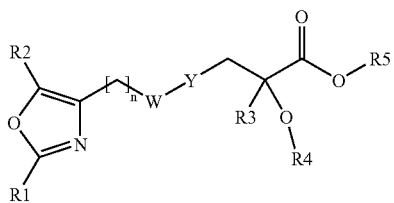

or a pharmaceutically acceptable salt and hydrate thereof, wherein:
(a) R1 is a non-heterocyclic group selected from the group consisting of aryl, cycloalkyl, aryl-C1-C4 alkyl, cycloalkyl-C1-C4 alkyl, and t-butyl, wherein the aryl and cycloalkyl groups are each optionally substituted with substituents selected from the group consisting of halo, carboxyl, C1-C4 alkyl, C1-C4 alkoxy, C1-C4 haloalkyl, C1-C4 haloalkoxy, nitro, cyano, CHO, hydroxyl, C1-C4 alkanoic acid and —C(O)NR13R13 in which each R13, independently, H or a C1-C4 alkyl;
(b) R2 is selected from the group consisting of H, C1-C4 alkyl, C1-C4 haloalkyl and phenyl;
(c) n is 2, 3, or 4;
(d) W is selected from the group consisting of $CH_2$, CH(OH), C(O) and O;
(e) Y is an unsubstituted or substituted group selected from the group consisting of thiophen-2,5-diyl and phenylene wherein the thiophen-2,5-diyl substituents are selected from the group consisting of H, C1-C4 alkyl, C1-C4 alkoxy, C1-C4 haloalkyl and C1-C4 haloalkoxy;
(f) R3 is a C1-C4 alkyl or C1-C4 haloalkyl;
(g) R4 is selected from the group consisting of a substituted or unsubstituted phenyl, naphthyl, 1,2,3,4-tetrahydronaphthyl, and benzo[1,3]dioxol-5-yl group, wherein the substituents are selected from the group consisting of halo, carboxyl, C1-C4 alkyl, C1-C4 alkoxy, C1-C4 haloalkyl, C1-C4 haloalkoxy, nitro, cyano, CHO, hydroxyl, C1-C4 alkanoic acid and —C(O)NR13R13 in which each R13, independently, H or a C1-C4 alkyl; and
(h) R5 is selected from the group consisting of H, C1-C4 alkyl, and aminoalkyl.

2. The compound of claim 1, wherein the compound is 3-{4-[2-(2-phenyl-5-methyl-oxazol-4-yl)-ethoxy]-phenyl}-2-methyl-2-phenoxy-propionic acid; or (S)-3-{4-[2-(2-phenyl-5-methyl-oxazol-4-yl)-ethoxy]-phenyl}-2-methyl-2-phenoxy-propionic acid.

3. The compound of claim 1, wherein the compound is 3-{4-[2-(2-cyclohexyl-5-methyl-oxazol-4-yl)-ethoxy]-phenyl}-2-p-tolyloxy-propionic acid, or (S)-3-{4-[2-(2-cyclohexyl-5-methyl-oxazol-4-yl)-ethoxy]-phenyl}-2-p-tolyloxy-propionic acid.

4. A compound of claim 1 represented by the following structural formula:

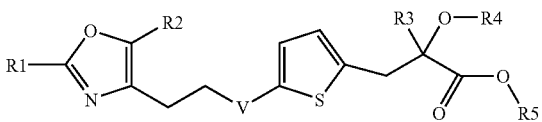

or a pharmaceutically acceptable salt and hydrate thereof, wherein:
(a) R1 is a non-heterocyclic group selected from the group consisting of aryl, cycloalkyl, aryl-C1-C4 alkyl, cycloalkyl-C1-C4 alkyl, and t-butyl, wherein the aryl and cycloalkyl groups are each optionally substituted with substituents selected from the group consisting of halo, carboxyl, C1-C4 alkyl, C1-C4 alkoxy, C1-C4 haloalkyl, C1-C4 haloalkoxy, nitro, cyano, CHO, hydroxyl, C1-C4 alkanoic acid and —C(O)NR13R13 in which each R13, independently, H or a C1-C4 alkyl;
(b) R2 is selected from the group consisting of H, C1-C4 alkyl, C1-C4 haloalkyl and phenyl;
(c) V is selected from the group consisting of C, C(OH) or C(O);
(d) R3 is selected from the group consisting of C1-C4 alkyl and C1-C4 haloalkyl;
(e) R4 is a substituted or unsubstituted group selected from the group consisting of phenyl, naphthyl, 1,2,3,4-tetrahydronaphthyl, and benzo[1,3]dioxol-5-yl group, wherein the substituents are selected from the group consisting of halo, carboxyl, C1-C4 alkyl, C1-C4 alkoxy, C1-C4 haloalkyl, C1-C4 haloalkoxy, nitro, cyano, CHO, hydroxyl, C1-C4 alkanoic acid and —C(O)NR13R13 in which each R13, independently, H or a C1-C4 alkyl; and (f) R5 is selected from the group consisting of H, C1-C4 alkyl, and aminoalkyl.

5. The compound of claim 1, wherein the compound is selected from the group consisting of:
- 3-{4-[2-(2-Cyclohexyl-5-methyl-oxazol-4-yl)-ethoxy]-phenyl}-2-(2-methoxy-phenoxy)-2-methyl-propionic acid;
- 2-Methyl-3-{4-[2-(5-methyl-2-phenyl-oxazol-4-yl)-ethoxy]-phenyl}-2-o-tolyloxy-propionic acid;
- 2-Methyl-3-(4-{2-[5-methyl-2-(1-methyl-cyclohexyl)-oxazol-4-yl]-ethoxy}-phenyl)-2-o-tolyloxy-propionic acid;
- 3-{4-[2-(2-Cyclohexyl-5-methyl-oxazol-4-yl)-ethoxy]-phenyl}-2-methyl-2-o-tolyloxy-propionic acid;
- 2-Methyl-3-(4-{2-[5-methyl-2-(1-methyl-cyclohexyl)-oxazol-4-yl]-ethoxy}phenyl)-2-o-tolyloxy-propionic acid;
- 2-(Biphenyl-3-yloxy)-3-{4-[2-(2-cyclohexyl-5-methyl-oxazol-4-yl)-ethoxy]-phenyl}-2-methyl-propionic acid ethyl ester;
- 2-(3-Chloro-phenoxy)-3-{4-[2-(2-cyclohexyl-5-methyl-oxazol-4-yl)-ethoxy]-phenyl}-2-methyl-propionic acid; and
- 2-(3-Chloro-phenoxy)-2-methyl-3-(4-{2-[5-methyl-2-(1-methyl-cyclohexyl)-oxazol-4-yl]-ethoxy}-phenyl)-propionic acid.

6. A pharmaceutical composition comprising a pharmaceutically acceptable carrier and a compound of claim 1, or a pharmaceutically acceptable salt, or hydrate thereof.

* * * * *